(12) United States Patent
Shetty et al.

(10) Patent No.: US 11,479,777 B2
(45) Date of Patent: Oct. 25, 2022

(54) METHODS AND SYSTEMS FOR METHYLOTROPHIC PRODUCTION OF ORGANIC COMPOUNDS

(71) Applicant: Ginkgo Bioworks, Inc., Boston, MA (US)

(72) Inventors: Reshma P. Shetty, Boston, MA (US); Curt R. Fischer, Sunnyvale, CA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

(21) Appl. No.: 15/937,619

(22) Filed: Mar. 27, 2018

(65) Prior Publication Data

US 2018/0216120 A1    Aug. 2, 2018

Related U.S. Application Data

(62) Division of application No. 14/649,973, filed as application No. PCT/US2013/073582 on Dec. 6, 2013, now abandoned.

(60) Provisional application No. 61/734,472, filed on Dec. 7, 2012.

(51) Int. Cl.
| | |
|---|---|
| *C12N 15/74* | (2006.01) |
| *C12N 15/52* | (2006.01) |
| *C12N 1/20* | (2006.01) |
| *C12N 1/36* | (2006.01) |
| *C12P 7/16* | (2006.01) |
| *C12P 7/40* | (2006.01) |

(52) U.S. Cl.
CPC ............... *C12N 15/74* (2013.01); *C12N 1/20* (2013.01); *C12N 1/36* (2013.01); *C12N 15/52* (2013.01); *C12P 7/16* (2013.01); *C12P 7/40* (2013.01); *Y02E 50/10* (2013.01)

(58) Field of Classification Search
None
See application file for complete search history.

(56) References Cited

U.S. PATENT DOCUMENTS

| | | |
|---|---|---|
| 1,746,464 A | 2/1930 | Fischer |
| 5,302,525 A | 4/1994 | Groleau et al. |
| 7,118,896 B2 | 10/2006 | Kalscheuer et al. |
| 7,256,016 B2 | 8/2007 | San et al. |
| 7,803,589 B2 | 9/2010 | Burk et al. |
| 7,923,227 B2 | 4/2011 | Hickey et al. |
| 7,981,647 B2 | 7/2011 | Berry et al. |
| 8,349,587 B2 | 1/2013 | Fischer et al. |
| 9,902,980 B2 | 2/2018 | Fischer et al. |
| 2003/0148416 A1* | 8/2003 | Berry ............... C12N 9/0006 435/67 |
| 2003/0157636 A1 | 8/2003 | Figueira et al. |
| 2004/0142435 A1 | 7/2004 | Gunji et al. |
| 2005/0287625 A1* | 12/2005 | Miller .............. C12N 1/20 435/67 |
| 2007/0065903 A1* | 3/2007 | Dicosimo ......... C12N 9/0071 435/67 |
| 2007/0264688 A1 | 11/2007 | Venter et al. |
| 2007/0269862 A1 | 11/2007 | Glass et al. |
| 2010/0086958 A1 | 4/2010 | Davis et al. |
| 2010/0228067 A1 | 9/2010 | Peterson et al. |
| 2012/0064622 A1 | 3/2012 | Fischer et al. |
| 2015/0037853 A1 | 2/2015 | Fischer et al. |
| 2015/0315599 A1 | 11/2015 | Shetty et al. |

FOREIGN PATENT DOCUMENTS

| | | |
|---|---|---|
| WO | WO-2007041872 A1 | 4/2007 |
| WO | WO-2007/139925 A2 | 12/2007 |
| WO | WO-2007140339 A2 | 12/2007 |
| WO | WO-2009/022754 A1 | 2/2009 |
| WO | WO-2009154753 A2 | 12/2009 |
| WO | WO-2010028262 A1 | 3/2010 |
| WO | WO-2011028264 A1 | 3/2010 |
| WO | WO-2010042197 A1 | 4/2010 |
| WO | WO-2010070295 A1 | 6/2010 |
| WO | WO-2011088425 A2 | 7/2011 |
| WO | WO-2013/066848 A1 | 5/2013 |
| WO | WO-2014/089436 A1 | 6/2014 |

OTHER PUBLICATIONS

Donald et al (Applied and Environmental Microbiology, 63(9):3341-3344, 1997).*
Urakami (J. Gen. Appl. Microbiol. 32:317-341, 1986) and Barry et al (US 2003/0148416).*
Meyer et al, Nature Communications 9:15081-10, 2018.*
IDI_ECOLI AC Q46822, May 30, 2000 with sequence version 1 of Nov. 1, 1996 in the UniProtKB/Swiss-Prot database).*
Hahn et al (Journal of Bacteriology 181(15):4499-4504, 1999).*
Abelson et al., "Carbon Isotope Fractionation in Formation of Amino Acids by Photosynthetic Organisms," Proc. Natl. Acad. Sci. USA. 47(5): 623-632 (1961).
Accession No. AXX60695, 3 pages (Jun. 10, 2010).
Agrawal, P. et al., An algorithm for operating a fed-batch fermentor at optimum specific-growth rate, Biotechnology and Bioengineering, 33: 115-125 (1989).
Aharoni et al., "Identification of the SAAT Gene Involved in Strawberry Flavor Biogenesis by Use of DNA Microarrays," The Plant Cell. 12: 647-661 (2000).

(Continued)

*Primary Examiner* — Patricia Duffy
(74) *Attorney, Agent, or Firm* — Wolf, Greenfield & Sacks, P.C.

(57) ABSTRACT

The present disclosure identifies pathways, mechanisms, systems and methods to confer production of carbon-based products of interest, such as sugars, alcohols, chemicals, amino acids, polymers, fatty acids and their derivatives, hydrocarbons, isoprenoids, and intermediates thereof, in engineered and/or evolved methylotrophs such that these organisms efficiently convert C1 compounds, such as formate, formic acid, formaldehyde or methanol, to organic carbon-based products of interest, and in particular the use of organisms for the commercial production of various carbon-based products of interest.

10 Claims, 18 Drawing Sheets

Specification includes a Sequence Listing.

(56) References Cited

OTHER PUBLICATIONS

Alber et al., "Malonyl-Coenzyme A Reductase in the Modified 3-Hydroxypropionate Cycle for Autotrophic Carbon Fixation in Archaeal *Metallosphaera* and *Sulfolobus* spp," Journal of Bacteriology. 188(24): 8551-8559 (2006).
Alber et al., "Propionyl-Coenzyme a Synthase from Chloroflexus aurantiacus, as Key Ensyme of the 3-Hydroxypropionate Cycle for Autotrophic $CO_2$ Fixation," The Journal of Biological Chemistry. 277(14): 12137-12143 (2002).
Andersen et al., "New Unstable Variants of Green Fluorescent Protein for Studies of Transient Gene Expression in Bacteria," Applied and Environmental Microbiology, 64(6): 2240-2246 (1998).
Anderson et al., "Environmental Signal Integration by a Modular AND Gate," Molecular Systems Biology. 3:133 (2007).
Aoshima et al., "A Novel Biotin Protein Required for Reductive Carboxylation of 2-Oxoglutarate by Isocitrate Dehydrogenase in Hydrogenobacter thermophilus TK-6," Molecular Microbiology. 51(3): 791-798 (2004).
Aoshima et al., "A Novel Enzyme, Citryl-CoA Lyase, Catalysing the Second Step of the Citrate Cleavage Reaction in Hydrogenobacter thermophilus TK-6," Molecular Microbiology. 52(3): 763-770 (2004).
Aoshima et al., "A Novel Enzyme, Citryl-CoA Synthetase, Catalysing the First Step of the Citrate Cleavage Reaction in Hydrogenobacter thermophilus TK-6," Molecular Microbiology. 52(3): 751-761 (2004).
Aoshima et al., "A Novel Oxalosuccinate-Forming Enzyme Involved in the Reductive Carboxylation of 2-Oxoglutarate in Hydrogenobacter thermophilus TK-6," Molecular Microbiology. 62(3): 748-759 (2006).
Baba et al., "Construction of *Escherichia coli* K-12 In-Frame, Single-Gene Knockout Mutants: The Keio Collection," Molecular Systems Biology. 2006.2008 (2006).
Bai et al., "Ethanol Fermentation Technologies from Sugar and Starch Feedstocks," Biotechnology Advances. 26(1): 89-105 (2008).
Bailer et al., "Determination of Saponifiable Glycerol in 'Bio-Diesel,'" Fresenius' Journal of Analytical Chemistry. 340(3): 186 (1991).
Bar-Even et al., "Design and Analysis of Synthetic Carbon Fixation Pathways," Proc. Natl. Acad. Sci. USA. 107(19): 8889-8894 (2010).
Bassham et al., "The Path of Carbon in Photosynthesis. XXI. The Cyclic Regeneration of Carbon Dioxide Acceptor," Radiation Laboratory and Department of Chemistry, University of California, Berkeley. 76:1760-1770 (1954).
Bayer et al., "Synthesis of Methyl Halides from Biomass Using Engineered Microbes," JACS. 131(18): 6508-6515 (2009).
Berrios-Rivera et al., "The Effect of the NAPRTase Overexpression on the Total Levels of NAD, The $NADH/NAD^+$ Ratio, and the Distribution of Metabolites in *Escherichia coli*," 4(3): 238-247 (2002).
Bourque, D. et al., High cell density production of poly-beta-hydroxybutyrate (PHB) from methanol by Methylobacterium extorquens: production of high-molecular-mass PHB, Appl. Microbiol. Biotechnol., 44: 367-376 (1995).
Brugna-Guiral et al., "[NiFe] Hydrogenases from the Hyperthermophilic Bacterium *Aquifex aeolicus*: Properties, Function, and Phylogenetics," Extremophiles. 7(2):145-157 (2003).
Buchanan et al., "A Reverse KREBS Cycle in Photosynthesis: Consensus at Last," Photosynthesis Research. 24: 47-53 (1990).
Burgdorf et al., "The Soluble NAD+-Reducing [NiFe]-Hydrogenase from Ralstonia eutropha H16 Consists of Six Subunits and can be Specifically Activated by NADPH," Journal of Bacteriology. 187(9): 3122-3132 (2005).
Camilli et al., "Bacterial Small-Molecule Signaling Pathways," Science. 311(5794): 1113-1116 (2006).
Campbell et al., "Adaptations to Submarine Hydrothermal Environments Exemplified by the Genome of Nautilia profundicola," PLoS Genetics. 5(2): e1000362 (2009).
Campbell et al., "Growth and Phylogenetic Properties of Novel Bacteria Belonging to the Epsilon Subdivision of the Preteobacteria Enriched from Alvinella pompejana and Deep-Sea Hydrothermal Vents," Applied and Environmental Microbiology. 67(10):4566-4572 (2001).
Canton et al., "Refinement and Standardization of Synthetic Biological Parts and Devices," Nature Biotechnology. 26(7): 787-793 (2008).
Cheesbrough et al., "Alkane Biosynthesis by Decarbonylation of Aldehydes Catalyzed by a Particulate Preparation from Pisum sativum," Proc. Natl. Acad. Sci. USA. 81(21): 6613-6617 (1984).
Chen et al., "Biosynthesis of Ansatrienin (Mycotrienin) and Naphthomycin Identification and Analysis of Two Separate Biosynthetic Gene Clusters in Streptomyces collinus Tu 1892," European Journal of Biochemistry. 261(1): 98-107 (1999). cited byother.
Chica, R.A. et al., Semi-rational approaches to engineering enzyme activity: combining the benefits of directed evolution and rational design, Current Opinion in Biotechnology, 16: 378-384 (2005).
Chin et al., "Improved NADPH Supply for Xylitol Production by Engineered *Escherichia coli* with Glycolytic Mutations," Biotechnol. Prog. 27(2): 333-341 (2011).
Cline, Joel. "Spectrophotometric Determination of Hydrogen Sulfide in Natural Waters," Limnology and Oceanography. 14(3): 454-458 (1969).
Contador, C.A. et al., Ensemble modeling for strain development of L-lysine-producing *Escherichia coli*, Metablic Engineering, 11: 221-233 (2009).
Cropp et al., "Identification of a Cyclohexylcarbonyl CoA Biosynthetic Gene Cluster and Application in the Production of Doramectin," Nature Biotechnology. 18(9): 980-983 (2000).
Crowther, Gregory J. et al., Formate as the main branch point for methylotrophic metabolism in Methylobacterium extorquens AM1, Journal of Bacteriology, 190(14): 5057-5062 (2008).
Davis et al., "Design, Construction and Characterization of a Set of Insulated Bacterial Promoters," Nucleic Acids Research. doi:10.1093 (2010).
Dellomonaco et al., "Engineered Reversal of the .beta.-oxidation Cycle for the Synthesis of Fuels and Chemicals," Nature. 476(7360): 355-361 (2011).
Dennis et al., "Alkane Biosynthesis by Decarbonylation of Aldehyde Catalyzed by a Microsomal Preparation from Botryococcus brraunii," Archives of Biochemistry and Biophysics. 287(2): 268-275 (1991).
Denoya et al., "A Second Branched-Chain .alpha.-Keto Acid Dehydrogenase Gene Cluster (bkdFGH) from Streptomyces avermitilis: Its Relationship to Avermectin Biosynthesis and the Construction of a bkdF Mutant Suitable for the Production of Novel Antiparasitic Avermectins," Journal of Bacteriology. 177(12): 3504-3511 (1995).
Deshpande, Mukund, "Ethanol Production from Cellulose by Coupled Saccharification/Fermentation Using *Saccharomyces cerevisiae* and Cellulase Complex from Sclerotium rolfsii UV-8 Mutant," Applied Biochemistry and Biotechnology. 36(3): 227-234 (1992).
Dettman et al., "Controls on the Stable Isotope Composition of Seasonal Growth Bands in Aragonitic Fresh-Water Bivalves (Unionidae)," Geochimica et Cosmochimica Acta. 63(7/8): 1049-1057 (1999).
Dunham, M.J., Experimental Evolution in Yeast: A practical guide, Methods in Enxymology, 470: 487-507 (2010).
Edgar, Roger C., "Muscle: A Multiple Sequence Alignment Method with Reduced Time and Space Complexity," BMC Bioinformatics. 5: 113 (2004).
Edgar, Roger C., "Muscle: Multiple Sequence Alignment with High Accuracy and High Throughput," Nucleic Acids Research. 32(5): 1792-1797 (2004).
Edwards et al., "Characterizing the Metabolic Phenotype: A Phenotype Phase Plane Analysis," Biotechnology and Bioengineering. 77(1): 27-36 (2002).
Eisenreich et al., "Retrobiosynthetic Analysis of Carbon Fixation in the Phototrophic Eubacterium *Chloroflexus aurantiacus*," Eur. J. Biochem. 215(3): 619-632 (1993).
Evans et al., "[.sup.13C]Propionate Oxidation in Wild-Type and Citrate Synthase Mutant *Escherichia coli*: Evidence for Multiple Pathways of Propionate Utilization," Biochem. J. 291: 927-932 (1993).

(56) References Cited

OTHER PUBLICATIONS

Evans et al., "A New Ferredoxin-Dependent Carbon Reduction Cycle in a Photosynthetic Bacterium," Biochemistry. 55(4): 928-934 (1966).
Evdokimov, E.V. et al., Mikrobiologiya, 61(4): 652-659 (1992).
Farquhar et al., "Carbon Isotope Discrimination and Photosynthesis," Annu. Rev. Plant Physiol. Plant Mol. Biol. 40: 503-537 (1989).
Ferenci et al., "Purification and Properties of 3-Hexulose Phosphate Synthase and Phospho-3-Hexuloisomerase from Methylococcus capsulatus," Biochem. J. 144(3): 477-486 (1974).
Fischer et al., Assessment of heterologous butyrate and butanol pathway activity by measurement of intracellular pathway intermediates in recombinant *Escherichia coli*, Applied Microbial Biotechnology 88: 265-275 (2010).
Fogel et al., "Prokaryotic Genome Size and SSU rDNA Copy Number: Estimation of Microbial Relative Abundance from a Mixed Population," Microbial Ecology. 38(2): 93-113 (1999).
Fong et al., "Metabolic Gene-Deletion Strains of *Escherichia coli* Evolve to Computationally Predicted Growth Phenotypes," Nature Genetics. 36(10): 1056-1058 (2004).
Fong et al., "Predicting Specificity in bZIP Coiled-Coil Protein Interactions," Genome Biology. 5(2): R11.1-R11.10 (2004).
Friedmann et al., "Properties of R-Citramalyl-Coenzyme A Lyase and Its Rold in the Autotrophic 3-Hydroxypropionate Cycle of Chloroflexus aurantiacus," Journal of Bacteriology. 189(7): 2906-2914 (2007).
Friedmann et al., "Properties of Succinyl-Coenzyme A: L-Malate Coenzyme A Transferase and Its Role in the Autotrophic 3-Hydroxypropionate Cycle of Chloroflexus aurantiacus," Journal of Bacteriology. 188(7): 2646-2655 (2006).
Gehring and Arnon. "Purification and Properties of .alpha.-Ketoglutarate Synthase from a Photosynthetic Bacterium," The Journal of Biological Chemistry. 247(21): 6963-6969 (1972).
Gerhold et al., "DNA Chips: Promising Toys Have Become Powerful Tools," Trends in Biochemical Science. 24(5):168-173 (1999).
Grantham et al., "Codon Catalog Usage and the Genome Hypothesis," Nucleid Acids Research. 8(1): r49-r62 (1980).
Greene et al., "Artificially Evolved Synechococcus PCC6301 Rubisco Variants Exhibit Improvements in Folding and Catalytic Efficiency," Biochem. J. 404(3):571-524 (2007).
Griesbeck et al., "Biological Sulfide Oxidation: Sulfide-Quinone Reductase (SQR), the Primary Reaction," Recent Research Developments in Microbiology. 4:129-203 (2000).
Gul-Karaguler et al., "A Single Mutation in the NAD-specific Formate Dehydrogenase from Candida methylica Allows the Enzyme to Use NADP," Biotechnology Letters. 23(4):283-287 (2001).
Gutteridge et al., "Expression of Bacterial Rubisco Genes in *Escherichia coli*," Phil. Trans. R. Soc. Lond. B. 313: 433-445 (1986).
Han and Reynolds. "A Novel Alternative Anaplerotic Pathway to the Glyoxylate Cycle in Streptomycetes," Journal of Bacteriology. 179(16): 5157-5164 (1997).
Harms, N. and Van Spanning, R.J.M., C1 Metabolism in Paracoccus denitrificans: Genetics of Paracoccus denitrificans, Journal of Bioenergetics and Biomembrances, 23(2): 187-209 (1991).
Hatrongjit and Packdibamrung. "A Novel NADP.sup.+-dependent Formate Dehydrogenase from Burkholderia stabilis 15516: Screening, Purification and Characterization," Enzyme and Microbial Technology. 46(7):557-561 (2010).
Hawkley and McClure. "Compilation and Analysis of *Escherichia coli* Promoter DNA Sequences," Nucleic Acids Research. 11(8): 2237-2255 (1983).
Hayes, John M. "Fractionation of Carbon and Hydrogem Isotopes in Biosynthetic Processes," Rev. Mineral. Geochem. 43(1):225-277 (2001).
Helling and Kukora. "Nalidixic Acid-Resistant Mutants of *Escherichia coli* Deficient in Isocitrate Dehydrogenase," Journal of Bacteriology. 105(3): 1224-1226 (1971).
Henry et al., "Genome-Scale Thermodynamic Analysis of *Escherichia coli* Metabolism," Biophysical Journal. 90(4):1453-1461 (2006).
Henstra et al., "Microbiology of Synthesis Gas Fermentation for Biofuel Production," Current Opinion in Biotechnology. 18(3): 200-206 (2007).
Herter et al., "A Bicyclic Autotrophic CO.sub.2 Fixation Pathway in Chloroflexus aurantiacus," Journal of Bacteriology. 277(23): 20277-20283 (2002).
Herter et al., "L-Malyl-Coenzyme A Lyases/.beta.-Methylmalyl-Coenzyme A Lyase from Chloroflexus aurantiacus, a Biofunctional Enzyme Involved in Autotrophic CO.sub.2 Fixation," Journal of Bacteriology. 184(21): 5999-6006 (2002).
Hirt, W. et al., Formaldehyde incorporation by a new methylotroph (L3), Applied and Environmental Microbiology, 36(1): 56-62 (1978).
Ho et al., "Genetically Engineered *Saccharomyces* Yeast Capable of Effective Cofermentation of Glucose and Xylose," Applied and Environmental Microbiology. 64(5): 1852-1859 (1998).
Hoffmeister et al., "Mitochondrial trans-2-Enoyl-CoA Reductase of Wax Ester Fermentation from Euglena gracilis Defines a New Family of Enzymes Involved in Lipid Synthesis," The Journal of Biological Chemistry. 280(6): 4329-4338 (2005). cited byother.
Holo, Helge. "Chloroflexus aurantiacus Secretes 3-Hydroxypropionate, A Possible Intermediate in the Assimilation of CO.sup.2 and Acetate," Archives of Microbiology. 151(3): 252-256 (1989).
Hou et al., "Metabolic Impact of Increased NADH Availability in *Saccharomyces cerevisiae*," Applied and Environmental Microbiology. 76(3): 851-859 (2010).
Huan-Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.
Hugler et al., "Autotrophic CO.sub.2 Fixation via the Reductive Tricarboxylic Acid Cycle in Different Lineages Within the Phylum Aquificae: Evidence for Two Ways of Citrate Cleavage," Environmental Microbiology. 9(1): 81-92 (2007).
Hugler et al., "Beyond the Calvin Cycle: Autotrophic Carbon Fixation in the Ocean," Annu. Rev. Marine. Sci. 3:261-289 (2011).
Hugler et al., "Malonyl-Coenzyme A Reductase from Chloroflexus aurantiacus, a Key Enzyme of the 3-Hydroxypropionate Cycle for Autotrophic CO.sub.2 Fixation," Journal of Bacteriology. 184(9):2404-2410 (2002).
Hugler et al., "Pathways of Carbon and Energy Metabolism of the Epibiotic Community Associated with the Deep-Sea Hydrothermal Vent Shrimp Rimicaris exoculata," PLoS One. 6(1):e16018 (2011).
Huisman and Gray, "Towards Novel Processes for the Fine-Chemical and Pharmaceutical Industries," Curr. Opin. Biotechnol. 13(4):352-358 (2002).
Ikeda et al., "Two Tandemly Arranged Ferredoxin Genes in the Hydrogenobacter thermophilus Genome: Comparative Characterization ofthe Recombinant [4FE-4S] Ferredoxins," Biosci. Biotechnol. Biochem. 69(6):1172-1177 (2005).
Inokuma et al., "Characterization of Enzymes Involved in the Ethanol Production of *Moorella* sp. HUC22-1," Arch. Microbiol. 188(1):37-45 (2007).
International Preliminary Report on Patentability for PCT/US2012/06540, 9 pages (dated May 15, 2014).
International Search Report for PCT/U2012/062540, 5 pages (dated Apr. 10, 2013).
International Search Report for PCT/US2013/073582, 5 pages (dated Mar. 20, 2015).
Janausch et al., "C.sub.4-Dicarboxylate Carriers and Sensors in Bacteria," Biochemica et Biophysica Acta. 1553(1-2): 39-56 (2002).
Jukes and Osawa. "Mini Review: Evolutionary Changes in the Genetic Code," Comp. Biochem. Physiol. 106B(3): 489-494 (1993).
Kalscheuer and Steinbuchel. "A Novel Bifunctional Wax Ester Synthase/Acyl-CoA:Diacylglycerol Acyltransferases Mediates Wax Ester and Triacylglycerol Biosynthesis in Acinetobactor calcoaceticus ADP1," The Journal of Biological Chemistry.278(10):8075-8082 (2003).
Kalscheuer et al., "Microdiesel: *Escherichia coli* engineered for Fuel Production," Microbiology. 152:2529-2536 (2006).
Kanao et al., "Characterization of Isocitrate Dehydrogenase from the Green Sulfur Bacterium *Chlorobium limicola*," Eur. J. Biochem. 269(7): 1926-1931 (2002).

(56) References Cited

OTHER PUBLICATIONS

Kanao et al., "Kinetic and Biochemical Analyses on the Reaction Mechanism of a Bacterial ATP-Citrate Lyase," Eur. J. Biochem. 269(14): 3409-3416 (2002).

Kaneda, T. "Iso- and Antesio-Fatty Acids in Bacteria: Biosynthesis, Function, and Taxonomic Significance," Microbiological Reviews. 55(2): 288-302 (1991).

Kapust and Waugh. "*Escherichia coli* Maltose-Binding Protein is Uncommonly Effective at Promoting the Solubility of Polypeptides to Which it is Fused," Protein Science. 8:1668-1674 (1999).

Keasling, Jay D. "Gene-Expression Tools for the Metabolic Engineering of Bacteria," Trends in Biotechnol. 17(11):452-460 (1999).

Kelly et al., "Methodology: Measuring the Activity of BioBrick Promoters Using an in vivo Reference Standard," Journal of Biological Engineering. 3(4): 1-13 (2009).

Kelly et al., Autotrophic Metabolism of Formate by Thiobacillus Strain A2, Journal of General Microbiology. 144:1-13 (1979).

Kelly, D.P. et al., Proposal for the reclassification of Thiobacillus novellus as *Starkeya novella* gen. nov., comb. nov., in the a-subclass of the Proteobacteria, International Journal of Systematic and Evolutionary Microbiology, 50: 1797-1802 (2000).

Kemp, M.B. "Hexose Phosphate Synthetase from Methylococcus capsulatus Makes a D-arabino-3-Hexulose Phosphate," Biochem J. 139(1):129-134 (1974).

Kemp, M.B. "The Hexose Phosphate Synthetase of Methylococcus capsulatus," Biochem J. 127(3):64P-65P (1972).

Kiely, P.D. et al., Anodic biofilms in microbial fuel cells harbor low numbers of higher-power-producing bacteria than abundant genera, Appl. Microbiol. Biotechnol., 88: 371-380 (2010).

Kim and Unden, "The I-Tartrate/Succinate AntiporterTtdT (YgjE) of I-Tartrate Fermentation in *Escherichia coli*," Journal of Bacteriology. 189(5): 1597-1603 (2007).

Kim et al., "Production of Biohydrogen by Heterologous Expression of Oxygen-Tolerant Hydrogenovibrio marinus [NiFe]-Hydrogenase in *Escherichia coli*," Journal of Biotechnology. 1155(3):312-319 (2011).

Klimke et al., "The National Center for Biotechnology Information's Protein Clusters Database," Nucleic Acids Research. 37:D216-D223 (2009).

Knight, T., "Draft Standard for Biobrick Biological Parts," http://hdl.handle.net/1721.1/45138 (2007).

Knight, T., "Idempotent Vector Design for Standard Assembly of Biobricks," http://hdl.handle.net/1721.1/21168 (2003).

Knothe et al., "Biodiesel: The Use of Vegetable Oils and Their Derivatives as Alternative Diesel Fuels," Am. Chem. Soc. Symp. Series, vol. 666, Fuels and Chemicals from Biomass, Chapter 10, pp. 172-208 (1997).

Knothe, Gerhard. "Dependence of Biodiesel Fuel Properties on the Structure of Fatty Acid Alkyl Esters," Fuel Processing Technology. 86:1059-1070 (2005).

Knothe, Gerhard. "Rapid Monitoring of Transesterification and Assessing Biodiesel Fuel Quality by Near-Infrared Spectroscopy Using a Fiber-Optic Probe," J. Am. Oil Chem. Soc. 76(7): 795-800 (1999).

Kolkman et al., "Directed Evolution of Proteins by Exon Shuffling," Nat. Biotechnol. 19(5):423-428 (2001).

Larkum, AWD. "Limitation and Prospects of Natural Photosynthesis for Bioenergy Production," Current Opinion in Biotechnology. 21(3):271-276 (2010).

LaRue and Kurz. "Estimation of Nitrogenase Using a Colorimetric Determination for Ethylene," Plant Physiol. 51(6):1074-1075 (1973).

Li et al., "Alteration of the Fatty Acid Profile of Streptomyces coelicolor by Replacement of the Initial Enzyme 3-Ketoacyl Carrier Protein Synthase III (FabH)," Journal of Bacteriology. 187(11): 3795-3799 (2005).

Liu et al., "Formate Dehydrogenase of Clostridium pasteurianum," Journal of Bacteriology. 159(1):375-380 (1984).

Marcia et al., "A New Structure-Based Classification of Sulfide: Quinone Oxidoreductases," Proteins. 78(5):1073-1083 (2010).

Marrakchi et al., "A New Mechanism for Anaerobic Unsaturated Fatty Acid Formation in *Streptococcus pneumoniae*," The Journal of Biological Chemistry. 277(47):44809-44816 (2002).

Marrakchi et al., "Mechanistic Diversity and Regulation of Type II Fatty Acids Synthesis," Biochem. Soc. Trans. 30(6): 1050-1055 (2002).

Martin et al., "Redesigning Cells for Production of Complex Organic Molecules," ASM News. 68(7): 336-343 (2002).

Martinez-Alonso et al., "Rehosting of Bacterial Chaperones for High-Quality Protein Production," Applied and Environmental Microbiology, 75(24): 7850-7854 (2009).

Martinez-Alonso et al., "Side Effects of Chaperone Gene Co-Expression in Recombinant Protein Production," Microbial Cell Factories. 9(64):1-6 (2010).

Marty and Planas. "A Comparison of Methods to Determine Algal .delta . . . sup.13C in Freshwater," Limnol Oceanogr Methods. 6:51-63 (2008).

Mendoza et al., "Thermal Regulation of Membrane Fluidity in *Escherichia coli*," The Journal of Biological Chemistry. 258(4):2098-2101 (1983).

Menendez et al., "Presences of Acetyl Coenzyme A (CoA) Carboxylase and Propionyl-COA Carboxylase in Autotrophic Crenarchaeota and Indication for Operation of a 3-Hydroxypropionate Cycle in Autotrophic Carbon Fixation," Journal of Bacteriology.181(4):1088-1098 (1999).

Minshull and Stemmer. "Protein Evolution by Molecular Breeding," Curr. Opin. Chem. Biol. 3(3):284-290 (1999).

Miroshnichenko et al., "*Nautilia lithotrophica* gen. nov., sp. nov., a Thermophilic Sulfuro-Reducing .epsilon.-Proteobacterium Isolated from a Deep-Sea Hydrothermal Vent," International Journal of Systematic and Evolutionary Microbiology.52:1299-1304 (2002).

Mitsui et al., "A Novel Operon Encoding Formaldehyde Fixation: the Ribulose Monophosphate Pathway in the Gram-Positive Facultative Methylotrophic Bacterium *Mycobacterium gastri* MB19," Journal of Bacteriology. 182(4):944-948 (2000).

Monson and Hayes. "Biosynthetic Control of the Natural Abundance of Carbon 13 at Specific Positions within Fatty Acids in *Escherichia coli*," The Journal of Biological Chemistry. 255(23):11435-11441 (1980).

Moriya et al., "KAAS: An Automatic Genome Annotation and Pathway Reconstruction Server," Nucleic Acids Research. 35:W182-W185 (2007).

Morweiser et al., "Developments and Perspectives of Photobioreactors for Biofuel Production," Appl. Microbiol. Biotechnol. 87:1291-1301 (2010).

Murli et al., "A Role for the umuDC Gene Products of *Escherichia coli* in Increasing Resistance to DNA Damage in Stationary Phase by Inhibiting the Transition to Exponential Growth," Journal of Bacteriology. 182(4):1127-1135 (2000).

Murtagh, F. "Complexities of Hierarchic Clustering Algorithms: State of the Art," Computational Statistics Quarterly. 1(2):101-113 (1984).

Ober, Joyce A. "Sulfur," U.S. Geological Survey Minerals Yearbook. U.S. Department of the Interior U.S. Geological Survey. 74.1-74.17 (2010).

Orita et al., "Bifunctional Enzyme Fusion of 3-Hexulose-6-Phosphate Synthase and 6-Phospho-3-Hexuloisomerase," Appl. Microbiol. Biotechnol. 76:439-445 (2007).

Orita et al., "The Archaeon Pyrococcus horikoshii Possesses a Bifunctional Enzyme for Formaldehyde Fixation via the Ribulose Monophosphate Pathway," Journal of Bacteriology. 187(11):3636-3642 (2005).

Orita et al., "The Ribulose Monophosphate Pathway Subsititues for the Missing Pentose Phosphate Pathway in the Archaeon Thermococcus kodakaraensis," Journal of Bacteriology. 188(13):4698-4704 (2006).

Palaniappan et al., "Enhancement and Selective Production of Phoslactomycin B, a Protein Phosphatase IIa Inhibitor, Through Identification and Engineering of the Corresponding Biosynthetic Gene Cluster," The Journal of Biological Chemistry. 278(37):35552-35557 (2003).

Pant, D. et al., A review of the substrates used in microbial fuel cells (MFCs) for substainable energy production, Bioresource Technology, 101: 1533-1543 (2010).

(56) References Cited

OTHER PUBLICATIONS

Parikh et al., "Directed Evolution of RuBisCO Hypermorphs Through Genetic Selection in Engineered *E. coli*," Protein Engineering, Design & Selection. 19(3): 113-119 (2006).
Park, Myong-Ok. "New Pathway for Long-Chain n-Alkane Synthesis via 1-Alcohol in Vibrio furnissii M1," Journal of Bacteriology. 187(4):1426-1429 (2005).
Patton et al., "A Novel .DELTA. . . . sup.3, .DELTA. . . . sup.2-Enoyl-CoA Isomerase Involved in the Biosynthesis of the Cyclohexanecarboxylic Acid-Derived Moiety of the Polyketide Anastrienin A," Biochemistry. 39:7595-7604 (2000).
Pinske et al., "Metabolic Deficiences Revealed in the Biotechnologically Important Model Bacterium *Escherichia coli* BL21 (DE3)," PLoS One. 6(8): e22830 (2011).
Portis and Parry. "Discoveries in Rubisco (Ribulose 1,5-Biophosphate Carboxylase/Oxygenase): A Historical Perspective," Photosynth Res. 94:121-143 (2007).
Pramanik and Keasling. "Effect of *Escherichia coli* Biomass Composition on Central Metabolic Fluxes Predicted by a Stoichiometric Model," Biotechnol. Bioeng. 60(2): 230-238 (1998).
Pramanik and Keasling. "Stoichiometric Model of *Escherichia coli* Metabolism: Incorporation of Growth-Rate Dependent Biomass Composition and Mechanistic Energy Requirements," Biotechnol. Bioeng. 56(4): 398-421 (1997).
Rathnasingh et al., "Production of 3-Hydroxypropionic Acid via Malonyl-CoA Pathway Using Recombinant *Escherichia coli* Strains," Journal of Biotechnology. 157(4):633-640 (2012).
Reading and Sperandio. "Quorum Sensing: The Many Languages of Bacteria," FEMS Microbiol. Left. 254(1):1-11 (2006).
Rock et al., "Increased Unsaturated Fatty Acid Production Associated with a Suppressor of the fabA6(Ts) Mutation in *Escherichia coli*," Journal of Bacteriology. 178(18):5382-5387 (1996).
Roessner et al., "Overexpression in *Escherichia coli* of 12 Vitamin B.sub.12 Biosynthetic Enzymes," Protein Expression and Purification. 6(2):155-163 (1995).
Sachdev and Chirgwin. "Fusions to Maltose-Binding Protein: Control of Folding and Solubility in Protein Purification," Methods Enzymol. 326:312-321 (2000).
Sachdev and Chirgwin. "Solubility of Proteins Isolated from Inclusion Bodies is Enhanced by Fusion to Maltose-Binding Protein or Theoredoxin," Protein Expression and Purification. 12(1):122-132 (1998).
Saitou and Nei. "The Neighbor-joining Method: A New Method for Reconstructing Phylogenetic Trees," Mol. Biol. Evol. 4(4):406-425 (1987).
Sakata et al., "Carbon Isotopic Fractionation Associated with Lipid Biosynthesis by a Cyanobacterium: Relevance for Interpretation of Biomarker Records," Geochim. Cosmochim Acta. 61(24):5379-5389 (1997).
San et al., "Metabolic Engineering Through Cofactor Manipulation and its Effects on Metabolic Flux Redistribution in *Escherichia coli*," Metabolic Engineering. 4(2):182-192 (2002).
Sauer et al., "The Soluble and Membrane-Bound Transhydrogenases UdhA and PntAB Have Divergent Functions in NADPH Metabolism of *Escherichia coli*," The Journal of Biological Chemistry. 279(8):6613-6619 (2004).
Schendel, F.J. et al., L-lysine production at 50 degrees C by mutants of a newly isolated and characterized methylotrophic *Bacillus* sp, Applied and Environmental Microbiology, 56(4):963-970 (1990).
Schrader, Jens et al., Methanol-based industrial biotechnology: current status and future perspectives of methylotrophic bacteria, Trends in Biotechnology, 27(2): 107-115 (2009).
Schutz et al., "Sulfide-Quinone Reductase from Rhodobacter capsulates," The Journal of Biological Chemistry. 272(15):9890-9894 (1997).
Self et al., "Expression and Regulation of a Silent Operon, hyf, Coding for Hydrogenase 4 Isoenzyme in *Escherichia coli*," Journal of Bacteriology. 186(2):580-587 (2004).
Sen, S. et al., Developments in Directed Evolution for Improving Enzyme Functions, Appl. Biochem. Biotechnol., 143: 212-223 (2007).
Serov et al., "Engineering of Coenzyme Specificity of Formate Dehydrogenase from *Saccharomyces cerevisiae*," Biochem. J. 367:841-847 (2002).
Shetty et al., "Assembly of BioBrick Standard Biological Parts Using Three Antibiotic Assembly," Methods in Enzymology. 498: 311-326 (2011).
Shetty et al., "Methodology: Engineering BioBrick Vectors from BioBrick Parts," Journal of Biological Engineering. 2(5):1-12 (2008).
Shibata and Kobayashi. "Sulfide Oxidation in Gram-Negative Bacteria by Expression of the Sulfide-Quinone Reductase Gene of Rhodobacter capsulates and by Electron Transport to Ubiquinone," Can. J. Microbiol. 47(9):855-860 (2001).
Shpaer, Eugene G. "GeneAssist: Smith-Waterman and Other Database Similarity Searches and Identification of Motifs," Methods Mol. Biol. 70:173-187 (1997).
Smith et al., "*Nautilia profundicola* sp. nov., a Thermophilic Sulfur-Reducing Epsilonproteobacterium from Deep-Sea Hydrothermal Vents," Int. j. Syst. Evol. Microbiol. 58:1598-1602 (2008).
Smolke and Keasling. "Effect of Copy Number and mRNA Processing and Stabilization on Transcript and Protein Levels from an Engineered Dual-Gene Operon," Biotechnol. Bioeng. 78(4):412-424 (2002).
Smolke and Keasling. "Effect of Gene Location, mRNA Secondary Structures, and RNase Sites of Expression of Two Genes in an Engineered Operon," Biotechnol. Bioeng. 80(7): 762-776 (2002).
Smolke et al., "Controlling the Metabolic Flux Through the Carotenoid Pathway Using Directed mRNA Processing and Stabilization," Metabolic Engineering. 3(4):313-321 (2001).
Smolke et al., "Coordinated, Differential Expression of Two Genes Through Directed mRNA Cleavage and Stabilization by Secondary Structures," Appl. Environ. Microbiol. 66(12):5399-5405 (2000).
Sokal and Michener. "A Statistical method for Evaluating Systematic Relationships," The University of Kansas Science Bulletin. 38(22):1409-1438 (1958).
Strauss and Fuchs. "Enzymes of a Novel Autotrophic CO2 Fixation Pathway in the Phototrophic Bacterium *Chloroflexus aurantiacus*, the 3-Hydroxypropionate Cycle," Eur. J. Biochem. 215(3):633-643 (1993).
Strom et al., "The Carbon Assimilation Pathways of Methylococcus capsulatus, Pseudomonas methanica and Methylosinus trichosporium (OB3B) During Growth on Methane," Biochem. J. 144(3):465-476 (1974).
Sun et al., "Heterologous Expression and Maturation of an NADP-Dependent [NiFe]-Hydrogenase: A Key Enzyme in Biofuel Production," PLoS One. 5(5): e10526 (2010).
Tabita et al., "Expression and Assembly of Active Cyanobacterial Ribulose-1,5-Bisphosphate Carboxylase/Oxygenase in *Escherichia coli* Containing Stiochiometric Amounts of Large and Small Subunits," Proc. Natl. Acad. Sci. 82(18):6100-6103 (1985).
Tatusov et al., "A Genomic Perspective on Protein Families," Science. 248(5338):631-637 (1997).
Tatusov et al., "The COG Database: An Updated Version Includes Eukaryotes," BMC Bioinformatics. 4:1-14 (2003).
Theissen et al., Sulfide: quinone oxidoreductase (SQR) from the lugworm *Arenicola marina* shows cyanide and thioredoxin-dependent activity, FEBS Journal 275: 1131-1139 (2008).
Van Wezel et al., "GlcP Constitutes the Major Glucose Uptake System of Streptomyces Coelicolor A3(2)," Molecular Microbiology. 55(2):624-636 (2005).
Venturi, Vittorio. "Regulation of Quorum Sensing in Pseudomonas," FEMS Microbiol. Rev. 30(2):274-291 (2006).
Vignais and Billoud. "Occurrence, Classification, and Biological Function of Hydrogenases: An Overview," Chem. Rev. 107(10):4206-4272 (2007).
Vignais and Colbeau. "Molecular Biology of Microbial Hydrogenases," Curr. Issues Mol. Biol. 6(2):159-188 (2004).
Wells et al., "Engineering a Non-Native Hydrogen Production Pathway into *Escherichia coli* via a Cyanobacterial [NiFe] Hydrogenase," Metabolic Engineering. 13(4):445-453 (2011).

(56) References Cited

OTHER PUBLICATIONS

Whisstock, J.C. et al., Prediction of protein function from protein sequence and structure, Quarterly Reviews of Biophysics, 36(3): 307-340 (2003).

Written Opinion for PCT/U2012/062540, 13 pages (dated Apr. 10, 2013).

Written Opinion for PCT/US2013/073582 9 pages, (dated Mar. 20, 2015).

Wubbolts et al., "Variation of Cofactor Levels in *Escherichia coli* : Sequence Analysis and Expression of the pncB Gene Encoding Nicotinic Acid Phosphoribosyktrabsferase," The Journal of Biological Chemistry. 265(29): 17665-17672 (1990). cited byother.

Yamamoto et al., "Carboxylation Reaction Catalyzed by 2-Oxoglutarate:Ferredoxin Oxidoreductases from Hydrogenobacter thremophilus," Extremeophiles. 14(1):79-85 (2010).

Yamane et al., Annals New York Academy of Science, 364-381 (1986).

Yoon et al., "Purification and Characterization of Pyruvate:Ferredoxin Oxidoreductase from Hydrogenobacter thermophilus TK-6," Arch. Microbiol. 167(5):275-279 (1997).

Yurimoto, H. et al., The ribulose monophosphate pathway operon encoding formaldehyde fixation in a thermotolerant methylotroph, Bacillus brevis S1, FEMS Microbiology, Letters, 214: 189-193 (2002).

Zarzycki and Fuchs. "Co-Assimilation of Organic Substrates via the Autotrophic 3-Hydroxypropionate Bi-Cycle in Chloroflexus aurantiacus," Appl. Environ. Microbio. 77(17):6181-6188 (2011).

Zarzycki et al., "Identifying the Missing Steps of the Autotrophic 3-Hydroxypropionate CO.sub.2 Fixation Cycle in Chloroflexus aurantiacus," Proc. Natl. Acad. Sci. USA. 106(50):21317-21322 (2009).

Zdobnov and Apweiler. "InterProScan—An Integration Platform forthe Signature-Recognition Methods in InterPro," Bioinformatics. 17(9):847-848 (2001).

Zhang et al., "Molecular and Genetical Analysis of the Fructose-Glucose Transport System in the Cyanobacterium Synechocystis PCC6803," Molecular Microbiology. 3(9):1221-1229 (1989).

Zhang et al., "The FabR (YijC) Transcription Factor Regulates Unsaturated Fatty Acid Biosynthesis in *Escherichia coli*," The Journal of Biological Chemistry. 277(18):15558-15565 (2002).

Zhu et al., "Production of Ubiquinone in *Escherichia coli* by Expression of Various Genes Responsible for Ubiquinone Biosynthesis," Journal of Fermentation and Bioengineering. 79(5):493-495 (1995).

Zweiger, Gary. "Knowledge Discovery in Gene-Expression-Microarray Data: Mining the Information Output of the Genome," Trends Biotechnol. 17(11):429-436 (1999).

Leopold et al., GenBank Accession No. EU896065.1. Jun. 8, 2009. 1 page.

Wang et al., GenBank Accession No. AF119715.1. Apr. 22, 1999. 1 page.

[No Author Listed], isopentenyl diphosphate isomerase [*Escherichia coli* str. K-12 substr. MG1655]. NCBI Reference Sequence NP_417365. Jan. 11, 2012. Accessible at https://www.ncbi.nlm.nih.gov/protein/16130791?sat=17&satkey=16092533. 2 pages.

[No Author Listed], isopentenyl-diphosphate Delta-isomerase [*Escherichia coli* str. K-12 substr. MG1655]. NCBI Reference Sequence NP_417365. Oct. 11, 2018. Accessible at https://www.ncbi.nlm.nih.gov/protein/NP_417365.1/. 3 pages.

[No Author Listed], Paracoccus denitrificans PD1222 chromosome 1, complete sequence. Genbank Accession No. CP000489. Feb. 23, 2011. Accessible at https://www.ncbi.nlm.nih.gov/nuccore/119372524?sat=18&satkey=1747423. 642 pages.

[No Author Listed], Paracoccus denitrificans PD1222 chromosome 1, complete sequence. Genbank Accession No. CP000489. Jan. 28, 2014. Accessible at https://www.ncbi.nlm.nih.gov/nuccore/CP000489. 671 pages.

[No Author Listed], Paracoccus denitrificans PD1222 chromosome 2, complete sequence. Genbank Accession No. CP000490. Feb. 23, 2011. Accessible at https://www.ncbi.nlm.nih.gov/nuccore/119376152?sat=18&satkey=1747424. 382 pages.

[No Author Listed], Paracoccus denitrificans PD1222 chromosome 2, complete sequence. Genbank Accession No. CP000490. Jan. 28, 2014. Accessible at https://www.ncbi.nlm.nih.gov/nuccore/cp000490. 402 pages.

\* cited by examiner

SEQUENCE LISTING

```
<160> NUMBER OF SEQ ID NOS: 5

<210> SEQ ID NO 1
<211> LENGTH: 1902
<212> TYPE: DNA
<213> ORGANISM: Artificial Sequence
<220> FEATURE:
<223> OTHER INFORMATION: Synthetic DNA

<400> SEQUENCE: 1
atggacctac tctcaataca ggatccgagc ttcctcaaga acatgtctat cgacgagctc      60
gaaaagctct ccgacgagat tcggcagttc ctcatcactt ccctctctgc ttctggcggc     120
cacattggcc ccaacctcgg ggttgtagaa ctaacagtgg cgctgcataa agagttcaac     180
tcgccgaagg ataagttcct ctgggacgta ggccatcaga gctatgttca taaactgctg     240
actggacgcg gaaaggagtt cgccacgcta cgccagtaca agggtctatg cggattcccc     300
aaacgttccg agtcggaaca cgacgtgtgg gagaccggtc actcgagcac aagtctgtca     360
ggcgccatgg gaatggcagc tgcgcgggac atcaagggaa cggacgagta tatcatcccg     420
attatcgggg atggcgccct gaccggcggg atggccttgg aggcgctaaa ccacattggc     480
gatgaaaaga aggatatgat cgttattcta aatgacaatg agatgtccat cgcccccaac     540
gttggggcga tccacagtat gttgggacgt ttgcgcacag ccggtaagta ccagtgggtt     600
aaggacgaac tagagtacct tttcaagaaa atcccggcag tgggtggcaa actagcggcg     660
acggccgagc gtgttaagga ttcgctgaag tacatgttgg tttctggaat gttctttgaa     720
gaattggggt tcacgtatct tggccccgtc gatggacata gttatcatga actgatcgaa     780
aatctacaat acgcgaagaa gacgaagggc cctgtgctac tgcacgttat cacgaagaag     840
ggtaaaggtt acaagccggc tgaaaccgac acgatcggta cttggcatgg gaccggaccc     900
tataagatca ataccgggga tttcgtaaaa ccgaaggcgg cagctcctag ctggtcgggg     960
ctagtttcgg gaacagtcca gaggatggcc cgcgaagatg gacgcatcgt agcgatcacg    1020
ccggctatgc ctgttgggtc aaaactagag ggctttgcaa aagagtttcc tgatcgtatg    1080
```

```
tttgatgtag gaattgcaga gcagcatgcg gcaactatgg ctgctgctat ggcaatgcag    1140
gggatgaaac cgttccttgc catctactca acctttctgc aaagagcata tgatcaagtg    1200
gtgcatgata tttgccgcca aaacgctaat gtcttcatcg gaatcgatcg ggctggattg    1260
gtgggcgctg acgagaaac tcatcaaggc gtcttcgaca tcgccttcat gcgccacatc    1320
cccaacatgg ttctcatgat gccgaaggat gagaatgagg ccagcacat ggtgcatact    1380 gcactatcgt atgatgaggg cccgatagca atgcggttcc cgcgcggaaa cggattgggc    1440
gtaaagatgg acgagcagct taagacgatc ccgattggga cgtgggaagt cctgcggccc    1500
ggtaacgacg ctgttattct cacttttggc actactattg agatggccat cgaggcagcg    1560
gaggaactgc aaaaggaggg cctatctgtc cgcgtggtca atgcccggtt catcaaaccg    1620
atcgacgaga aaatgatgaa atccatttta aaggagggcc ttcccatcct cactatcgag    1680
gaggccgttc tcgagggcgg gtttggatcg agcatcctcg agtttgctca tgaccaaggg    1740
gagtatcata caccgatcga tcgaatgggg atacctgacc gtttcatcga gcacggatcc    1800
gtaactgccc tactagaaga aatcggactg actaagcagc aggtcgcaaa tcggatccga    1860
cttctgatgc ccccgaaaac tcacaaggga atcggatcgt ag                      1902

<210> SEQ ID NO 2
<211> LENGTH: 549
<212> TYPE: DNA
<213> ORGANISM: Artificial Sequence
<220> FEATURE:
<223> OTHER INFORMATION: Synthetic DNA

<400> SEQUENCE: 2
atgcagacgg agcacgttat cctccttaat gcacagggag tgccaacggg gacgctggag     60
aaatatgcgg cacacacggc agatacccgc ctccatttgg cctttctcttc ctggctgttc    120 aatgcgaagg gacaactcct cgtgacccgc gcgcactgt cgaagaaggc atggcctggc     180
gtctggacaa acagcgtgtg tggtcacccc caactgggag agtcgaacga ggatgcagtc    240
attcgccggt gccggtatga actaggcgtg gagatcacgc ctcctgagag tatttatcct    300
gatttccgct accgcgcgac cgacccgtcc ggcatcgtcg agaatgaggt ctgtccggta    360
ttcgcggcac gcaccacatc cgccctccag attaatgacg acgaggtcat ggactatcaa    420
tggtgtgacc tcgcagacgt actccacggg atcgacgcga cgccgtgggc cttttccccg    480
tggatggtca tgcaggccac taatcgcgag gcgcgaaaga ggctcagtgc attcacccag    540
ctaaagtaa                                                             549

<210> SEQ ID NO 3
<211> LENGTH: 1788
<212> TYPE: DNA
<213> ORGANISM: Artificial Sequence
<220> FEATURE:
<223> OTHER INFORMATION: Synthetic DNA

<400> SEQUENCE: 3
atggccacag agctcctttg ccttcaccgg cccatttcac tgactcacaa gcttttttcga    60 aatccacttc ctaaggttat tcaggcgaca ccactcacac ttaagttgcg atgtagtgta    120
tcgactgaga acgtttcgtt tactgagact gagactgaga cccgaagaag tgcgaattat    180
gagcccaatt cgtgggacta tgactatctt ctgagtagcg atacagatga gagcatcgag    240
gtatacaagg ataaagcgaa gaaactgaa gctgaagtcc gacgagaaat caacaatgag    300
```

| | |
|---|---|
| aaagcagaat tcttacact gcctgagctg atagacaatg ttcaaagact cggactcggg | 360 |
| taccgttttg aatccgatat aagacgagcg ctagaccgat tcgtgagttc aggaggattc | 420 |
| gacgctgtga ctaagacatc gctacatgct acagctctat cgtttagact attgcgacag | 480 |
| catggcttcg aagttagtca agaggccttt tcgggattta agaccaaaa tggcaatttt | 540 |
| cttaagaacc taaaagaaga tattaaagca atattatcgt tatatgaggc ttcattccta | 600 |
| gcgctcgagg gagagaatat tcttgacgaa gcgaaagtct tcgcaatatc acatttaaag | 660 |
| gaattgtcgg aggagaaaat cggaaaggat ctggcggagc aggtcaatca tgcacttgaa | 720 |
| ctaccccttc ataggagaac gcaacgatta gaggctgtgt ggtcgatcga ggcataccgg | 780 |
| aagaaagagg acgcagacca agtactgtta gaactagcta tacttgatta caacatgatc | 840 |
| caatcagtat accaacgaga cctacgcgaa acttcaagat ggtggagacg ggtcggtcta | 900 |
| gcaactaaac ttcatttcgc tcgagataga ctcatcgagt cgttctactg ggcagtggga | 960 |
| gtggccttcg agcctcaata ctccgactgc cggaatagtg tagcaaagat gttcagcttc | 1020 |
| gtaactatta tcgacgacat ttatgacgtg tatgggacac tggacgaact tgaattattc | 1080 |
| actgacgctg tggaacgatg ggacgtgaat gcgattgacg acctaccgga ctatatgaaa | 1140 |
| ttgtgctttt tagctttgta taacacaatt aatgaaatag cttatgacaa tctgaaagat | 1200 |
| aaaggtgaga acatcctacc ctacttaact aaggcctggg cagacctctg caatgcattt | 1260 |
| ttacaagagg caaagtggct ttacaataaa tctactccca cttttcgacga gtattttgga | 1320 |
| aatgcatgga agtcatcttc aggtcctcta caattagtgt tcgcgtactt cgcggtggtg | 1380 |
| caaaacatta aaaggaaga aatcgacaac ctccaaaaat atcatgacat tatttccaga | 1440 |
| ccttctcaca ttttccggct atgcaacgat cttgcttcag caagcgctga aatagcccga | 1500 |
| ggggagaccg ccaatagtgt atcatgctac atgcggacta agggcatcag tgaagaacta | 1560 |
| gctacagagt ctgtaatgaa tcttattgat gagacctgga gaaaatgaa caaggagaaa | 1620 |
| ctaggggca gtctgttcgc aaagcctttc gttgagactg ctatcaacct agcaaggcaa | 1680 |
| tctcattgca catatcacaa cggagacgcc catacatcac ccgacgaatt gacaagaaag | 1740 |
| cgggttctgt cagtaattac tgaacctatc ttaccattcg aacgctag | 1788 |

<210> SEQ ID NO 4
<211> LENGTH: 2424
<212> TYPE: DNA
<213> ORGANISM: Artificial Sequence
<220> FEATURE:
<223> OTHER INFORMATION: Synthetic DNA

<400> SEQUENCE: 4

| | |
|---|---|
| atgacctcgg tgagtgtgga gtcaggaact gtcagttgtc tttcttccaa caaccttatt | 60 |
| aggagaacgg cgaatcctca tcctaatatt tgggggtatg acttcgtcca tagtctaaag | 120 |
| agcccttaca cacatgacag ttcctaccga gagcgggccg aaactctaat ctcggaaatc | 180 |
| aaagtcatgc taggagggg agagctcatg atgacaccca gtgcttatga tactgcatgg | 240 |
| gtagccagag tcccatctat cgacggcagt gcttgcccgc aattcccaca aactgtggag | 300 |
| tggatcctta agaatcagct caaggacggg tcttggggta cagaaagcca cttcttactg | 360 |
| tctgatcgcc tgttagctac actaagttgt gtcctagcct tgctaaagtg gaaggtggca | 420 |
| gacgtccaag tagaacaggg catcgagttt ataaaacgaa atttacaagc aataaaagat | 480 |
| gagcgagacc aagattccct tgtaactgat ttcgaaatta ttttccctcc tcttttaaag | 540 |
| gaggcccaaa gtttgaactt gggactacca tacgatctgc cttatatacg gctgctgcaa | 600 |

```
acgaagcgtc aggaacgact cgcgaatttg tcaatggata agatccatgg gggaactctc      660
ctttcaagtc ttgaaggcat acaagacatc gttgaatggg agactataat ggacgtgcaa      720
tcgcaagacg gaagttttct ttcgtcacct gctagtacag cgtgcgtttt tatgcacaca      780
ggagatatga agtgcctaga ttttcttaac aacgtcttga caaaattcgg ctccagtgtg      840
ccctgcctgt atcccgtcga cctgctggag cgcttgctta ttgtcgacaa tgtggagcgc      900
ctaggaattg accgacactt cgagaaagag attaaagagg ctttagacta tgtgtacaga      960
cattggaatg accgaggaat cggttggggc cgactgtccc aatagcaga cctagaaacc      1020 acagctcttg gattccgtct gctaagactg catcgttaca acgtaagtcc cgttgtgctt      1080
gataacttta aggacgcgga cggtgagttt ttctgctcca ccgggcaatt taacaaggac      1140
gtagcatcga tgctgtcgct atatcgagct tctcagttgg cattcccaga ggagtcgatc      1200
cttgacgagg ctaagtcgtt ttccacacaa tatcttcgag aggcgctaga aaagtccgaa      1260 acatttcgt catggaacca ccgacaatcg ttatcggagg aaatcaagta cgccctgaaa      1320
acaagttggc atgcgtccgt tccacgagtc gaggcaaaac gatactgtca agtctatcgc      1380
caagactatg cacacctcgc aaagtcggtg tacaaactgc caaaggtcaa caatgagaaa      1440
atccttgaac tggcaaaact tgattttaac atcattcagt ctattcacca aaaggaaatg      1500
aaaaatgtta cctcgtggtt ccgagacagc ggtcttcctc tgtttacctt cgctcgtgaa      1560
agaccgctgg agttttactt tctcatagcc ggtggtacgt atgaaccaca gtatgcgaag      1620
tgccgatttt tgttcactaa ggtcgcctgt cttcagacag tgctggacga catgtatgac      1680
acttatggaa ccccttccga gcttaaatta tttacagaag ctgtccgacg atgggatttg      1740
agtttcactg agaacctacc cgattatatg aagttatgtt acaagattta ttatgatata      1800
gtgcacgagg tcgcttggga agtagaaaaa gagcaaggtc gggagcttgt gtcgttcttt      1860
cgaaaaggat gggaagacta tctactgggg tattacgaag aagctgagtg gctcgctgct      1920
gaatatgtcc ctacacttga tgaatacata aaaaatggta ttcatctat tgggcaacgg      1980 atactactgc tgtccggagt ccttataatg gagggtcaat tgttgagcca agaagcccct      2040
gaaaaggtag actatcccgg acgacgggtg ttgactgaac tgaatagttt gatcagtcgt      2100
ctggccgacg atactaagac ttataaagct gaaaaagctc ggggagagct tgcttcttcg      2160
atcgagtgtt acatgaagga tcatcctgga tgtcaagagg aggaagcttt gaatcacatt      2220
tatggcatcc tggaaccggc agtaaaagaa ctgacgagag aatttctgaa agcagatcat      2280
gttccctttc cgtgcaaaaa aatgctattc gacgaaaccc gagtcactat ggtcatattt      2340
aaagatggag acggcttcgg catctctaag ctcgaggtca agaccacat taaggaatgt      2400 ctgattgagc ccttgcccct ctag                                             2424
```

<210> SEQ ID NO 5
<211> LENGTH: 1822
<212> TYPE: PRT
<213> ORGANISM: Chloroflexus aurantiacus

<400> SEQUENCE: 5

```
Met Ile Asp Thr Ala Pro Leu Ala Pro Arg Ala Pro Arg Ser Asn
1               5                   10                  15

Pro Ile Arg Asp Arg Val Asp Trp Glu Ala Gln Arg Ala Ala Leu
            20                  25                  30

Ala Asp Pro Gly Ala Phe His Gly Ala Ile Ala Arg Thr Val Ile His
        35                  40                  45
```

-continued

Trp Tyr Asp Pro Gln His His Cys Trp Ile Arg Phe Asn Glu Ser Ser
50                  55                  60

Gln Arg Trp Glu Gly Leu Asp Ala Ala Thr Gly Ala Pro Val Thr Val
65                  70                  75                  80

Asp Tyr Pro Ala Asp Tyr Gln Pro Trp Gln Gln Ala Phe Asp Asp Ser
                85                  90                  95

Glu Ala Pro Phe Tyr Arg Trp Phe Ser Gly Leu Thr Asn Ala Cys
                100                 105                 110

Phe Asn Glu Val Asp Arg His Val Thr Met Gly Tyr Gly Asp Glu Val
            115                 120                 125

Ala Tyr Tyr Phe Glu Gly Asp Arg Trp Asp Asn Ser Leu Asn Asn Gly
130                 135                 140

Arg Gly Pro Val Val Gln Glu Thr Ile Thr Arg Arg Leu Leu
145                 150                 155                 160

Val Glu Val Val Lys Ala Ala Gln Val Leu Arg Asp Leu Gly Leu Lys
                165                 170                 175

Lys Gly Asp Arg Ile Ala Leu Asn Met Pro Asn Ile Met Pro Gln Ile
                180                 185                 190

Tyr Tyr Thr Glu Ala Ala Lys Arg Leu Gly Ile Leu Tyr Thr Pro Val
            195                 200                 205

Phe Gly Gly Phe Ser Asp Lys Thr Leu Ser Asp Arg Ile His Asn Ala
210                 215                 220

Gly Ala Arg Val Val Ile Thr Ser Asp Gly Ala Tyr Arg Asn Ala Gln
225                 230                 235                 240

Val Val Pro Tyr Lys Glu Ala Tyr Thr Asp Gln Ala Leu Asp Lys Tyr
                245                 250                 255

Ile Pro Val Glu Thr Ala Gln Ala Ile Val Ala Gln Thr Leu Ala Thr
                260                 265                 270

Leu Pro Leu Thr Glu Ser Gln Arg Gln Thr Ile Ile Thr Glu Val Glu
            275                 280                 285

Ala Ala Leu Ala Gly Glu Ile Thr Val Glu Arg Ser Asp Val Met Arg
290                 295                 300

Gly Val Gly Ser Ala Leu Ala Lys Leu Arg Asp Leu Asp Ala Ser Val
305                 310                 315                 320

Gln Ala Lys Val Arg Thr Val Leu Ala Gln Ala Leu Val Glu Ser Pro
                325                 330                 335

Pro Arg Val Glu Ala Val Val Val Arg His Thr Gly Gln Glu Ile
            340                 345                 350

Leu Trp Asn Glu Gly Arg Asp Arg Trp Ser His Asp Leu Leu Asp Ala
            355                 360                 365

Ala Leu Ala Lys Ile Leu Ala Asn Ala Arg Ala Gly Phe Asp Val
370                 375                 380

His Ser Glu Asn Asp Leu Leu Asn Leu Pro Asp Asp Gln Leu Ile Arg
385                 390                 395                 400

Ala Leu Tyr Ala Ser Ile Pro Cys Glu Pro Val Asp Ala Glu Tyr Pro
                405                 410                 415

Met Phe Ile Ile Tyr Thr Ser Gly Ser Thr Gly Lys Pro Lys Gly Val
            420                 425                 430

Ile His Val His Gly Gly Tyr Val Ala Gly Val Val His Thr Leu Arg
            435                 440                 445

Val Ser Phe Asp Ala Glu Pro Gly Asp Thr Ile Tyr Val Ile Ala Asp
            450                 455                 460

```
Pro Gly Trp Ile Thr Gly Gln Ser Tyr Met Leu Thr Ala Thr Met Ala
465                 470                 475                 480

Gly Arg Leu Thr Gly Val Ile Ala Glu Gly Ser Pro Leu Phe Pro Ser
            485                 490                 495

Ala Gly Arg Tyr Ala Ser Ile Ile Glu Arg Tyr Gly Val Gln Ile Phe
        500                 505                 510

Lys Ala Gly Val Thr Phe Leu Lys Thr Val Met Ser Asn Pro Gln Asn
    515                 520                 525

Val Glu Asp Val Arg Leu Tyr Asp Met His Ser Leu Arg Val Ala Thr
530                 535                 540

Phe Cys Ala Glu Pro Val Ser Pro Ala Val Gln Gln Phe Gly Met Gln
545                 550                 555                 560

Ile Met Thr Pro Gln Tyr Ile Asn Ser Tyr Trp Ala Thr Glu His Gly
                565                 570                 575

Gly Ile Val Trp Thr His Phe Tyr Gly Asn Gln Asp Phe Pro Leu Arg
                580                 585                 590

Pro Asp Ala His Thr Tyr Pro Leu Pro Trp Val Met Gly Asp Val Trp
            595                 600                 605

Val Ala Glu Thr Asp Glu Ser Gly Thr Thr Arg Tyr Arg Val Ala Asp
610                 615                 620

Phe Asp Glu Lys Gly Glu Ile Val Ile Thr Ala Pro Tyr Pro Tyr Leu
625                 630                 635                 640

Thr Arg Thr Leu Trp Gly Asp Val Pro Gly Phe Glu Ala Tyr Leu Arg
                645                 650                 655

Gly Glu Ile Pro Leu Arg Ala Trp Lys Gly Asp Ala Glu Arg Phe Val
            660                 665                 670

Lys Thr Tyr Trp Arg Arg Gly Pro Asn Gly Glu Trp Gly Tyr Ile Gln
            675                 680                 685

Gly Asp Phe Ala Ile Lys Tyr Pro Asp Gly Ser Phe Thr Leu His Gly
        690                 695                 700

Arg Ser Asp Asp Val Ile Asn Val Ser Gly His Arg Met Gly Thr Glu
705                 710                 715                 720

Glu Ile Glu Gly Ala Ile Leu Arg Asp Arg Gln Ile Thr Pro Asp Ser
            725                 730                 735

Pro Val Gly Asn Cys Ile Val Val Gly Ala Pro His Arg Glu Lys Gly
            740                 745                 750

Leu Thr Pro Val Ala Phe Ile Gln Pro Ala Pro Gly Arg His Leu Thr
        755                 760                 765

Gly Ala Asp Arg Arg Arg Leu Asp Glu Leu Val Arg Thr Glu Lys Gly
770                 775                 780

Ala Val Ser Val Pro Glu Asp Tyr Ile Glu Val Ser Ala Phe Pro Glu
785                 790                 795                 800

Thr Arg Ser Gly Lys Tyr Met Arg Arg Phe Leu Arg Asn Met Met Leu
                805                 810                 815

Asp Glu Pro Leu Gly Asp Thr Thr Leu Arg Asn Pro Glu Val Leu
            820                 825                 830

Glu Glu Ile Ala Ala Lys Ile Ala Glu Trp Lys Arg Arg Gln Arg Met
            835                 840                 845

Ala Glu Glu Gln Gln Ile Ile Glu Arg Tyr Arg Tyr Phe Arg Ile Glu
        850                 855                 860

Tyr His Pro Pro Thr Ala Ser Ala Gly Lys Leu Ala Val Val Thr Val
865                 870                 875                 880
```

```
Thr Asn Pro Pro Val Asn Ala Leu Asn Glu Arg Ala Leu Asp Glu Leu
            885                 890                 895

Asn Thr Ile Val Asp His Leu Ala Arg Arg Gln Asp Val Ala Ala Ile
        900                 905                 910

Val Phe Thr Gly Gln Gly Ala Arg Ser Phe Val Ala Gly Ala Asp Ile
        915                 920                 925

Arg Gln Leu Leu Glu Glu Ile His Thr Val Glu Glu Ala Met Ala Leu
    930                 935                 940

Pro Asn Asn Ala His Leu Ala Phe Arg Lys Ile Glu Arg Met Asn Lys
945                 950                 955                 960

Pro Cys Ile Ala Ala Ile Asn Gly Val Ala Leu Gly Gly Gly Leu Glu
            965                 970                 975

Phe Ala Met Ala Cys His Tyr Arg Val Ala Asp Val Tyr Ala Glu Phe
            980                 985                 990

Gly Gln Pro Glu Ile Asn Leu Arg Leu Leu Pro Gly Tyr Gly Gly Thr
            995                 1000                1005

Gln Arg Leu Pro Arg Leu Leu Tyr Lys Arg Asn Asn Gly Thr Gly
        1010                1015                1020

Leu Leu Arg Ala Leu Glu Met Ile Leu Gly Gly Arg Ser Val Pro
        1025                1030                1035

Ala Asp Glu Ala Leu Glu Leu Gly Leu Ile Asp Ala Ile Ala Thr
        1040                1045                1050

Gly Asp Gln Asp Ser Leu Ser Leu Ala Cys Ala Leu Ala Arg Ala
        1055                1060                1065

Ala Ile Gly Ala Asp Gly Gln Leu Ile Glu Ser Ala Ala Val Thr
        1070                1075                1080

Gln Ala Phe Arg His Arg His Glu Gln Leu Asp Glu Trp Arg Lys
        1085                1090                1095

Pro Asp Pro Arg Phe Ala Asp Glu Leu Arg Ser Ile Ile Ala
        1100                1105                1110

His Pro Arg Ile Glu Arg Ile Ile Arg Gln Ala His Thr Val Gly
        1115                1120                1125

Arg Asp Ala Ala Val His Arg Ala Leu Asp Ala Ile Arg Tyr Gly
        1130                1135                1140

Ile Ile His Gly Phe Glu Ala Gly Leu Glu His Glu Ala Lys Leu
        1145                1150                1155

Phe Ala Glu Ala Val Val Asp Pro Asn Gly Gly Lys Arg Gly Ile
        1160                1165                1170

Arg Glu Phe Leu Asp Arg Gln Ser Ala Pro Leu Pro Thr Arg Arg
        1175                1180                1185

Pro Leu Ile Thr Pro Glu Gln Glu Gln Leu Leu Arg Asp Gln Lys
        1190                1195                1200

Glu Leu Leu Pro Val Gly Ser Pro Phe Phe Pro Gly Val Asp Arg
        1205                1210                1215

Ile Pro Lys Trp Gln Tyr Ala Gln Ala Val Ile Arg Asp Pro Asp
        1220                1225                1230

Thr Gly Ala Ala Ala His Gly Asp Pro Ile Val Ala Glu Lys Gln
        1235                1240                1245

Ile Ile Val Pro Val Glu Arg Pro Arg Ala Asn Gln Ala Leu Ile
        1250                1255                1260

Tyr Val Leu Ala Ser Glu Val Asn Phe Asn Asp Ile Trp Ala Ile
        1265                1270                1275
```

-continued

```
Thr Gly Ile Pro Val Ser Arg Phe Asp Glu His Asp Arg Asp Trp
    1280               1285                1290

His Val Thr Gly Ser Gly Gly Ile Gly Leu Ile Val Ala Leu Gly
    1295               1300                1305

Glu Glu Ala Arg Arg Glu Gly Arg Leu Lys Val Gly Asp Leu Val
    1310               1315                1320

Ala Ile Tyr Ser Gly Gln Ser Asp Leu Leu Ser Pro Leu Met Gly
    1325               1330                1335

Leu Asp Pro Met Ala Ala Asp Phe Val Ile Gln Gly Asn Asp Thr
    1340               1345                1350

Pro Asp Gly Ser His Gln Gln Phe Met Leu Ala Gln Ala Pro Gln
    1355               1360                1365

Cys Leu Pro Ile Pro Thr Asp Met Ser Ile Glu Ala Ala Gly Ser
    1370               1375                1380

Tyr Ile Leu Asn Leu Gly Thr Ile Tyr Arg Ala Leu Phe Thr Thr
    1385               1390                1395

Leu Gln Ile Lys Ala Gly Arg Thr Ile Phe Ile Glu Gly Ala Ala
    1400               1405                1410

Thr Gly Thr Gly Leu Asp Ala Ala Arg Ser Ala Ala Arg Asn Gly
    1415               1420                1425

Leu Arg Val Ile Gly Met Val Ser Ser Ser Ser Arg Ala Ser Thr
    1430               1435                1440

Leu Leu Ala Ala Gly Ala His Gly Ala Ile Asn Arg Lys Asp Pro
    1445               1450                1455

Glu Val Ala Asp Cys Phe Thr Arg Val Pro Glu Asp Pro Ser Ala
    1460               1465                1470

Trp Ala Ala Trp Glu Ala Ala Gly Gln Pro Leu Leu Ala Met Phe
    1475               1480                1485

Arg Ala Gln Asn Asp Gly Arg Leu Ala Asp Tyr Val Val Ser His
    1490               1495                1500

Ala Gly Glu Thr Ala Phe Pro Arg Ser Phe Gln Leu Leu Gly Glu
    1505               1510                1515

Pro Arg Asp Gly His Ile Pro Thr Leu Thr Phe Tyr Gly Ala Thr
    1520               1525                1530

Ser Gly Tyr His Phe Thr Phe Leu Gly Lys Pro Gly Ser Ala Ser
    1535               1540                1545

Pro Thr Glu Met Leu Arg Arg Ala Asn Leu Arg Ala Gly Glu Ala
    1550               1555                1560

Val Leu Ile Tyr Tyr Gly Val Gly Ser Asp Asp Leu Val Asp Thr
    1565               1570                1575

Gly Gly Leu Glu Ala Ile Glu Ala Ala Arg Gln Met Gly Ala Arg
    1580               1585                1590

Ile Val Val Thr Val Ser Asp Ala Gln Arg Glu Phe Val Leu
    1595               1600                1605

Ser Leu Gly Phe Gly Ala Ala Leu Arg Gly Val Val Ser Leu Ala
    1610               1615                1620

Glu Leu Lys Arg Arg Phe Gly Asp Glu Phe Glu Trp Pro Arg Thr
    1625               1630                1635

Met Pro Pro Leu Pro Asn Ala Arg Gln Asp Pro Gln Gly Leu Lys
    1640               1645                1650

Glu Ala Val Arg Arg Phe Asn Asp Leu Val Phe Lys Pro Leu Gly
    1655               1660                1665
```

-continued

```
Ser Ala Val Gly Val Phe Leu Arg Ser Ala Asp Asn Pro Arg Gly
    1670            1675            1680

Tyr Pro Asp Leu Ile Ile Glu Arg Ala Ala His Asp Ala Leu Ala
    1685            1690            1695

Val Ser Ala Met Leu Ile Lys Pro Phe Thr Gly Arg Ile Val Tyr
    1700            1705            1710

Phe Glu Asp Ile Gly Gly Arg Arg Tyr Ser Phe Phe Ala Pro Gln
    1715            1720            1725

Ile Trp Val Arg Gln Arg Arg Ile Tyr Met Pro Thr Ala Gln Ile
    1730            1735            1740

Phe Gly Thr His Leu Ser Asn Ala Tyr Glu Ile Leu Arg Leu Asn
    1745            1750            1755

Asp Glu Ile Ser Ala Gly Leu Leu Thr Ile Thr Glu Pro Ala Val
    1760            1765            1770

Val Pro Trp Asp Glu Leu Pro Glu Ala His Gln Ala Met Trp Glu
    1775            1780            1785

Asn Arg His Thr Ala Ala Thr Tyr Val Val Asn His Ala Leu Pro
    1790            1795            1800

Arg Leu Gly Leu Lys Asn Arg Asp Glu Leu Tyr Glu Ala Trp Thr
    1805            1810            1815

Ala Gly Glu Arg
    1820
```

METHODS AND SYSTEMS FOR METHYLOTROPHIC PRODUCTION OF ORGANIC COMPOUNDS

CROSS REFERENCE TO RELATED APPLICATIONS

This application is a divisional application of U.S. application Ser. No. 14/649,973, filed Jun. 5, 2015, which is a U.S. national phase application of International Application No. PCT/US2013/073582 filed Dec. 6, 2013, which claims priority to and the benefit of U.S. Provisional Application No. 61/734,472 filed Dec. 7, 2012, the disclosure of each of which is incorporated by reference herein in its entirety.

STATEMENT REGARDING GOVERNMENT LICENSE RIGHTS

This invention was made with government support under contract number DE-AR0000091 awarded by U.S. Department of Energy, Office of ARPA-E. The government has certain rights in the invention.

SEQUENCE LISTING

The ASCII text file submitted electronically via EFS-Web, entitled "Sequence Listing.txt" created on Jun. 5, 2015, having a size of 24,930 bytes, is hereby incorporated by reference in its entirety.

TECHNICAL FIELD

The invention relates to systems, mechanisms and methods to confer production of carbon-based products to a methylotroph or a methylotrophic organism to efficiently convert C1 compounds into various carbon-based products, and in particular the use of such organism for the commercial production of various carbon-based products of interest. The invention also relates to systems, mechanisms and methods to confer additional and/or alternative pathways for energy conversion, methylotrophy and/or carbon fixation to a methylotroph.

BACKGROUND

Heterotrophs are biological organisms that utilize energy from organic compounds for growth and reproduction. Commercial production of various carbon-based products of interest generally relies on heterotrophic organisms that ferment sugar from crop biomass such as corn or sugarcane as their energy and carbon source [Bai, 2008]. An alternative to fermentation-based bio-production is the production of carbon-based products of interest from photosynthetic organisms, such as plants, algae and cyanobacteria, that derive their energy from sunlight and their carbon from carbon dioxide to support growth [U.S. Pat. No. 7,981,647]. However, the algae-based production of carbon-based products of interest relies on the relatively inefficient process of photosynthesis to supply the energy needed for production of organic compounds from carbon dioxide [Larkum, 2010]. Moreover, commercial production of carbon-based products of interest using photosynthetic organisms relies on reliable and consistent exposure to light to achieve the high productivities needed for economic feasibility; hence, photobioreactor design remains a significant technical challenge [Morweiser, 2010].

Methylotrophs are biological organisms that utilize energy and/or carbon from C1 compounds containing no carbon-carbon bonds such as formate, formic acid, formaldehyde, methanol, methane, halogenated methanes, and methylated sulfur species to produce all multi-carbon, organic compounds necessary for growth and reproduction. Most existing, naturally-occurring methylotrophs are poorly suited for industrial bio-processing and have therefore not demonstrated commercial viability for this purpose. Such organisms have long doubling times relative to industrialized heterotrophic organisms such as *Escherichia coli*, reflective of low total productivities. In addition, techniques for genetic manipulation (homologous recombination, transformation or transfection of nucleic acid molecules, and recombinant gene expression) are inefficient, time-consuming, laborious or non-existent.

Thus, a need exists to develop engineered and/or evolved methylotrops suitable for industrial uses. Accordingly, the ability to endow a methylotroph with biosynthetic capability to produce carbon-based products of interest, to grow the engineered and/or evolved methylotroph at the high cell densities needed for industrial bio-processing, and to efficiently provide the engineered organism with C1 compounds would significantly enable more energy- and carbon-efficient production of carbon-based products of interest. In addition, the ability to add one or more additional or alternative pathways for energy conversion, methylotrophy and/or carbon fixation capability to the methylotroph would enhance its ability to produce carbon-based products on interest.

SUMMARY

Systems and methods of the present invention provide for efficient production of renewable energy and other carbon-based products of interest (e.g., fuels, sugars, chemicals) from C1 compounds. Furthermore, systems and methods of the present invention can be used in the place of traditional methods of producing chemicals such as olefins (e.g., ethylene, propylene), which are traditionally derived from petroleum in a process that generates toxic by-products that are recognized as hazardous waste pollutants and harmful to the environment. As such, the present invention can additionally avoid the use of petroleum and the generation of such toxic by-products, and thus materially enhances the quality of the environment by contributing to the maintenance of basic life-sustaining natural elements such as air, water and/or soil by avoiding the generation of hazardous waste pollutants in the form of petroleum-derived by-products in the production of various chemicals.

In certain aspect, the invention described herein provides a methylotroph engineered to confer biosynthetic production of various carbon-based products of interest from C1 compounds. The engineered organism comprises one or more at least partially engineered carbon product biosynthetic pathways that convert central metabolites into desired products, such as carbon-based products of interest. Carbon-based products of interest include but are not limited to alcohols, fatty acids, fatty acid derivatives, fatty alcohols, fatty acid esters, wax esters, hydrocarbons, alkanes, polymers, fuels, commodity chemicals, specialty chemicals, carotenoids, isoprenoids, sugars, sugar phosphates, central metabolites, pharmaceuticals and pharmaceutical intermediates. For example, the carbon-based products of interest can include one or more of a sugar (for example, glucose, fructose, sucrose, xylose, lactose, maltose, pentose, rhamnose, galactose or arabinose), sugar phosphate (for example, glucose- 6-phosphate or fructose-6-phosphate), sugar alcohol (for example, sorbitol), sugar derivative (for example, ascorbate), alcohol (for example, ethanol, propanol, isopropanol or butanol), fermentative product (for example, ethanol, butanol, lactic acid, lactose or acetate), ethylene, propylene, 1-butene, 1,3-butadiene, acrylic acid, fatty acid (for example, co-cyclic fatty acid), fatty acid intermediate or derivative (for example, fatty acid alcohol, fatty acid ester, alkane, olegin or halogenated fatty acid), amino acid or intermediate (for example, lysine, glutamate, aspartate, shikimate, chorismate, phenylalanine, tyrosine, tryptophan), phenylpropanoid, isoprenoid (for example, hemiterpene, monoterpene, sesquiterpene, triterpene, tetraterpene, polyterpene, isoprene, bisabolene, myrcene, amorpha-4,11-diene, farnesene, taxadiene, squalene, lanosterol, β-carotene, ζ-carotene, lycopene, phytoene, limonene, or polyisoprene), glycerol, 1,3-propanediol, 1,4-butanediol, 1,3-butadiene, polyhydroxyalkanoate, polyhydroxybutyrate, lysine, γ-valerolactone, and acrylate. In some embodiments, the carbon-based products of interest can be carbon-based central metabolites.

The resulting engineered and/or evolved methylotroph of the invention is capable of efficiently synthesizing carbon-based products of interest from C1 compounds. The invention also provides carbon product biosynthetic pathways for conferring biosynthetic production of the carbon-based product of interest upon the host organism where the organism lacks the ability to efficiently produce carbon-based products of interest from C1 compounds. The invention also provides methods for introducing the carbon product biosynthetic pathways into the methylotroph. The invention also provides methods and media compositions for culturing the engineered and/or evolved methylotroph to support efficient methylotrophic production of carbon-based products of interest.

In various embodiments, the invention provides for the C1 compound serving as a source of both energy and carbon for the organism. In one embodiment, the C1 compound is soluble or miscible in water. For example, the C1 compound can be one or more of formate, formic acid, methanol and/or formaldehyde. C1 compounds that dissolve at high concentration or are miscible in water, in some instances, are preferable to less soluble or immiscible chemical species, such as methane, because mass transfer and uptake by the organism is more efficient. Similarly, soluble C1 compounds are preferable to molecular hydrogen, carbon dioxide or carbon monoxide, used in autotrophic production of carbon-based compounds (see, e.g., Example 7). In some embodiments, the C1 compound can be soluble in other solvents than water, depending on the composition of the media used for growing the organism. For example, the solubility of the C1 compound in the media may be enhanced by other components therein. In some embodiments, the C1 compound can be derived from electrolysis.

In certain embodiments, one or more of the following carbon product biosynthetic pathways can be used:
when said carbon product biosynthetic pathway is for fatty acid biosynthesis, said carbon product biosynthetic pathway includes one or more of: fatty acid synthase, acetyl-CoA carboxylase, fatty-acyl-CoA reductase, aldehyde decarbonylase, lipase, thioesterase and acyl-CoA synthase peptides; or
when said carbon product biosynthetic pathway is for branched chain fatty acid biosynthesis, said carbon product biosynthetic pathway includes one or more of: branched chain amino acid aminotransferase, branched chain α-ketoacid dehydrogenase, dihydrolipoyl dehydrogenase, beta-ketoacyl-ACP synthase, crotonyl-CoA reductase, isobutyryl-CoA mutase, β-ketoacyl-ACP synthase I, trans-2,cis-3-decenoyl-ACP isomerase and trans-2-enoyl-ACP reductase II; or
when said carbon product biosynthetic pathway is fatty alcohol biosynthesis, said carbon product biosynthetic pathway includes one or more of: fatty alcohol forming acyl-CoA reductase, fatty alcohol forming acyl-CoA reductase, alcohol dehydrogenase and alcohol reductase; or
when said carbon product biosynthetic pathway is for fatty ester biosynthesis, said carbon product biosynthetic pathway includes one or more of: alcohol O-acetyltransferase, wax synthase, fatty acid elongase, acyl-CoA reductase, acyltransferase, fatty acyl transferase, diacylglycerol acyltransferase, acyl-CoA was alcohol acyltransferase, bifunctional wax ester synthase/acyl-CoA:diacylglycerol acyltransferase, and β-ketoacyl-ACP synthase I; or
when said carbon product biosynthetic pathway is for alkane biosynthesis, said carbon product biosynthetic pathway includes one or more of: decarbonylase and terminal alcohol oxidoreductase; or
when said carbon product biosynthetic pathway is for co-cyclic fatty acid biosynthesis, said carbon product biosynthetic pathway includes one or more of: 1-cyclohexenylcarbonyl CoA reductase, 5-enopyruvylshikimate-3-phosphate synthase, acyl-CoA dehydrogenase, enoyl-(ACP) reductase, 2,4-dienoyl-CoA reductase, and acyl-CoA isomerase; or
when said carbon product biosynthetic pathway is for halogenated fatty acid biosynthesis, said carbon product biosynthetic pathway includes one or more of: fluorinase, nucleotide phosphorylase, fluorometabolite-specific aldolase, fluoroacetaldehyde dehydrogenase, and fluoroacetyl-CoA synthase; or
when said carbon product biosynthetic pathway is the deoxylylulose 5-phosphate (DXP) isoprenoid pathway, said carbon product biosynthetic pathway includes one or more of: 1-deoxy-D-xylulose-5-phosphate synthase, 1-deoxy-D-xylulose-5-phosphate reductoisomerase, 4-diphosphocytidyl-2C-methyl-D-erythritol synthase, 4-diphosphocytidyl-2C-methyl-D-erythritol kinase, 2C-methyl-D-erythritol 2,4-cyclodiphosphate synthase, (E)-4-hydroxy-3-methylbut-2-enyl diphosphate synthase, isopentyl/dimethylallyl diphosphate synthase and 4-hydroxy-3-methylbut-2-enyl diphosphate reductase; or
when said carbon product biosynthetic pathway is the mevalonate-dependent (MEV) isoprenoid pathway, said carbon product biosynthetic pathway includes one or more of: acetyl-CoA thiolase, HMG-CoA synthase, HMG-CoA reductase, mevalonate kinase, phosphomevalonate kinase, mevalonate pyrophosphate decarboxylase and isopentenyl pyrophosphate isomerase; or
when said carbon product biosynthetic pathway is the glycerol/1,3-propanediol biosynthesis pathway, said carbon product biosynthetic pathway includes one or more of: sn-glycerol-3-P dehydrogenase, sn-glycerol-3-phosphatase, glycerol dehydratase and 1,3-propanediol oxidoreductase; or
when said carbon product biosynthetic pathway is the 1,4-butanediol/1,3-butadiene biosynthesis pathway, said carbon product biosynthetic pathway includes one or more of: succinyl-CoA dehydrogenase, 4-hydroxybutyrate dehydrogenase, aldehyde dehydrogenase, 1,3-propanediol oxidoreductase and alcohol dehydratase; or when said carbon product biosynthetic pathway is the polyhydroxybutyrate biosynthesis pathway, said carbon product biosynthetic pathway includes one or more of: acetyl-CoA:acetyl-CoA C-acetyltransferase, (R)-3-hydroxyacyl-CoA:NADP$^+$ oxidoreductase and polyhydroxyalkanoate synthase; or when said carbon product biosynthetic pathway is the lysine biosynthesis pathway, said carbon product biosynthetic pathway includes one or more of: aspartate aminotransferase, aspartate kinase, aspartate semialdehyde dehydrogenase, dihydrodipicolinate synthase, dihydrodipicolinate reductase, tetrahydrodipicolinate succinylase, N-succinyldiaminopimelate-aminotransferase, N-succinyl-L-diaminopimelate desuccinylase, diaminopimelate epimerase, diaminopimelate decarboxylase, L,L-diaminopimelate aminotransferase, homocitrate synthase, homoaconitase, homoisocitrate dehydrogenase, 2-aminoadipate transaminase, 2-aminoadipate reductase, aminoadipate semialdehyde-glutamate reductase and lysine-2-oxoglutarate reductase; or when said carbon product biosynthetic pathway is the chorismate biosynthesis pathway, said carbon product biosynthetic pathway includes one or more of: 2-dehydro-3-deoxyphosphoheptonate aldolase, 3-dehydroquinate synthase, 3-dehydroquinate dehydratase, NADPH-dependent shikimate dehydrogenase, NAD(P)H-dependent shikimate dehydrogenase, shikimate kinase, 3-phosphoshikimate-1-carboxyvinyltransferase and chorismate synthase; or when said carbon product biosynthetic pathway is the phenylalanine biosynthesis pathway, said carbon product biosynthetic pathway includes one or more of: chorismate mutase, prephenate dehydratase and phenylalanine transaminase; or when said carbon product biosynthetic pathway is the tyrosine biosynthesis pathway, said carbon product biosynthetic pathway includes one or more of: chorismate mutase, prephenate dehydrogeanse and tyrosine aminotransferase; or when said carbon product biosynthetic pathway is the γ-valerolactone biosynthesis pathway, said carbon product biosynthetic pathway includes one or more of: propionyl-CoA synthase, beta-ketothiolase, acetoacetyl-CoA reductase, 3-hydroxybutyryl-CoA dehydratase, vinylacetyl-CoA Δ-isomerase, 4-hydroxybutyryl-CoA transferase and 1,4-lactonase; or when said carbon product biosynthetic pathway is the butanol biosynthesis pathway, said carbon product biosynthetic pathway includes one or more of: beta-ketothiolase, acetoacetyl-CoA reductase, 3-hydroxybutyryl-CoA dehydrogenase, enoyl-CoA hydratase, butyryl-CoA dehydrogenase, trans-enoyl-coenzyme A reductase, butyrate CoA-transferase, aldehyde dehydrogenase, alcohol dehydrogenase, acetyl-CoA acetyltransferase, β-hydroxybutyryl-CoA dehydrogenase, crotonase, butyryl CoA dehydrogenase, CoA-acylating aldehyde dehydrogenase and aldehyde-alcohol dehydrogenase; or when said carbon product biosynthetic pathway is the acrylate biosynthesis pathway, said carbon product biosynthetic pathway includes one or more of: enoyl-CoA hydratase, propionyl-CoA synthase and acrylate CoA-transferase.

In some embodiments, the 1-deoxy-D-xylulose-5-phosphate synthase can be encoded by SEQ ID NO: 1, or a homolog thereof having at least 80% sequence identity; or the isopentenyl pyrophosphate isomerase can be encoded by SEQ ID NO:2, or a homolog thereof having at least 80% sequence identity. In one embodiment, when said carbon product biosynthetic pathway is the isoprene biosynthesis pathway, said carbon product biosynthetic pathway can include isoprene synthase. The isoprene synthase can be encoded by SEQ ID NO:3, or a homolog thereof having at least 80% sequence identity. In another embodiment, when said carbon product biosynthetic pathway is the bisabolene biosynthesis pathway, said carbon product biosynthetic pathway can include E-alpha-bisabolene synthase. The E-alpha-bisabolene synthase can be encoded by SEQ ID NO:4, or a homolog thereof having at least 80% sequence identity.

In certain embodiments, the methylotrophic organism can be selected from the class Alphaproteobacterium. The methylotrophic organism may also be selected from the genus *Paracoccus*. For example, the methylotrophic organism can be *Paracoccus denitrificans, Paracoccus versutus* or *Paracoccus zeaxanthinifaciens*.

In some embodiments, the engineered cell can be further modified to have a less reduced growth rate on electrolytically generated C1 compound relative to non-evolved methylotrophic organism, or a substantially similar or enhanced growth rate on electrolytically generated C1 compound relative to non-electrolytically generated C1 compound. In certain embodiments, the engineered cell can be further evolved to have a less reduced growth rate on electrolytically generated C1 compound relative to non-evolved methylotrophic organism, or a substantially similar or enhanced growth rate on electrolytically generated C1 compound relative to non-electrolytically generated C1 compound.

In another aspect, an evolved methylotrophic organism is provided, having a less reduced growth rate on electrolytically generated C1 compound relative to non-evolved methylotrophic organism, or having a substantially similar or enhanced growth rate on electrolytically generated C1 compound relative to non-electrolytically generated C1 compound.

In a further aspect, a method for selecting an evolved methylotrophic organism having improved growth on a C1 compound is provided, comprising: incubating methylotrophic cells in a culture chamber with controlled temperature, cell concentration, and medium inflow and outflow rates, wherein the medium inflow includes a C1 compound; continuously monitoring a concentration of biomass in the culture chamber; and adjusting a flow rate of the C1 compound into the culture chamber so as to continually maintain an environment that selects for an improved growth rate. In some embodiments, the method can further include adjusting the medium inflow to be more permissive of growth or more suppressive of growth, so as to provide an adaptive environment to select for a fitness of the cells. In certain examples, the C1 compound can be formate. The C1 compound may be electrolytically generated. The C1 compound can be soluble in water.

In yet another aspect, a method of introducing a conjugative plasmid into methylotrophic host cells is provided, comprising: incubating a mixture of predetermined ratios of a donor culture and a recipient culture, at temperatures between 4° C. and 37° C. for between 1 and 48 hours, wherein the donor culture comprises a conjugal donor containing a conjugative plasmid having a first selectable trait, and the recipient culture comprises methylotrophic host cell having a second selectable trait; and subjecting the incubated mixture to a dually selective condition where only plasmid-containing transconjugants that have both the first selectable trait and the second selectable trait can grow, wherein the method does not include centrifugation or filtration of the mixture or incubated mixture. In some embodiments, the conjugal donor can be an *E. coli* strain such as *E. coli* S17-1, or an *E. coli* harboring plasmids such as pRK2013 or pRK2073, or any *E. coli* strain expressing a tra operon capable of mobilizing plasmids containing an RP4-derived sequence. The conjugal donor can be in a different species or genus of the host cell. In certain embodiments, the transconjugated plasmid contains an RP4 or similar mob element. In some embodiments, the host cell can be from the class Alphaproteobacterium or from the genus *Paracoccus*. For example, the host cell can be *Paracoccus denitrificans, Paracoccus versutus* or *Paracoccus zeaxanthinifaciens*.

A further aspect of the invention relates to a composition for bacterial culture, formulated to provide formate as the sole source of C1 compound and to enhance the growth of methylotrophic bacteria. The composition can contain between 0 and 160 mM sodium bicarbonate, between 0 and 16 mM sodium chloride, between 0 and 100 mM sodium nitrate, between 0 and 30 mM sodium thiosulfate, and initially containing between 5 and 100 mM of a formate salt, such as sodium formate or ammonium formate. For example, the composition can contain 100 mM sodium bicarbonate, 6 mM sodium chloride, 6 mM sodium nitrate, 11 mM sodium thiosulfate, and 26 mM sodium formate or ammonium formate. The composition can further include a basal minimal medium. In some embodiments, the basal minimal medium can be MOPS minimal medium, M9 minimal medium, R medium, M63 medium, or a medium substantially similar to any of the foregoing.

In yet another aspect, a composition of bacterial culture is provided, which is formulated to provide formate as the sole C1 compound and to enhance the growth of methylotrophic bacteria in a fed-batch bioreactor. The composition can include a medium initially charged in the fed-batch bioreactor which comprises R medium supplemented with between 1 and 100 micromolar sodium molybdate, between 10 and 1000 nanomolar sodium selenite, between 0.01 to 1 mg/L of thiamine, and between 0.001 to 1 mg/L of cobalamin. For example, the medium can contain between 5 and 20 micromolar sodium molybdate, between 50 and 200 nanomolar sodium selenite, between 0.05 to 2 mg/L of thiamine, and between 0.01 and 0.2 mg/L cobalamin. The composition can further include a feed composition supplied to the fed-batch bioreactor comprising a formate salt at supramolar concentration. The formate salt can be ammonium formate and/or sodium formate. The feed composition can further include a supramolar concentration of nitrate salt such as sodium nitrate. The nitrate salt and the formate salt can be provided in a molar ratio of 3.2:8, 3.0:8 or lower.

Also provided herein is a method for culturing methylotrophic bacteria, comprising incubating methylotrophic bacteria in any of the compositions described herein. In some embodiments, the incubating can be conducted aerobically. The incubating can take place in a fed-batch bioreactor. In some embodiments, a volumetric rate of C1 feedstock consumption in the fed-batch reactor can exceed 1.5 g*L$^{-1}$ hr$^{-1}$. In certain embodiments, the incubating can be conducted in the presence of a nitrate salt as electron acceptor and with a C1 feedstock as electron donor. In some embodiments, the C1 feedstock is a formate salt, such as sodium formate or ammonium formate. During incubation, the molar ratio of the nitrate salt to the formate salt can be kept below 3.2:8. The nitrate salt and the formate salt can be provided to the fed-batch bioreactor in a feed composition in supramolar concentrations in a molar ratio of 3.0:8 or lower. In some embodiments, the formate salt can be ammonium formate and/or sodium formate. The nitrate salt can be sodium nitrate.

In some aspects, growth of the methylotroph on C1 compounds can be augmented by the addition of additional and/or alternative pathways for energy conversion, methylotrophy and/or carbon fixation. Exemplary energy conversion pathways and carbon fixation pathways are described in U.S. Pat. No. 8,349,587, the entirety of which is hereby incorporated herein by reference.

DETAILED DESCRIPTION

Figure 1:
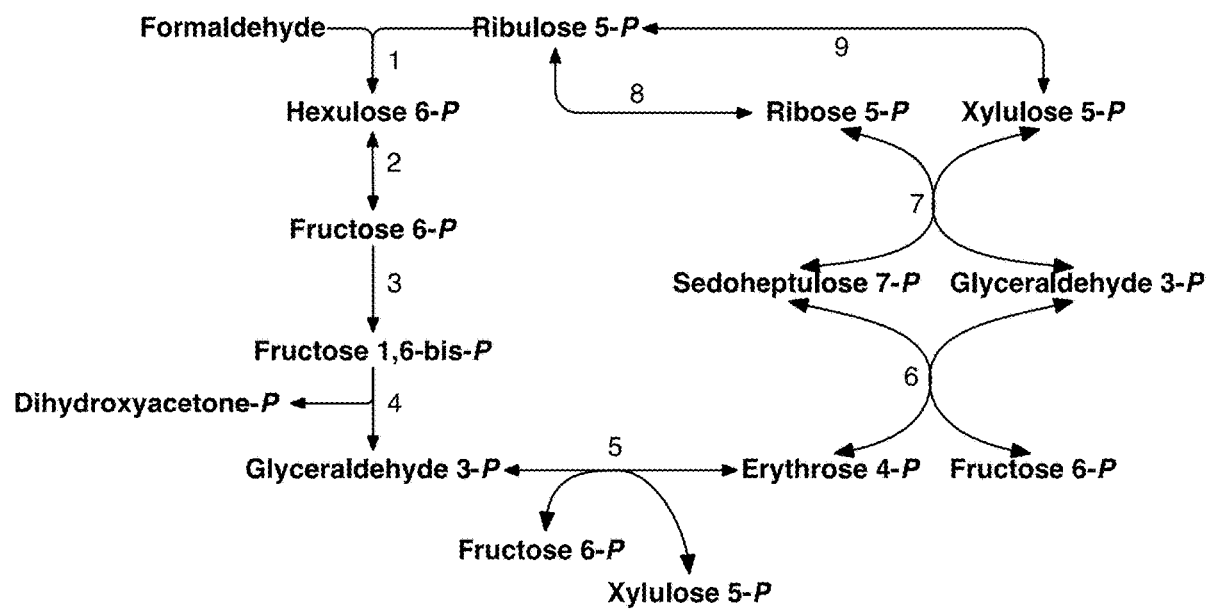
FIG. 1 depicts the metabolic reactions of the ribulose monophosphate cycle [Strom, 1974]. Some methylotrophic organisms such as *Methylococcus capsulatus* use this formaldehyde assimilation pathway to make the central metabolites needed for growth. In metabolite names, —P denotes phosphate. Each reaction is numbered. Enzymes catalyzing each reaction are as follows: 1, hexulose-6-phosphate synthase (E.C. 4.1.2.43); 2, 6-phospho-3-hexuloisomerase (E.C. 5.3.1.27); 3, phosphofructokinase (E.C. 2.7.1.11); 4, fructose bisphosphate aldolase (E.C. 4.1.2.13); 5, transketolase (E.C. 2.2.1.1); 6, transaldolase (E.C. 2.2.1.2); 7, transketolase (E.C. 2.2.1.1); 8, ribose 5-phosphate isomerase (E.C. 5.3.1.6); 9, ribulose-5-phosphate-3-epimerase (E.C. 5.1.3.1).

The present invention relates to developing and using engineered and/or evolved methylotrophs capable of utilizing C1 compounds to produce a desired product. The invention provides for the engineering of a methylotroph, for example, *Paracoccus denitrificans, Paracoccus versutus* or *Paracoccus zeaxanthinifaciens*, or other organism suitable for commercial large-scale production of fuels and chemicals, that can efficiently utilize C1 compounds as a substrate for growth and for chemical production provides cost-advantaged processes for manufacturing of carbon based products of interest. The organisms can be optimized and tested rapidly and at reasonable costs. The invention further provides for the engineering of a methylotroph to include one or more additional or alternative pathways for utilization of C1 compounds to produce central metabolites for growth and/or other desired products.

C1 compounds represent an alternative feedstock to sugar or light plus carbon dioxide for the production of carbon-based products of interest. There exist non-biological routes to convert C1 compounds to chemicals and fuels of interest. For example, the Fischer-Tropsch process consumes carbon monoxide and hydrogen gas generated from gasification of coal or biomass to produce methanol or mixed hydrocarbons as fuels [U.S. Pat. No. 1,746,464]. The drawbacks of Fischer-Tropsch processes are: 1) a lack of product selectivity, which results in difficulties separating desired products; 2) catalyst sensitivity to poisoning; 3) high energy costs due to high temperatures and pressures required; and 4) the limited range of products available at commercially competitive costs. Without the advent of carbon sequestration technologies that can operate at scale, the Fischer-Tropsch process is widely considered to be an environmentally costly method for generating liquid fuels. Alternatively, processes that rely on naturally occurring microbes that convert synthesis gas or syngas, a mixture of primarily molecular hydrogen and carbon monoxide that can be obtained via gasification of any organic feedstock, such as coal, coal oil, natural gas, biomass, or waste organic matter, to products such as ethanol, acetate, methane, or molecular hydrogen are available [Henstra, 2007]. However, these naturally occurring microbes can produce only a very restricted set of products, are limited in their efficiencies, lack established tools for genetic manipulation, and are sensitive to their end products at high concentrations. Finally, there is some work to introduce syngas utilization into industrial microbial hosts [U.S. Pat. No. 7,803,589]; however, these processes have yet to be demonstrated at commercial scale and are limited to using syngas as the feedstock.

The present invention provides, in some aspects, engineered or evolved methylotrophic organisms that are advantageous and/or suitable for industrial uses. The invention also provides a source of renewable energy. In some embodiments, the invention provides for the use of a C1 compound, such as formate, formic acid, formaldehyde, methanol or any combination thereof. In one embodiment, the C1 compound can be derived from electrolysis. There is tremendous commercial activity towards the goal of renewable and/or carbon-neutral energy from solar voltaic, geothermal, wind, nuclear, hydroelectric and more. However, most of these technologies produce electricity and are thus limited in use to the electrical grid [Whipple, 2010]. Furthermore, at least some of these renewable energy sources such as solar and wind suffer from being intermittent and unreliable. The lack of practical, large scale electricity storage technologies limits how much of the electricity demand can be shifted to renewable sources. The ability to store electrical energy in chemical form, such as in carbon-based products of interest, would both offer a means for large-scale electricity storage and allow renewable electricity to meet energy demand from the transportation sector. Renewable electricity combined with electrolysis, such as the electrochemical production of formate/formic acid from carbon dioxide [for example, WO/2007/041872] or formaldehyde or methanol from carbon dioxide [for example, WO/2010/088524, WO/2012/015909, WO/2012/015905], opens the possibility of a sustainable, renewable supply of the C1 compound as one aspect of the present invention.

In some embodiments, the invention provides for the use of a C1 compound, such as formaldehyde and/or methanol, derived from waste streams. For example, formaldehyde is an oxidation product of methanol or methane. Methanol can be prepared from synthesis gas (the major product of gasification of coal, coal oil, natural gas, and of carbonaceous materials such as biomass materials, including agricultural crops and residues, and waste organic matter) or reductive conversion of carbon dioxide and hydrogen by chemical synthetic processes. Methane is a major component of natural gas and can also be obtained from renewable biomass.

The invention provides for the expression of one or more exogenous proteins or enzymes in the host cell, thereby conferring biosynthetic pathway(s) to utilize central metabolites to produce reduced organic compounds. The engineered cell can also be endowed with one or more carbon product biosynthetic pathways that convert central metabolites into desired products, such as carbon-based products of interest.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art would understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well-known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

Definitions

As used herein, the terms "nucleic acids," "nucleic acid molecule" and "polynucleotide" may be used interchangeably and include both single-stranded (ss) and double-stranded (ds) RNA, DNA and RNA:DNA hybrids. As used herein the terms "nucleic acid", "nucleic acid molecule", "polynucleotide", "oligonucleotide", "oligomer" and "oligo" are used interchangeably and are intended to include, but are not limited to, a polymeric form of nucleotides that may have various lengths, including either deoxyribonucleotides or ribonucleotides, or analogs thereof. For example, oligos may be from 5 to about 200 nucleotides, from 10 to about 100 nucleotides, or from 30 to about 50 nucleotides long. However, shorter or longer oligonucleotides may be used. Oligos for use in the present invention can be fully designed. A nucleic acid molecule may encode a full-length polypeptide or a fragment of any length thereof, or may be non-coding.

Nucleic acids can refer to naturally-occurring or synthetic polymeric forms of nucleotides. The oligos and nucleic acid molecules of the present invention may be formed from naturally-occurring nucleotides, for example forming deoxyribonucleic acid (DNA) or ribonucleic acid (RNA) molecules. Alternatively, the naturally-occurring oligonucleotides may include structural modifications to alter their properties, such as in peptide nucleic acids (PNA) or in locked nucleic acids (LNA). The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. Modifications can also include phosphorothioated bases for increased stability.

Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the nucleotide comparison methods and algorithms set forth below, or as defined as being capable of hybridizing to the polynucleotides that encode the protein sequences.

As used herein, the term "gene" refers to a nucleic acid that contains information necessary for expression of a polypeptide, protein, or untranslated RNA (e.g., rRNA, tRNA, anti-sense RNA). When the gene encodes a protein, it includes the promoter and the structural gene open reading frame sequence (ORF), as well as other sequences involved in expression of the protein. When the gene encodes an untranslated RNA, it includes the promoter and the nucleic acid that encodes the untranslated RNA.

As used herein, the term "genome" refers to the whole hereditary information of an organism that is encoded in the DNA (or RNA for certain viral species) including both coding and non-coding sequences. In various embodiments, the term may include the chromosomal DNA of an organism and/or DNA that is contained in an organelle such as, for example, the mitochondria or chloroplasts and/or extrachromosomal plasmid and/or artificial chromosome. A "native gene" or "endogenous gene" refers to a gene that is native to the host cell with its own regulatory sequences whereas an "exogenous gene" or "heterologous gene" refers to any gene that is not a native gene, comprising regulatory and/or coding sequences that are not native to the host cell. In some embodiments, a heterologous gene may comprise mutated sequences or part of regulatory and/or coding sequences. In some embodiments, the regulatory sequences may be heterologous or homologous to a gene of interest. A heterologous regulatory sequence does not function in nature to regulate the same gene(s) it is regulating in the transformed host cell. "Coding sequence" refers to a DNA sequence coding for a specific amino acid sequence. As used herein, "regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, ribosome binding sites, translation leader sequences, RNA processing site, effector (e.g., activator, repressor) binding sites, stem-loop structures, and so on.

As described herein, a genetic element may be any coding or non-coding nucleic acid sequence. In some embodiments, a genetic element is a nucleic acid that codes for an amino acid, a peptide or a protein. Genetic elements may be operons, genes, gene fragments, promoters, exons, introns, regulatory sequences, or any combination thereof. Genetic elements can be as short as one or a few codons or may be longer including functional components (e.g. encoding proteins) and/or regulatory components. In some embodiments, a genetic element includes an entire open reading frame of a protein, or the entire open reading frame and one or more (or all) regulatory sequences associated therewith. One skilled in the art would appreciate that the genetic elements can be viewed as modular genetic elements or genetic modules. For example, a genetic module can comprise a regulatory sequence or a promoter or a coding sequence or any combination thereof. In some embodiments, the genetic element includes at least two different genetic modules and at least two recombination sites. In eukaryotes, the genetic element can comprise at least three modules. For example, a genetic module can be a regulator sequence or a promoter, a coding sequence, and a polyadenlylation tail or any combination thereof. In addition to the promoter and the coding sequences, the nucleic acid sequence may comprises control modules including, but not limited to a leader, a signal sequence and a transcription terminator. The leader sequence is a non-translated region operably linked to the 5' terminus of the coding nucleic acid sequence. The signal peptide sequence codes for an amino acid sequence linked to the amino terminus of the polypeptide which directs the polypeptide into the cell's secretion pathway.

As generally understood, a codon is a series of three nucleotides (triplets) that encodes a specific amino acid residue in a polypeptide chain or for the termination of translation (stop codons). There are 64 different codons (61 codons encoding for amino acids plus 3 stop codons) but only 20 different translated amino acids. The overabundance in the number of codons allows many amino acids to be encoded by more than one codon. Different organisms (and organelles) often show particular preferences or biases for one of the several codons that encode the same amino acid. The relative frequency of codon usage thus varies depending on the organism and organelle. In some instances, when expressing a heterologous gene in a host organism, it is desirable to modify the gene sequence so as to adapt to the codons used and codon usage frequency in the host. In particular, for reliable expression of heterologous genes it may be preferred to use codons that correlate with the host's tRNA level, especially the tRNA's that remain charged during starvation. In addition, codons having rare cognate tRNA's may affect protein folding and translation rate, and thus, may also be used. Genes designed in accordance with codon usage bias and relative tRNA abundance of the host are often referred to as being "optimized" for codon usage, which has been shown to increase expression level. Optimal codons also help to achieve faster translation rates and high accuracy. In general, codon optimization involves silent mutations that do not result in a change to the amino acid sequence of a protein.

Genetic elements or genetic modules may derive from the genome of natural organisms or from synthetic polynucleotides or from a combination thereof. In some embodiments, the genetic elements modules derive from different organisms. Genetic elements or modules useful for the methods described herein may be obtained from a variety of sources such as, for example, DNA libraries, BAC (bacterial artificial chromosome) libraries, de novo chemical synthesis, or excision and modification of a genomic segment. The sequences obtained from such sources may then be modified using standard molecular biology and/or recombinant DNA technology to produce polynucleotide constructs having desired modifications for reintroduction into, or construction of, a large product nucleic acid, including a modified, partially synthetic or fully synthetic genome. Exemplary methods for modification of polynucleotide sequences obtained from a genome or library include, for example, site directed mutagenesis; PCR mutagenesis; inserting, deleting or swapping portions of a sequence using restriction enzymes optionally in combination with ligation; in vitro or in vivo homologous recombination; and site-specific recombination; or various combinations thereof. In other embodiments, the genetic sequences useful in accordance with the methods described herein may be synthetic oligonucleotides or polynucleotides. Synthetic oligonucleotides or polynucleotides may be produced using a variety of methods known in the art.

In some embodiments, genetic elements share less than 99%, less than 95%, less than 90%, less than 80%, less than 70% sequence identity with a native or natural nucleic acid sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for alignment are described [Doolittle, 1996]. Preferably, an alignment program that permits gaps in the sequence is utilized to align the sequences. The Smith-Waterman is one type of algorithm that permits gaps in sequence alignments [Shpaer, 1997]. Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer.

As used herein, an "ortholog" is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor. Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art would understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, as used herein, "paralogs" are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

As used herein, a "nonorthologous gene displacement" is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement may be identifiable as structurally related to a known gene encoding the referenced function, less structurally related but functionally similar genes and their corresponding gene products nevertheless still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Orthologs, paralogs and nonorthologous gene displacements can be determined by methods well known to those skilled in the art. For example, inspection of nucleic acid or amino acid sequences for two polypeptides can reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences. Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art would know what modifications can be made to the above parameters to either increase or decrease the stringency of the comparison, for example, and determine the relatedness of two or more sequences.

As used herein, the term "homolog" refers to any ortholog, paralog, nonorthologous gene, or similar gene encoding an enzyme catalyzing a similar or substantially similar metabolic reaction, whether from the same or different species.

As used herein, the phrase "homologous recombination" refers to the process in which nucleic acid molecules with similar nucleotide sequences associate and exchange nucleotide strands. A nucleotide sequence of a first nucleic acid molecule that is effective for engaging in homologous recombination at a predefined position of a second nucleic acid molecule can therefore have a nucleotide sequence that facilitates the exchange of nucleotide strands between the first nucleic acid molecule and a defined position of the second nucleic acid molecule. Thus, the first nucleic acid can generally have a nucleotide sequence that is sufficiently complementary to a portion of the second nucleic acid molecule to promote nucleotide base pairing. Homologous recombination requires homologous sequences in the two recombining partner nucleic acids but does not require any specific sequences. Homologous recombination can be used to introduce a heterologous nucleic acid and/or mutations into the host genome. Such systems typically rely on sequence flanking the heterologous nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

It should be appreciated that the nucleic acid sequence of interest or the gene of interest may be derived from the genome of natural organisms. In some embodiments, genes of interest may be excised from the genome of a natural organism or from the host genome, for example E. coli. It has been shown that it is possible to excise large genomic fragments by in vitro enzymatic excision and in vivo excision and amplification. For example, the FLP/FRT site specific recombination system and the Cre/loxP site specific recombination systems have been efficiently used for excision large genomic fragments for the purpose of sequencing [Yoon, 1998]. In some embodiments, excision and amplification techniques can be used to facilitate artificial genome or chromosome assembly. Genomic fragments may be excised from the chromosome of a methylotroph and altered before being inserted into the host cell artificial genome or chromosome. In some embodiments, the excised genomic fragments can be assembled with engineered promoters and/or other gene expression elements and inserted into the genome of the host cell.

As used herein, the term "polypeptide" refers to a sequence of contiguous amino acids of any length. The terms "peptide," "oligopeptide," "protein" or "enzyme" may be used interchangeably herein with the term "polypeptide". In certain instances, "enzyme" refers to a protein having catalytic activities.

A "proteome" is the entire set of proteins expressed by a genome, cell, tissue or organism. More specifically, it is the set of expressed proteins in a given type of cells or an organism at a given time under defined conditions. Transcriptome is the set of all RNA molecules, including mRNA, rRNA, tRNA, and other non-coding RNA produced in one or a population of cells. Metabolome refers to the complete set of small-molecule metabolites (such as metabolic intermediates, hormones and other signaling molecules, and secondary metabolites) to be found within a biological sample, such as a single organism.

The term "fuse," "fused" or "link" refers to the covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

As used herein, unless otherwise stated, the term "transcription" refers to the synthesis of RNA from a DNA template; the term "translation" refers to the synthesis of a polypeptide from an mRNA template. Translation in general is regulated by the sequence and structure of the 5' untranslated region (5'-UTR) of the mRNA transcript. One regulatory sequence is the ribosome binding site (RBS), which promotes efficient and accurate translation of mRNA. The prokaryotic RBS is the Shine-Dalgamo sequence, a purine-rich sequence of 5'-UTR that is complementary to the UCCU core sequence of the 3'-end of 16S rRNA (located within the 30S small ribosomal subunit). Various Shine-Dalgamo sequences have been found in prokaryotic mRNAs and generally lie about 10 nucleotides upstream from the AUG start codon. Activity of a RBS can be influenced by the length and nucleotide composition of the spacer separating the RBS and the initiator AUG. In eukaryotes, the Kozak sequence A/GCCACCAUGG, which lies within a short 5' untranslated region, directs translation of mRNA. An mRNA lacking the Kozak consensus sequence may also be translated efficiently in an in vitro systems if it possesses a moderately long 5'-UTR that lacks stable secondary structure. While E. coli ribosome preferentially recognizes the Shine-Dalgamo sequence, eukaryotic ribosomes (such as those found in retic lysate) can efficiently use either the Shine-Dalgamo or the Kozak ribosomal binding sites.

As used herein, the terms "promoter," "promoter element," or "promoter sequence" refer to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

One should appreciate that promoters have modular architecture and that the modular architecture may be altered. Bacterial promoters typically include a core promoter element and additional promoter elements. The core promoter refers to the minimal portion of the promoter required to initiate transcription. A core promoter includes a Transcription Start Site, a binding site for RNA polymerases and general transcription factor binding sites. The "transcription start site" refers to the first nucleotide to be transcribed and is designated +1. Nucleotides downstream the start site are numbered +1, +2, etc., and nucleotides upstream the start site are numbered −1, −2, etc. Additional promoter elements are located 5' (i.e., typically 30-250 bp upstream of the start site) of the core promoter and regulate the frequency of the transcription. The proximal promoter elements and the distal promoter elements constitute specific transcription factor site. In prokaryotes, a core promoter usually includes two consensus sequences, a −10 sequence or a −35 sequence, which are recognized by sigma factors (see, for example, [Hawley, 1983]). The −10 sequence (10 bp upstream from the first transcribed nucleotide) is typically about 6 nucleotides in length and is typically made up of the nucleotides adenosine and thymidine (also known as the Pribnow box). In some embodiments, the nucleotide sequence of the −10 sequence is 5'-TATAAT or may comprise 3 to 6 bases pairs of the consensus sequence. The presence of this box is essential to the start of the transcription. The −35 sequence of a core promoter is typically about 6 nucleotides in length. The nucleotide sequence of the −35 sequence is typically made up of the each of the four nucleosides. The presence of this sequence allows a very high transcription rate. In some embodiments, the nucleotide sequence of the −35 sequence is 5'-TTGACA or may comprise 3 to 6 bases pairs of the consensus sequence. In some embodiments, the −10 and the −35 sequences are spaced by about 17 nucleotides. Eukaryotic promoters are more diverse than prokaryotic promoters and may be located several kilobases upstream of the transcription starting site. Some eukaryotic promoters contain a TATA box (e.g. containing the consensus sequence TATAAA or part thereof), which is located typically within 40 to 120 bases of the transcriptional start site. One or more upstream activation sequences (UAS), which are recognized by specific binding proteins can act as activators of the transcription. Theses UAS sequences are typically found upstream of the transcription initiation site. The distance between the UAS sequences and the TATA box is highly variable and may be up to 1 kb.

As used herein, the term "vector" refers to any genetic element, such as a plasmid, phage, transposon, cosmid, chromosome, artificial chromosome, episome, virus, virion, etc., capable of replication when associated with the proper control elements and which can transfer gene sequences into or between cells. The vector may contain a marker suitable for use in the identification of transformed or transfected cells. For example, markers may provide antibiotic resistant, fluorescent, enzymatic, as well as other traits. As a second example, markers may complement auxotrophic deficiencies or supply critical nutrients not in the culture media. Types of vectors include cloning and expression vectors. As used herein, the term "cloning vector" refers to a plasmid or phage DNA or other DNA sequence which is able to replicate autonomously in a host cell and which is characterized by one or a small number of restriction endonuclease recognition sites and/or sites for site-specific recombination. A foreign DNA fragment may be spliced into the vector at these sites in order to bring about the replication and cloning of the fragment. The term "expression vector" refers to a vector which is capable of expressing of a gene that has been cloned into it. Such expression can occur after transformation into a host cell, or in IVPS systems. The cloned DNA is usually operably linked to one or more regulatory sequences, such as promoters, activator/repressor binding sites, terminators, enhancers and the like. The promoter sequences can be constitutive, inducible and/or repressible.

As used herein, the term "host" or "host cell" refers to any prokaryotic or eukaryotic (e.g., mammalian, insect, yeast, plant, bacterial, archaeal, avian, animal, etc.) cell or organism. The host cell can be a recipient of a replicable expression vector, cloning vector or any heterologous nucleic acid molecule. In an embodiment, the host cell is a methylotroph (e.g., naturally existing or genetically engineered or metabolically evolved). Host cells may be prokaryotic cells such as species of the genus *Paracoccus* and *Escherichia*, or eukaryotic cells such as yeast, insect, amphibian, or mammalian cells or cell lines. Cell lines refer to specific cells that can grow indefinitely given the appropriate medium and conditions. Cell lines can be mammalian cell lines, insect cell lines or plant cell lines. Exemplary cell lines can include tumor cell lines and stem cell lines. The heterologous nucleic acid molecule may contain, but is not limited to, a sequence of interest, a transcriptional regulatory sequence (such as a promoter, enhancer, repressor, and the like) and/or an origin of replication. As used herein, the terms "host," "host cell," "recombinant host" and "recombinant host cell" may be used interchangeably. For examples of such hosts, see [Sambrook, 2001].

One or more nucleic acid sequences can be targeted for delivery to target prokaryotic or eukaryotic cells via conventional transformation or transfection techniques. As used herein, the terms "transformation" and "transfection" are intended to refer to a variety of art-recognized techniques for introducing an exogenous nucleic acid sequence (e.g., DNA) into a target cell, including calcium phosphate or calcium chloride co-precipitation, DEAE-dextran-mediated transfection, lipofection, conjugation, electroporation, optoporation, injection and the like. Suitable transformation or transfection media include, but are not limited to, water, $CaCl_2$, cationic polymers, lipids, and the like. Suitable materials and methods for transforming or transfecting target cells can be found in [Sambrook, 2001], and other laboratory manuals. In certain instances, oligo concentrations of about 0.1 to about 0.5 micromolar (per oligo) can be used for transformation or transfection.

As used herein, the term "marker" or "reporter" refers to a gene or protein that can be attached to a regulatory sequence of another gene or protein of interest, so that upon expression in a host cell or organism, the reporter can confer certain characteristics that can be relatively easily selected, identified and/or measured. Reporter genes are often used as an indication of whether a certain gene has been introduced into or expressed in the host cell or organism. Examples of commonly used reporters include: antibiotic resistance genes, auxotropic markers, β-galactosidase (encoded by the bacterial gene lacZ), luciferase (from lightning bugs), chloramphenicol acetyltransferase (CAT; from bacteria), GUS (β-glucuronidase; commonly used in plants) and green fluorescent protein (GFP; from jelly fish). Reporters or markers can be selectable or screenable. A selectable marker (e.g., antibiotic resistance gene, auxotropic marker) is a gene confers a trait suitable for artificial selection; typically host cells expressing the selectable marker is protected from a selective agent that is toxic or inhibitory to cell growth. A screenable marker (e.g., gfp, lacZ) generally allows researchers to distinguish between wanted cells (expressing the marker) and unwanted cells (not expressing the marker or expressing at insufficient level).

Figure 2:
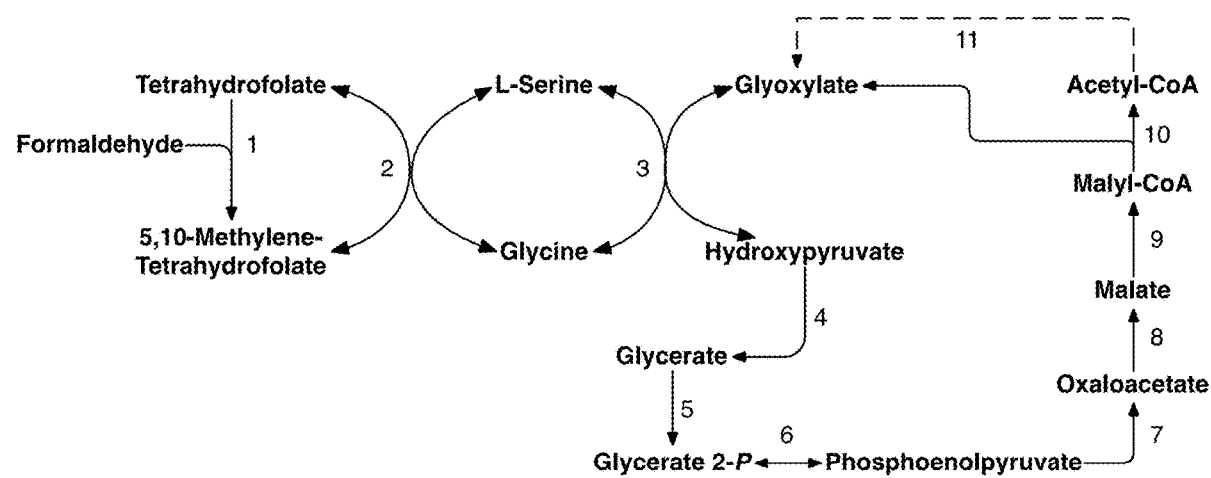
FIG. 2 depicts the metabolic reactions of the serine cycle. Some methyltrophic organisms such as *Hyphomicrobium methylovorum* GM2, *Hyphomicrobium zavarzinii* ZV580, *Methylobacterium extorquens* AM1, *Methylobacterium organophilum, Methylocystis parvus, Methylosinus sporium* and *Methylosinus trichosporium* use this formaldehyde assimilation pathway to make the central metabolites needed for growth. In metabolite names, —P denotes phosphate and -CoA denotes coenzyme A. Enzymes catalyzing each reaction are as follows: 1, spontaneous reaction; 2, serine hydroxymethyltransferase (E.C. 2.1.2.1); 3, serine-glyoxylate aminotransferase (E.C. 2.6.1.45); 4, hydroxypyruvate reductase (E.C. 1.1.1.81); 5, glycerate 2-kinase (E.C. 2.7.1.165); 6, enolase (E.C. 4.2.1.11); 7, phosphoenolpyruvate carboxylase (E.C. 4.1.1.31); 8, malate dehydrogenase (E.C. 1.1.1.37); 9, malate thiokinase (E.C. 6.2.1.9); 10, malyl-CoAlyase (E.C. 4.1.3.24); 11, the glyoxylate regeneration pathway.
Figure 3:
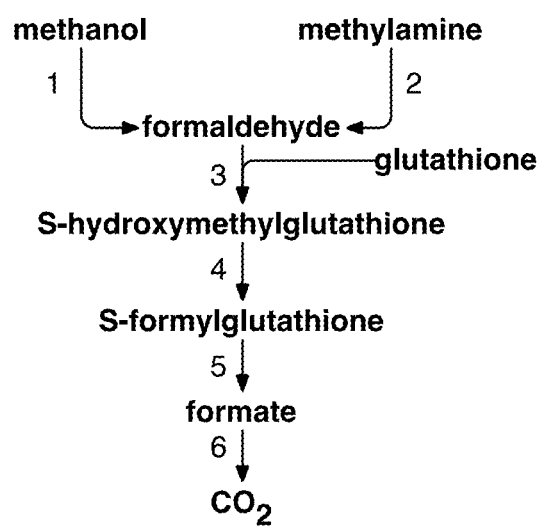
FIG. 3 depicts the metabolic reactions of energy conversion pathway(s) that oxidize C1 compounds in some methylotrophic organisms such as *Paracoccus* species. Each reaction is numbered. Enzymes catalyzing each reaction are as follows: 1, methanol dehydrogenase (E.C. 1.1.2.7); 2, methylamine dehydrogenase (E.C. 1.4.9.1); 3, S-(hydroxymethyl) glutathione synthase (E.C. 4.4.1.22); 4, NAD- and glutathione-dependent formaldehyde dehydrogenase (E.C. 1.1.1.284); 5, S-formylglutathione hydrolase (E.C. 3.1.2.12); 6, formate dehydrogenase (E.C. 1.2.1.2).
Figure 4:
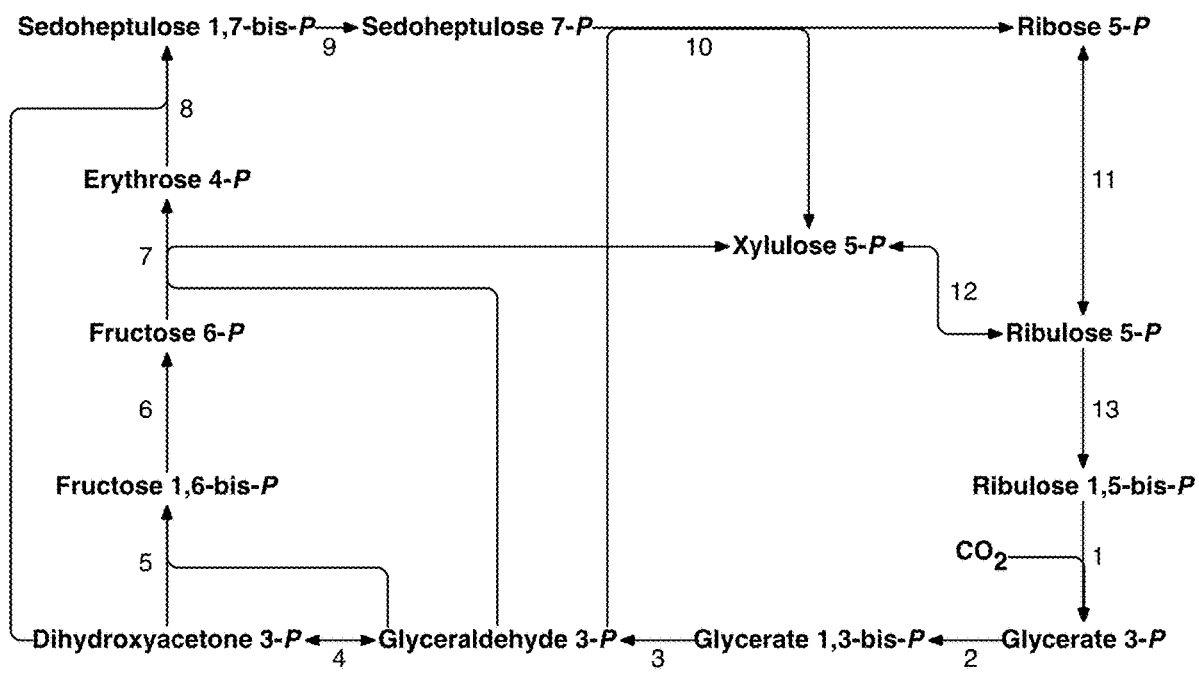
FIG. 4 depicts the metabolic reactions of the Calvin-Benson-Bassham cycle or the reductive pentose phosphate (RPP) cycle [Bassham, 1954]. Some methylotrophic organisms such as *Paracoccus* species use this carbon fixation pathway to reduce carbon dioxide to central metabolites needed for growth. In metabolite names, —P denotes phosphate. Each reaction is numbered. Enzymes catalyzing each reaction are as follows: 1, ribulose bisphosphate carboxylase (E.C. 4.1.1.39); 2, phosphoglycerate kinase (E.C. 2.7.2.3); 3, glyceraldehyde-3P dehydrogenase (phosphorylating) (E.C. 1.2.1.12 or E.C. 1.2.1.13); 4, triose-phosphate isomerase (E.C. 5.3.1.1); 5, fructose-bisphosphate aldolase (E.C. 4.1.2.13); 6, fructose-bisphosphatase (E.C. 3.1.3.11); 7, transketolase (E.C. 2.2.1.1); 8, sedoheptulose-1,7-bisphosphate aldolase (E.C. 4.1.2.-); 9, sedoheptulose bisphosphatase (E.C. 3.1.3.37); 10, transketolase (E.C. 2.2.1.1); 11, ribose-5-phosphate isomerase (E.C. 5.3.1.6); 12, ribulose-5-phosphate-3-epimerase (E.C. 5.1.3.1); 13, phosphoribulokinase (E.C. 2.7.1.19).
Figure 5:
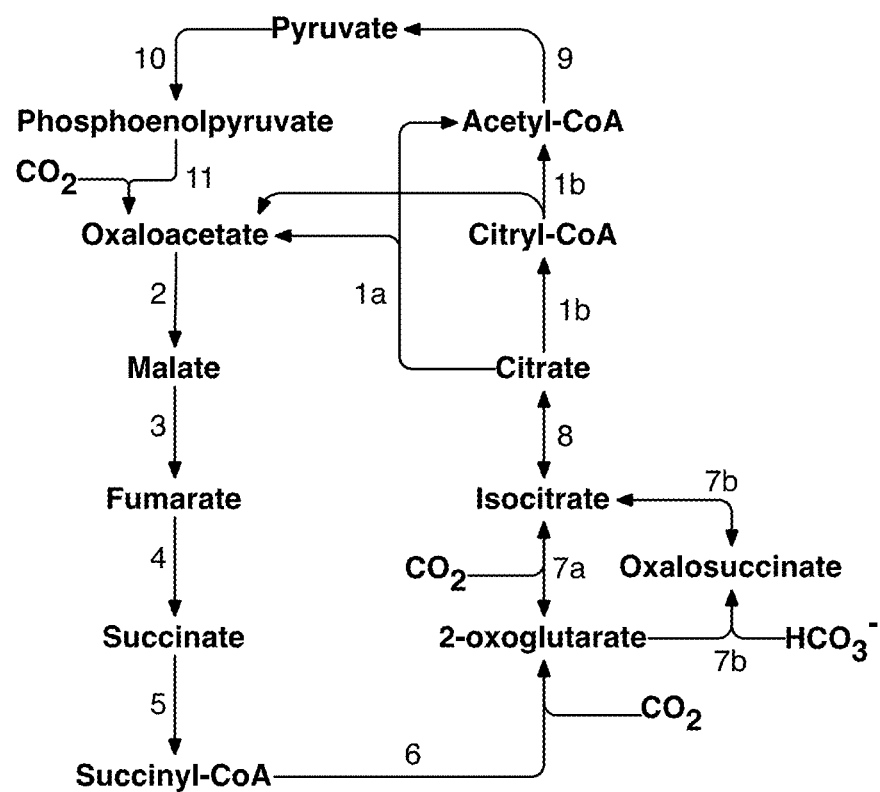
FIG. 5 depicts the metabolic reactions of the reductive tricarboxylic acid cycle [Evans, 1966; Buchanan, 1990; Hügler, 2011]. Some methylotrophic organisms such as *Nautilia* sp. strain AmN use this carbon fixation pathway to reduce carbon dioxide to central metabolites needed for growth. Each reaction is numbered. For certain reactions, such as reaction 1 and 7, there are two possible routes denoted by a and b, each of which is catalyzed by different enzyme(s). Enzymes catalyzing each reaction are as follows: 1a, ATP citrate lyase (E.C. 2.3.3.8); 1b, citryl-CoA synthetase (E.C. 6.2.1.18) and citryl-CoA lyase (E.C. 4.1.3.34); 2, malate dehydrogenase (E.C. 1.1.1.37); 3, fumarate dehydratase or fumarase (E.C. 4.2.1.2); 4, fumarate reductase (E.C. 1.3.99.1); 5, succinyl-CoA synthetase (E.C. 6.2.1.5); 6, 2-oxoglutarate synthase or 2-oxoglutarate:ferredoxin oxidoreductase (E.C. 1.2.7.3); 7a, isocitrate dehydrogenase (E.C. 1.1.1.41 or E.C. 1.1.1.42); 7b, 2-oxoglutarate carboxylase (E.C. 6.4.1.7) and oxalosuccinate reductase (E.C. 1.1.1.41); 8, aconitate hydratase (E.C. 4.2.1.3); 9, pyruvate synthase or pyruvate:ferredoxin oxidoreductase (E.C. 1.2.7.1); 10, phosphoenolpyruvate synthetase (E.C. 2.7.9.2); 11, phosphoenolpyruvate carboxylase (E.C. 4.1.1.31).

As used herein, the term "methylotroph" or "methylotrophic organism" refers to organisms that produce complex organic compounds from compounds that lack any carbon-carbon bonds, such as formate, formic acid, formaldehyde, methane, methanol, methylamine, halogenated methanes, and methylated sulfur species. Methylotrophs often use C1 compounds as both a source of energy and carbon. Example methylotrophic metabolic pathways for production of central metabolites from C1 compounds include the ribulose monophosphate cycle (FIG. 1) and the serine cycle (FIG. 2). "Autotrophs" or "autotrophic organisms" refers to organisms that use simple, inorganic carbon molecules, such as carbon dioxide, as its primary carbon source for growth. Some but not all methylotrophs assimilate C1 compounds via carbon dioxide and thus are also autotrophs. These organisms oxidize C1 compounds such as methanol, methylamine, formaldehyde or formate to carbon dioxide (see metabolic pathway depicted in FIG. 3) and then reduce carbon dioxide to central metabolites using carbon fixation cycles using, for example, the Calvin-Benson-Bassham cycle (FIG. 4) or the reductive tricarboxlic acid cycle (FIG. 5). In contrast, "heterotrophs" or "heterotrophic organisms" refers to organisms that must use reduced, organic carbon compounds with carbon-carbon bonds for growth because they cannot use inorganic carbon as their primary carbon source. Instead, heterotrophs obtain energy by breaking down the organic molecules they consume. Organisms that can use a mix of different sources of energy and carbon are mixotrophs or mixotrophic organisms which can alternate, e.g., between autotrophy and heterotrophy, between autotrophy and methylotrophy, between heterotrophy and methylotrophy, between phototrophy and chemotrophy, between lithotrophy and organotrophy, or a combination thereof, depending on environmental conditions.

As used herein, the term "reducing cofactor" refers to intracellular redox and energy carriers, such as NADH, NADPH, ubiquinol, menaquinol, cytochromes, flavins and/or ferredoxin, that can donate high energy electrons in reduction-oxidation reactions. The terms "reducing cofacor", "reduced cofactor" and "redox cofactor" can be used interchangeably.

As used herein, the term "C1 compound", "1C compound" or "$C_1$ compound" refers to chemical species that are reduced species but contain no carbon-carbon bonds. C1 compounds may contain either one carbon atom (e.g., formate, formic acid, formamide, formaldehyde, methane, methanol, methylamine, halogenated methanes, monomethyl sulfate) or multiple carbon atoms (e.g., dimethyl ether, dimethylamine, dimethyl sulfide). Furthermore, C1 compounds may be either inorganic (e.g., formate, formic acid) or organic e.g., formaldehyde, methane, methanol). C1 compounds often serve as both a source of energy and a source of carbon for methylotrophs.

As used herein, the term "central metabolite" refers to organic carbon compounds, such as acetyl-coA, pyruvate, pyruvic acid, 3-hydropropionate, 3-hydroxypropionic acid, glycolate, glycolic acid, glyoxylate, glyoxylic acid, dihydroxyacetone phosphate, glyceraldehyde-3-phosphate, malate, malic acid, lactate, lactic acid, acetate, acetic acid, citrate and/or citric acid, that can be converted into carbon-based products of interest by a host cell or organism. Central metabolites are generally restricted to those reduced organic compounds from which all or most cell mass components can be derived in a given host cell or organism. In some embodiments, the central metabolite is also the carbon product of interest in which case no additional chemical conversion is necessary.

Reference to a particular chemical species includes not only that species but also water-solvated forms of the species, unless otherwise stated. For example, carbon dioxide includes not only the gaseous form ($CO_2$) but also water-solvated forms, such as bicarbonate ion.

As used herein, the term "biosynthetic pathway" or "metabolic pathway" refers to a set of anabolic or catabolic biochemical reactions for converting (transmuting) one chemical species into another. Anabolic pathways involve constructing a larger molecule from smaller molecules, a process requiring energy. Catabolic pathways involve breaking down of larger molecules, often releasing energy. As used herein, the term "energy conversion pathway" refers to a metabolic pathway that transfers energy from a C1 compound to a reducing cofactor. The term "carbon fixation pathway" refers to a biosynthetic pathway that converts inorganic carbon, such as carbon dioxide, bicarbonate or formate, to reduced organic carbon, such as one or more carbon product precursors. The term "methylotrophic pathway" refers to a biosynthetic pathway that converts C1 compounds to compounds with carbon-carbon bonds, such as one or more carbon product precursors. The term "carbon product biosynthetic pathway" refers to a biosynthetic pathway that converts one or more carbon product precursors to one or more carbon based products of interest.

As used herein, the term "engineered methylotroph" or "engineered methylotrophic organism" refers to organisms that have been genetically engineered to convert C1 compounds, such as formate, formic acid, formaldehyde, or methanol, to organic carbon compounds. As used herein, an engineered methylotroph need not derive its organic carbon compounds solely from C1 compounds. The term engineered methylotroph may also be used to refer to originally methylotrophic or mixotrophic organisms that have been genetically engineered to include one or more energy conversion, carbon fixation, methylotrophic and/or carbon product biosynthetic pathways in addition or instead of its endogenous methylotrophic capability. The term "engineer," "engineering" or "engineered," as used herein, refers to genetic manipulation or modification of biomolecules such as DNA, RNA and/or protein, or like technique commonly known in the biotechnology art.

As used herein, the term "carbon based products of interest" refers to a desired product containing carbon atoms and include, but not limited to alcohols such as ethanol, propanol, isopropanol, butanol, octanol, fatty alcohols, fatty acid esters, wax esters; hydrocarbons and alkanes such as propane, octane, diesel, Jet Propellant 8, polymers such as terephthalate, 1,3-propanediol, 1,4-butanediol, polyols, polyhydroxyalkanoates (PHAs), polyhydroxybutyrates (PHBs), acrylate, adipic acid, epsilon-caprolactone, isoprene, caprolactam, rubber; commodity chemicals such as lactate, docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxyprionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; biological sugars such as glucose, fructose, lactose, sucrose, starch, cellulose, hemicellulose, glycogen, xylose, dextrose, galactose, uronic acid, maltose, polyketides, or glycerol; central metabolites, such as acetyl-coA, pyruvate, pyruvic acid, 3-hydropropionate, 3-hydroxypropionic acid, glycolate, glycolic acid, glyoxylate, glyoxylic acid, dihydroxyacetone phosphate, glyceraldehyde-3-phosphate, malate, malic acid, lactate, lactic acid, acetate, acetic acid, citrate and/or citric acid, from which other carbon products can be made; pharmaceuticals and pharmaceutical intermediates such as 7-aminodesacetoxycephalosporonic acid, cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, neutraceuticals, polymers, paraffin replacements, personal care products and pharmaceuticals.

As used herein, the term "hydrocarbon" referes a chemical compound that consists of the elements carbon, hydrogen and optionally, oxygen. "Surfactants" are substances capable of reducing the surface tension of a liquid in which they are dissolved. They are typically composed of a water-soluble head and a hydrocarbon chain or tail. The water soluble group is hydrophilic and can either be ionic or nonionic, and the hydrocarbon chain is hydrophobic. The term "biofuel" is any fuel that derives from a biological source.

The accession numbers provided throughout this description are derived from the NCBI database (National Center for Biotechnology Information) maintained by the National Institute of Health, USA. The accession numbers are provided in the database on Aug. 1, 2011. The Enzyme Classification Numbers (E.C.) provided throughout this description are derived from the KEGG Ligand database, maintained by the Kyoto Encyclopedia of Genes and Genomics, sponsored in part by the University of Tokyo. The E.C. numbers are provided in the database on Aug. 1, 2011.

Other terms used in the fields of recombinant nucleic acid technology, microbiology, metabolic engineering, and molecular and cell biology as used herein will be generally understood by one of ordinary skill in the applicable arts.

Source of C1 Compounds

In some embodiments, suitable C1 compounds include, but not limited to formate, formic acid, methanol and/or formaldehyde. Formate, formic acid, formaldehyde and methanol can be produced via the electrochemical reduction of $CO_2$ [see, e.g., Hori, 2008].

In some instances, soluble, liquid feedstocks such as formate, formic acid, formaldehyde or methanol can be preferable to gaseous feedstocks, such as methane or synthesis gas. Methane is generally known as a gas with low water solubility in water which creates mass transfer limitations when using methane as the feedstock for engineered and/or evolved methylotrophs (biological systems are aqueous). Similarly, synthesis gas (composed of molecular hydrogen and carbon monoxide) also has low water solubility in water. At large reactor or fermentor scales, high rates of mass transfer from the gas to liquid phases is challenging. In contrast, formate, formaldehyde and methanol due to their higher solubility/miscibility in $H_2O$, do not have this problem. Hence, when water is the solvent in the growth media, the use of formate, formic acid, formaldehyde or methanol as the feedstock can be more advantageous.

The energy efficiency of electrochemical conversion of carbon dioxide impacts the overall energy efficiency of a bio-manufacturing process using an engineered and/or evolved methylotroph of the present invention. Electrolyzers achieve overall energy efficiencies of 56-73% at current densities of 110-300 $mA/cm^2$ (alkaline electrolyzers) or 800-1600 $mA/cm^2$ (PEM electrolyzers) [Whipple, 2010]. In contrast, electrochemical systems to date have achieved moderate energy efficiencies or high current densities but not at the same time. Hence, additional technology improvements are needed for electrochemical production of formate, formic acid, formaldehyde and methanol.

Organisms or Host Cells for Engineering or Evolution

The host cell or organism, as disclosed herein, may be chosen from methylotrophic eukaryotic or prokaryotic systems, such as bacterial cells (Gram-negative (e.g., Alphaproteobacterium) or Gram-positive), archaea and yeast cells. Suitable cells and cell lines can also include those commonly used in laboratories and/or industrial applications. In some embodiments, host cells/organisms can be selected from *Bacillus* species including *Bacillus methanolicus, Bilophila wadsworthia, Burkholderia* species including *Burkholderia phymatum, Candida* species including *Candida boidinii, Candida sonorensis, Cupravidus necator* (formerly *Alcaligenes eutrophus* and *Ralstonia eutropha*), *Hyphomicrobium* species including *Hyphomicrobium methylovorum, Hyphomicrobium zavarzinii, Methanococcus maripaludis, Methanomonas methanooxidans, Methanosarcina* species, *Methylibium petroleiphilum, Methylobacillus flagellatus, Methylobacillus flagellatum, Methylobacillus fructoseoxidans, Methylobacillus glycogenes, Methylobacillus viscogenes, Methylobacter bovis, Methylobacter capsulatus, Methylobacter vinelandii, Methylobacterium* species including *Methylobacterium dichloromethanicum, Methylobacterium extorquens, Methylobacterium mesophilicum, Methylobacterium organophilum, Methylobacterium rhodesianum, Methylococcus capsulatus, Methylococcus*

*minimus*, *Methylocystis* species including *Methylocystis parvus*, *Methylomicrobium alcaliphilum*, *Methylomonas* species including *Methylomonas agile*, *Methylomonas albus*, *Methylomonas clara*, *Methylomonas methanica* (formerly *Bacillus methanicus* and *Pseudomonas methanica*), *Methylomonas methanolica*, *Methylomonas rosaceous*, *Methylomonas rubrum*, *Methylomonas streptobacterium*, *Methylophilus methylotrophus*, *Methylosinus* species including *Methylosinus sporium*, *Methylosinus trichosporium*, *Methylosporovibrio methanica*, *Methyloversatilis universalis*, *Methylovorus mays*, *Mycobacterium vaccae*, *Nautilia* sp. strain AmN, *Nautilia lithotrophica*, *Nautilia profundicola*, *Paracoccus* species including *Paracoccus denitrificans*, *Paracoccus versutus* or *Paracoccus zeaxanthinifaciens*, *Picchia* species including *Picchia angusta* (formerly *Hansenula polymorpha*), *Picchia guilliermondii*, *Picchia pastoris*, *Protaminobacter ruber*, *Pseudomonas* species including *Pseudomonas AM1*, *Pseudomonas methanitrificans*, *Schlegelia plantiphila*, *Thermocrinus ruber*, *Verrucomicrobia* species, *Xanthobacter* species, or any modifications and/or derivatives thereof. Those skilled in the art would understand that the genetic modifications, including metabolic alterations exemplified herein, are described with reference to a suitable host organism such as *Paracoccus denitrificans* and their corresponding metabolic reactions or a suitable source organism for desired nucleic acids such as genes for a desired metabolic pathway. However, given the complete genome sequencing of a wide variety of organisms and the high level of skill in the area of genomics, those skilled in the art would readily be able to apply the teachings and guidance provided herein to essentially all other methylotrophic host cells and organisms. For example, the *Paracoccus denitrificans* metabolic modifications exemplified herein can readily be applied to other species by incorporating the same or analogous encoding nucleic acid from species other than the referenced species. Such genetic modifications include, for example, genetic alterations of species homologs, in general, and in particular, orthologs, paralogs or nonorthologous gene displacements.

In various aspects of the invention, the cells are genetically engineered and/or metabolically evolved, for example, for the purposes of optimized energy conversion, methylotrophy and/or carbon fixation. The terms "metabolically evolved" or "metabolic evolution" relates to growth-based selection (metabolic evolution) of host cells that demonstrate improved growth (cell yield).

Exemplary genomes and nucleic acids include full and partial genomes of a number of organisms for which genome sequences are publicly available and can be used with the disclosed methods, such as, but not limited to, *Aeropyrum pernix; Agrobacterium tumefaciens; Anabaena; Anopheles gambiae; Apis mellifera; Aquifex aeolicus; Arabidopsis thaliana; Archaeoglobusfulgidus; Ashbya gossypii; Bacillus anthracis; Bacillus cereus; Bacillus halodurans; Bacillus licheniformis; Bacillus subtilis; Bacteroides fragilis; Bacteroides thetaiotaomicron; Bartonella henselae; Bartonella quintana; Bdellovibrio bacteriovirus; Bifidobacterium longum; Blochmannia floridanus; Bordetella bronchiseptica; Bordetella parapertussis; Bordetella pertussis; Borrelia burgdorferi; Bradyrhizobium japonicum; Brucella melitensis; Brucella suis; Buchnera aphidicola; Burkholderia mallei; Burkholderia pseudomallei; Caenorhabditis briggsae; Caenorhabditis elegans; Campylobacter jejuni; Candida glabrata; Canis familiaris; Caulobacter crescentus; Chlamydia muridarum; Chlamydia trachomatis; Chlamydophila caviae; Chlamydophila pneumoniae; Chlorobium tepidum; Chromobacterium violaceum; Ciona intestinalis; Clostridium acetobutylicum; Clostridium perfringens; Clostridium tetania Corynebacterium diphtheriae; Corynebacterium efficiens; Coxiella burnetii; Cryptosporidium hominis; Cryptosporidium parvum; Cyanidioschyzon merolae; Debaryomyces hansenii; Deinococcus radiodurans; Desulfotalea psychrophila; Desulfovibrio vulgaris; Drosophila melanogaster; Encephalitozoon cuniculi; Enterococcusfaecalis; Erwinia carotovora; Escherichia coli; Fusobacterium nucleatum; Gallus gallus; Geobacter sulfurreducens; Gloeobacter violaceus; Guillardia theta; Haemophilus ducreyi; Haemophilus influenzae; Halobacterium; Helicobacter hepaticus; Helicobacter pylori; Homo sapiens; Kluyveromyces waltii; Lactobacillus johnsonii; Lactobacillus plantarum; Legionella pneumophila; Leifsonia xyli; Lactococcus lactis; Leptospira interrogans; Listeria innocua; Listeria monocytogenes; Magnaporthe grisea; Mannheimia succiniciproducens; Mesoplasma florum; Mesorhizobium loti; Methanobacterium thermoautotrophicum; Methanococcoides burtonii; Methanococcus jannaschii; Methanococcus maripaludis; Methanogenium frigidum; Methanopyrus kandleri; Methanosarcina acetivorans; Methanosarcina mazei; Methylococcus capsulatus; Mus musculus; Mycobacterium bovis; Mycobacterium leprae; Mycobacterium paratuberculosis; Mycobacterium tuberculosis; Mycoplasma gallisepticum; Mycoplasma genitalium; Mycoplasma mycoides; Mycoplasma penetrans; Mycoplasma pneumoniae; Mycoplasma pulmonis; Mycoplasma mobile; Nanoarchaeum equitans; Neisseria meningitidis; Neurospora crassa; Nitrosomonas europaea; Nocardia farcinica; Oceanobacillus iheyensis*; Onions yellows phytoplasma; *Oryza sativa; Pan troglodytes; Paracoccus denitrificans; Paracoccus versutus; Paracoccus zeaxanthinifaciens; Pasteurella multocida; Phanerochaete chrysosporium; Photorhabdus luminescens; Picrophilus torridus; Plasmodium falciparum; Plasmodium yoelii yoelii; Populus trichocarpa; Porphyromonas gingivalis Prochlorococcus marinus; Propionibacterium acnes; Protochlamydia amoebophila; Pseudomonas aeruginosa; Pseudomonas putida; Pseudomonas syringae; Pyrobaculum aerophilum; Pyrococcus abyssi; Pyrococcus furiosus; Pyrococcus horikoshii; Pyrolobus fumarii; Ralstonia solanacearum; Rattus norvegicus; Rhodopirellula baltica; Rhodopseudomonas palustris; Rickettsia conorii; Rickettsia typhi; Rickettsia prowazekii; Rickettsia sibirica; Saccharomyces cerevisiae; Saccharomyces bayanus; Saccharomyces boulardii; Saccharopolyspora erythraea; Schizosaccharomyces pombe; Salmonella enterica; Salmonella typhimurium; Schizosaccharomyces pombe; Shewanella oneidensis; Shigella flexneria; Sinorhizobium meliloti; Staphylococcus aureus; Staphylococcus epidermidis; Streptococcus agalactiae; Streptococcus mutans; Streptococcus pneumoniae; Streptococcus pyogenes; Streptococcus thermophilus; Streptomyces avermitilis; Streptomyces coelicolor; Sulfolobus solfataricus; Sulfolobus tokodaii; Synechococcus; Synechoccous elongates; Synechocystis; Takifugu rubripes; Tetraodon nigroviridis; Thalassiosira pseudonana; Thermoanaerobacter tengcongensis; Thermoplasma acidophilum; Thermoplasma volcanium; Thermosynechococcus elongatus; Thermotagoa maritima; Thermus thermophilus; Treponema denticola; Treponema pallidum; Tropheryma whipplei; Ureaplasma urealyticum; Vibrio cholerae; Vibrio parahaemolyticus; Vibrio vulnificus; Wigglesworthia glossinidia; Wolbachia pipientis; Wolinella succinogenes; Xanthomonas axonopodis; Xanthomonas campestris; Xylellafastidiosa; Yarrowia lipolytica; Yersinia pseudotuberculosis*; and *Yersinia pestis* nucleic acids.

In certain embodiments, sources of encoding nucleic acids for enzymes for a biosynthetic pathway can include, for example, any species where the encoded gene product is capable of catalyzing the referenced reaction. Exemplary species for such sources include, for example, *Aeropyrum pernix; Aquifex aeolicus; Aquifex pyrophilus; Candidatus Arcobacter sulfidicus; Candidatus Endoriftia persephone; Candidatus Nitrospira defluvii; Chlorobium limicola; Chlorobium tepidum; Clostridium pasteurianum; Desulfobacter hydrogenophilus; Desulfurobacterium thermolithotrophum; Geobacter metallireducens; Halobacterium* sp. NRC-1; *Hydrogenimonas thermophila; Hydrogenivirga* strain 128-5-R1; *Hydrogenobacter thermophilus; Hydrogenobaculum* sp. Y04AAS1; *Lebetimonas acidiphila* Pd55$^T$; *Leptospirillum ferriphilum; Leptospirillum ferrodiazotrophum; Leptospirillum rubarum; Magnetococcus marinus; Magnetospirillum magneticum; Mycobacterium bovis; Mycobacterium tuberculosis; Methylobacterium nodulans; Nautilia lithotrophica; Nautilia profundicola; Nautilia* sp. strain AmN; *Nitratifractor salsuginis; Nitratiruptor* sp. strain SB155-2; *Paracoccus denitrificans; Paracoccus versutus; Paracoccus zeaxanthinifaciens; Persephonella marina; Rimcaris exoculata episymbiont; Streptomyces avermitilis; Streptomyces coelicolor; Sulfolobus avermitilis; Sulfolobus solfataricus; Sulfolobus tokodaii; Sulfurihydrogenibium azorense; Sulfurihydrogenibium* sp. Y03AOP1; *Sulfurihydrogenibium yellowstonense; Sulfurihydrogenibium subterraneum; Sulfurimonas autotrophica; Sulfurimonas denitrificans; Sulfurimonas paralvinella; Sulfurovum lithotrophicum; Sulfurovum* sp. strain NBC37-1; *Thermocrinis ruber; Thermovibrio ammonificans; Thermovibrio ruber; Thioreductor micatisoli; Nostoc* sp. PCC 7120; *Acidithiobacillus ferrooxidans; Allochromatium vinosum; Aphanothece halophytica; Oscillatoria limnetica; Rhodobacter capsulatus; Thiobacillus denitrificans; Cupriavidus necator* (formerly *Ralstonia eutropha*), *Methanosarcina barkeri; Methanosarcia mazei; Methanococcus maripaludis; Mycobacterium smegmatis; Burkholderia stabilis; Candida boidinii; Candida methylica; Pseudomonas* sp. 101; *Methylcoccus capsulatus; Mycobacterium gastri; Cenarchaeum symbiosum; Chloroflexus aurantiacus; Erythrobacter* sp. NAP1; *Metallosphaera sedula*; gamma proteobacterium NOR51-B; marine gamma proteobacterium HTCC2080; *Nitrosopumilus maritimus; Roseiflexus castenholzii; Synechococcus elongatus*; and the like, as well as other exemplary species disclosed herein or available as source organisms for corresponding genes. However, with the complete genome sequence publicly available for now more than 4400 species (including viruses), including 1701 microbial genomes and a variety of yeast, fungi, plant, and mammalian genomes, the identification of genes encoding the requisite energy conversion, methylotrophic, carbon fixation or carbon product biosynthetic activity for one or more genes in related or distant species, including for example, homologs, orthologs, paralogs and nonorthologous gene displacements of known genes, and the replacement of gene homolog either within a particular engineered and/or evolved methylotroph or between different host cells for the engineered and/or evolved methylotroph is routine and well known in the art. Accordingly, the metabolic modifications enabling methylotrophic growth and production of carbon-based products described herein with reference to a particular organism such as *Paracoccus denitrificans* can be readily applied to other methylotrophic microorganisms, including prokaryotic and eukaryotic organisms alike. Given the teachings and guidance provided herein, those skilled in the art would know that a metabolic modification exemplified in one organism can be applied equally to other organisms.

In some instances, such as when an alternative energy conversion, carbon fixation, methylotrophic or carbon product biosynthetic pathway exists in an unrelated species, enhanced methylotrophic growth and production of carbon-based products can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art would understand that the actual gene usage between different organisms may differ. However, given the teachings and guidance provided herein, those skilled in the art also would understand that the teachings and methods of the invention can be applied to all microbial organisms using the cognate metabolic modifications to those exemplified herein to construct a microbial organism in a species of interest that would produce carbon-based products of interest from C1 compounds.

It should be noted that various engineered strains and/or mutations of the organisms or cell lines discussed herein can also be used.

Methods for Identification and Selection of Candidate Enzymes for a Metabolic Activity of Interest In one aspect, the present invention provides a method for identifying candidate proteins or enzymes of interest capable of performing a desired metabolic activity. Leveraging the exponential growth of gene and genome sequence databases and the availability of commercial gene synthesis at reasonable cost, Bayer and colleagues adopted a synthetic metagenomics approach to bioinformatically search sequence databases for homologous or similar enzymes, computationally optimize their encoding gene sequences for heterologous expression, synthesize the designed gene sequence, clone the synthetic gene into an expression vector and screen the resulting enzyme for a desired function in *E. coli* or yeast [Bayer, 2009]. However, depending on the metabolic activity or protein of interest, there can be thousands of putative homologs in the publicly available sequence databases. Thus, it can be experimentally challenging or in some cases infeasible to synthesize and screen all possible homologs at reasonable cost and within a reasonable timeframe. To address this challenge, in one aspect, this invention provides an alternate method for identifying and selecting candidate protein sequences for a metabolic activity of interest. The method comprises the following steps. First, for a desired metabolic activity, such as an enzyme-catalyzed step in an energy conversion, methylotrophic, carbon fixation or carbon product biosynthetic pathway, one or more enzymes of interest are identified. Typically, the enzyme(s) of interest have been previously experimentally validated to perform the desired activity, for example in the published scientific literature. In some embodiments, one or more of the enzymes of interest has been heterologously expressed and experimentally demonstrated to be functional. Second, a bioinformatic search is performed on protein classification or grouping databases, such as Clusters of Orthologous Groups (COGs) [Tatusov, 1997; Tatusov, 2003], Entrez Protein Clusters (ProtClustDB) [Klimke, 2009] and/or InterPro [Zdobnov, 2001], to identify protein groupings that contain one or more of the enzyme(s) of interest (or closely related enzymes). If the enzyme(s) of interest contain multiple subunits, then the protein corresponding to a single subunit, for example the catalytic subunit or the largest subunit, is selected as being representative of the enzyme(s)

of interest for the purposes of bioinformatic analysis. Third, a systematic, expert-guided search is then performed to identify which database groupings are likely to contain a majority of members whose metabolic activity is the same or similar as the protein(s) of interest. Fourth, the list of NCBI Protein accession numbers corresponding to every members of each selected database grouping is then compiled and the corresponding protein sequences are downloaded from the sequence databases. Protein sequences available from sources other than the public sequence databases may be added to this set. Fifth, optionally, one or more outgroup protein sequences are identified and added to the set. Outgroup proteins are proteins which may share some functional, structural, or sequence similarities to the model enzyme(s) but lack an essential feature of the enzyme(s) of interest or desired metabolic activity. For example, the enzyme flavocytochrome c (E.C. 1.8.2.3) is similar to sulfide-quinone oxidoreductase (E.C. 1.8.5.4) in that it oxidizes hydrogen sulfide but it reduces cytochrome c instead of ubiquinone and thus offers a useful outgroup during bioinformatic analysis of sulfide-quinone oxidoreductases. Sixth, the complete set of protein sequences are aligned with an sequence alignment program capable of aligning large numbers of sequences, such as MUSCLE [Edgar, 2004a; Edgar, 2004b]. Seventh, a tree is drawn based on the resulting MUSCLE alignment via methods known to those skilled in the art, such as neighbor joining [Saitou, 1987] or UPGMA [Sokal, 1958; Murtagh, 1984]. Eighth, different clades are selected from the tree so that the number of clades equals the desired number of proteins for screening. Finally, one protein from each clade is selected for gene synthesis and functional screening based on the following heuristics Preference is given to proteins that have been heterologously expressed and experimentally demonstrated to have the desired metabolic activity.

Preference is given to proteins that have been biochemically characterized to have the desired metabolic activity previously.

Preference is given to proteins from source organisms for which there is strong experimental or genomic evidence that the organism has the desired metabolic activity.

Preference is given to proteins in which the key catalytic, binding and/or other signature residues are conserved with respect to the protein(s) of interest.

Preference is given to protein from source organisms whose optimal growth temperature is similar to that of the host cell or organism. For example, if the host cell is a mesophile, then the source organism is also a mesophile.

Therefore, in constructing the engineered and/or evolved methylotroph of the invention, those skilled in the art would understand that by applying the teaching and guidance provided herein, it is possible to replace or augment particular genes within a metabolic pathway, such as an energy conversion pathway, a carbon fixation pathway, a methylotrophic pathway and/or a carbon product biosynthetic pathway, with homologs identified using the methods described here, whose gene products catalyze a similar or substantially similar metabolic reaction. Such modifications can be done, for example, to increase flux through a metabolic pathway (for example, flux of energy or carbon), to reduce accumulation of toxic intermediates, to improve the kinetic properties of the pathway, and/or to otherwise optimize the engineered and/or evolved methylotroph.

Methods for Design of Nucleic Acids Encoding Enzymes for Heterologous Expression In one aspect, the present invention provides a computer program product for designing a nucleic acid that encodes a protein or enzyme of interest that is codon optimized for the host cell or organism (the target species). The program can reside on a hardware computer readable storage medium and having a plurality of instructions which, when executed by a processor, cause the processor to perform operations. The program comprises the following operations. At each amino acid position of the protein of interest, the codon is selected in which the rank order codon usage frequency of that codon in the target species is the same as the rank order codon usage frequency of the codon that occurs at that position in the source species gene. To select the desired codon at each amino acid position, both the genetic code (the mapping of codons to amino acids [Jukes, 1993]) and codon frequency table (the frequency with which each synonymous codon occurs in a genome or genome [Grantham, 1980]) for both the source and target species are needed. For source species for which a complete genome sequence is available, the usage frequency for each codon may be calculate simply by summing the number of instances of that codon in all annotated coding sequences, dividing by the total number of codons in that genome, and then multiplying by 1000. For source species for which no complete genome is available, the usage frequency can be computed based on any available coding sequences or by using the codon frequency table of a closely related organism. The program then preferably standardizes the start codon to ATG, the stop codon to TAA, and the second and second last codons to one of twenty possible codons (one per amino acid). The program then subjects the codon optimized nucleic acid sequence to a series of checks to improve the likelihood that the sequence can be synthesized via commercial gene synthesis and subsequently manipulated via molecular biology [Sambrook, 2001] and DNA assembly methods [WO/2010/070295]. These checks comprise identifying if key restriction enzyme recognition sites used in a DNA assembly standard or DNA assembly method are present; if hairpins whose GC content exceeds a threshold percentage, such as 60%, and whose length exceeds a threshold number of base pairs, such as 10, are present; if sequence repeats are present; if any subsequence between 100 and 150 nucleotides in length exceeds a threshold GC content, such as 65%; if G or C homopolymers greater than 5 nucleotides in length are present; and, optionally, if any sequence motifs are present that might give rise to spurious transposon insertion sites, transcriptional or translational initiation or termination, mRNA secondary structure, RNase cleavage, and/or transcription factor binding. If the codon optimized nucleic acid sequence fails any of these checks, the program then iterates through all possible synonymous mutations and designs a new nucleic acid sequence that both passes all checks and minimizes the difference in codon frequencies between the original and new nucleic acid sequence.

Various implementations of the systems and techniques described here can be realized in digital electronic circuitry, integrated circuitry, specially designed ASICs (application-specific integrated circuits), computer hardware, firmware, software, and/or combinations thereof. These various implementations can include one or more computer programs that are executable and/or interpretable on a programmable system including at least one programmable processor, which may be special or general purpose, coupled to receive data and instructions from, and to transmit data and instructions to, a storage system, at least one input device, and at least one output device. Such computer programs (also known as programs, software, software applications or code) may include machine instructions for a programmable processor, and may be implemented in any form of programming language, including high-level procedural and/or object-oriented programming languages, and/or in assembly/machine languages. A computer program may be deployed in any form, including as a stand-alone program, or as a module, component, subroutine, or other unit suitable for use in a computing environment. A computer program may be deployed to be executed or interpreted on one computer or on multiple computers at one site, or distributed across multiple sites and interconnected by a communication network.

A computer program may, in an embodiment, be stored on a computer readable storage medium. A computer readable storage medium stores computer data, which data can include computer program code that is executed and/or interpreted by a computer system or processor. By way of example, and not limitation, a computer readable medium may comprise computer readable storage media, for tangible or fixed storage of data, or communication media for transient interpretation of code-containing signals. Computer readable storage media, may refer to physical or tangible storage (as opposed to signals) and may include without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Figure 6:
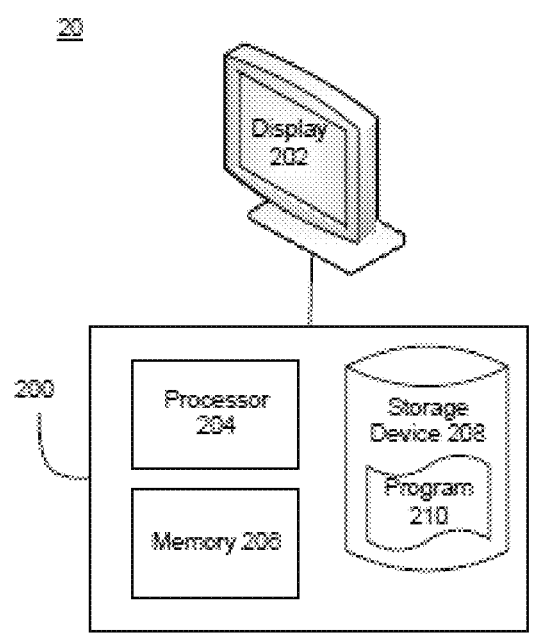
FIG. 6 is a block diagram of a computing architecture.

FIG. 6 shows a block diagram of a generic processing architecture, which may execute software applications and processes. Computer processing device 200 may be coupled to display 202 for graphical output. Processor 204 may be a computer processor capable of executing software. Typical examples of processor 204 are general-purpose computer processors (such as Intel® or AMD® processors), ASICs, microprocessors, any other type of processor, or the like. Processor 204 may be coupled to memory 206, which may be a volatile memory (e.g. RAM) storage medium for storing instructions and/or data while processor 204 executes. Processor 204 may also be coupled to storage device 208, which may be a non-volatile storage medium such as a hard drive, FLASH drive, tape drive, DVDROM, or similar device. Program 210 may be a computer program containing instructions and/or data, and may be stored on storage device 208 and/or in memory 206, for example. In a typical scenario, processor 204 may load some or all of the instructions and/or data of program 210 into memory 206 for execution.

Program 210 may be a computer program capable of performing the processes and functions described above. Program 210 may include various instructions and subroutines, which, when loaded into memory 206 and executed by processor 204 cause processor 204 to perform various operations, some or all of which may effectuate the methods, processes, and/or functions associated with the presently disclosed embodiments.

Although not shown, computer processing device 200 may include various forms of input and output. The I/O may include network adapters, USB adapters, Bluetooth radios, mice, keyboards, touchpads, displays, touch screens, LEDs, vibration devices, speakers, microphones, sensors, or any other input or output device for use with computer processing device 200.

Methods for Expression of Heterologous Enzymes

Composite nucleic acids can be constructed to include one or more energy conversion, methylotrophic, carbon fixation and/or carbon product biosynthetic pathway encoding nucleic acids as exemplified herein. The composite nucleic acids can subsequently be transformed or transfected into a suitable host organism for expression of one or more proteins of interest. Composite nucleic acids can be constructed by operably linking nucleic acids encoding one or more standardized genetic parts with protein(s) of interest encoding nucleic acids that have also been standardized. Standardized genetic parts are nucleic acid sequences that have been refined to conform to one or more defined technical standards, such as an assembly standard [Knight, 2003; Shetty, 2008; Shetty, 2011]. Standardized genetic parts can encode transcriptional initiation elements, transcriptional termination elements, translational initiation elements, translational termination elements, protein affinity tags, protein degradation tags, protein localization tags, selectable markers, replication elements, recombination sites for integration onto the genome, and more. Standardized genetic parts have the advantage that their function can be independently validated and characterized [Kelly, 2009] and then readily combined with other standardized parts to produce functional nucleic acids [Canton, 2008]. By mixing and matching standardized genetic parts encoding different expression control elements with nucleic acids encoding proteins of interest, transforming the resulting nucleic acid into a suitable host cell and functionally screening the resulting engineered cell, the process of both achieving soluble expression of proteins of interest and validing the function of those proteins is made dramatically faster. For example, the set of standardized parts might comprise constitutive promoters of varying strengths [Davis, 2011], ribosome binding sites of varying strengths [Anderson, 2007] and protein degradation of tags of varying strengths [Andersen, 1998].

For exogenous expression in *Paracoccus* or other prokaryotic cells, some nucleic acids encoding proteins of interest can be modified to introduce solubility tags onto the protein of interest to ensure soluble expression of the protein of interest. For example, addition of the maltose binding protein to a protein of interest has been shown to enhance soluble expression in *E. coli* [Sachdev, 1998; Kapust, 1999; Sachdev, 2000]. Either alternatively or in addition, chaperone proteins, such as DnaK, DnaJ, GroES and GroEL may be either co-expressed or overexpressed with the proteins of interest, such as RuBisCO [Greene, 2007], to promote correct folding and assembly [Martinez-Alonso, 2009; Martinez-Alonso, 2010].

For exogenous expression in *Parococcus* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* [Hoffmeister, 2005]. For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties.

Exemplary, optimized methods for introduction of exogenous nucleic acids into the methylotrophic bacteria *Paracoccus versutus* and *Paracoccus denitrificans* via conjugative plasmid transfer are described in detail herein in Example 2.

Production of Central Metabolites as the Carbon-Based Products of Interest

Figure 7:
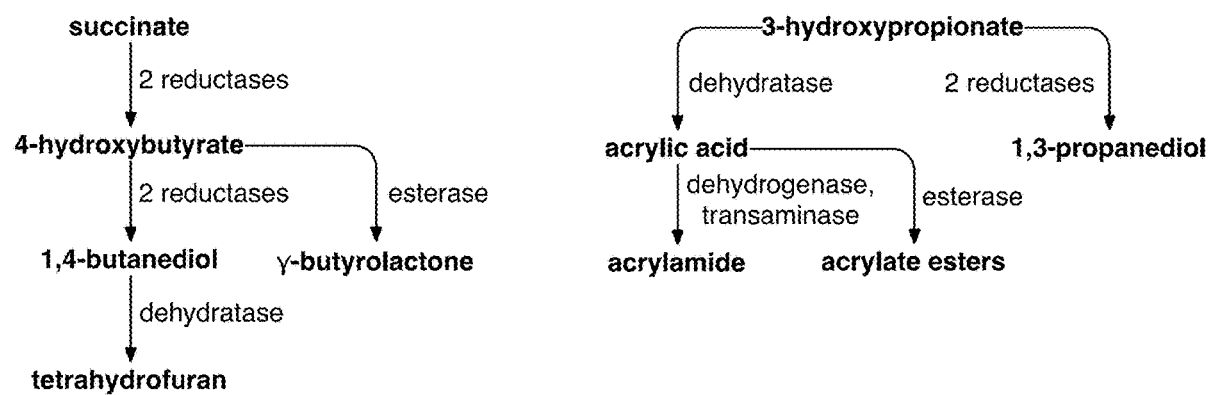
FIG. 7 provides a schematic to convert succinate or 3-hydroxypropionate to various chemicals.

In certain embodiments, the engineered and/or evolved methylotroph of the present invention produces the central metabolites, including but not limited to citrate, malate, succinate, fumarate, dihydroxyacetone, dihydroxyacetone phosphate, 3-hydroxypropionate, pyruvate, as the carbon-based products of interest. The engineered and/or evolved methylotroph produces central metabolites as an intermediate or product of the carbon fixation or methylotrophic pathway or as a intermediate or product of host metabolism. In such cases, one or more transporters may be expressed in the engineered and/or evolved methylotroph to export the central metabolite from the cell. For example, one or more members of a family of enzymes known as C4-dicarboxylate carriers serve to export succinate from cells into the media [Janausch, 2002; Kim, 2007]. These central metabolites can be converted to other products (FIG. 7).

In some embodiments, the engineered and/or evolved methylotroph may interconvert between different central metabolites to produce alternate carbon-based products of interest. In one embodiment, the engineered and/or evolved methylotroph produces aspartate by expressing one or more aspartate aminotransferase (E.C. 2.6.1.1), such as *Escherichia coli* AspC, to convert oxaloacetate and L-glutamate to L-aspartate and 2-oxoglutarate.

In another embodiment, the engineered and/or evolved methylotroph produces dihydroxyacetone phosphate by expressing one or more dihydroxyacetone kinases (E.C. 2.7.1.29), such as *C. freundii* DhaK, to convert dihydroxyacetone and ATP to dihydroxyacetone phosphate.

In another embodiment, the engineered and/or evolved methylotroph produces serine as the carbon-based product of interest. The metabolic reactions necessary for serine biosynthesis include: phosphoglycerate dehydrogenase (E.C. 1.1.1.95), phosphoserine transaminase (E.C. 2.6.1.52), phosphoserine phosphatase (E.C. 3.1.3.3). Phosphoglycerate dehydrogenase, such as *E. coli* SerA, converts 3-phospho-D-glycerate and $NAD^+$ to 3-phosphonooxypyruvate and NADH. Phosphoserine transaminase, such as *E. coli* SerC, interconverts between 3-phosphonooxypyruvate+L-glutamate and O-phospho-L-serine+2-oxoglutarate. Phosphoserine phosphatase, such as *E. coli* SerB, converts O-phospho-L-serine to L-serine.

Figure 8:
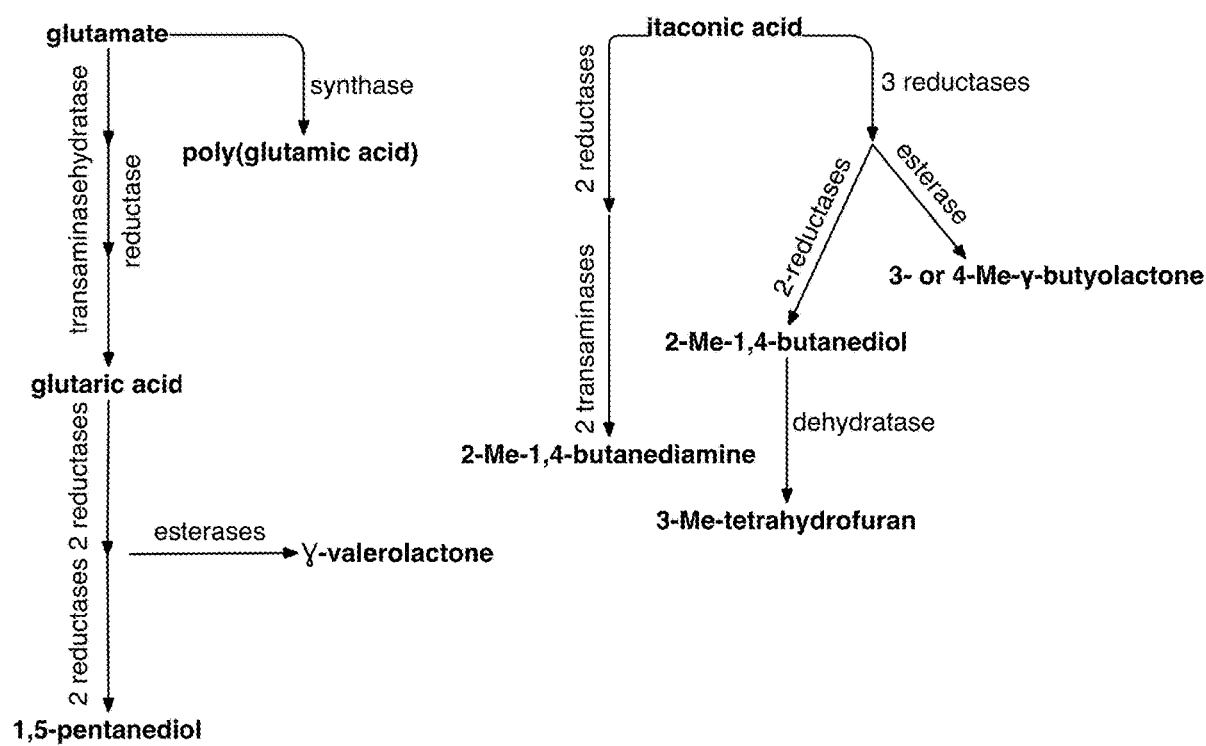
FIG. 8 provides a schematic of glutamate or itaconic acid conversion to various chemicals.

In another embodiment, the engineered and/or evolved methylotroph produces glutamate as the carbon-based product of interest. The metabolic reactions necessary for glutamate biosynthesis include glutamate dehydrogenase (E.C. 1.4.1.4; e.g., *E. coli* GdhA) which converts α-ketoglutarate, $NH_3$ and NADPH to glutamate. Glutamate can subsequently be converted to various other carbon-based products of interest, e.g., according to the scheme presented in FIG. 8.

In another embodiment, the engineered and/or evolved methylotroph produces itaconate as the carbon-based product of interest. The metabolic reactions necessary for itaconate biosynthesis include aconitate decarboxylase (E. C. 4.1.1.6; such as that from *A. terreus*) which converts cis-aconitate to itaconate and $CO_2$. Itaconate can subsequently be converted to various other carbon-based products of interest, e.g., according to the scheme presented in FIG. 8.

Production of Sugars as the Carbon-Based Products of Interest

Industrial production of chemical products from biological organisms is often accomplished using a sugar source, such as glucose or fructose, as the feedstock. Hence, in certain embodiments, the engineered and/or evolved methylotroph of the present invention produces sugars including glucose and fructose or sugar phosphates including triose phosphates (such as 3-phosphoglyceraldehyde and dihydroxyacetone-phosphate) as the carbon-based products of interest. Sugars and sugar phosphates may also be interconverted. For example, glucose-6-phosphate isomerase (E.C. 5.3.1.9; e.g., *E. coli* Pgi) may interconvert between D-fructose 6-phosphate and D-glucose-6-phosphate. Phosphoglucomutase (E.C. 5.4.2.2; e.g., *E. coli* Pgm) converts D-α-glucose-6-P to D-α-glucose-1-P. Glucose-1-phosphatase (E.C. 3.1.3.10; e.g., *E. coli* Agp) converts D-α-glucose-1-P to D-α-glucose. Aldose 1-epimerase (E.C. 5.1.3.3; e.g., *E. coli* GalM) D-β-glucose to D-α-glucose. The sugars or sugar phosphates may optionally be exported from the engineered and/or evolved methylotroph into the culture medium.

Sugar phosphates may be converted to their corresponding sugars via dephosphorylation that occurs either intra- or extracellularly. For example, phosphatases such as a glucose-6-phosphatase (E.C. 3.1.3.9) or glucose-1-phosphatase (E.C. 3.1.3.10) can be introduced into the engineered and/or evolved methylotroph of the present invention. Exemplary phosphatases include *Homo sapiens* glucose-6-phosphatase G6PC (P35575), *Escherichia coli* glucose-1-phosphatase Agp (P19926), *E. cloacae* glucose-1-phosphatase AgpE (Q6EV19) and *Escherichia coli* acid phosphatase YihX (POA8Y3).

Sugar phosphates can be exported from the engineered and/or evolved methylotroph into the culture media via transporters. Transporters for sugar phosphates generally act as anti-porters with inorganic phosphate. An exemplary triose phosphate transporter includes *A. thaliana* triose-phosphate transporter APE2 (Genbank accession AT5G46110.4). Exemplary glucose-6-phosphate transporters include *E. coli* sugar phosphate transporter UhpT (NP_418122.1), *A. thaliana* glucose-6-phosphate transporter GPT1 (AT5G54800.1), *A. thaliana* glucose-6-phosphate transporter GPT2, or homologs thereof. Dephosphorylation of glucose-6-phosphate can also be coupled to glucose transport, such as Genbank accession numbers AAA16222, AAD19898, O43826.

Sugars can be diffusively effluxed from the engineered and/or evolved methylotroph into the culture media via permeases. Exemplary permeases include *H. sapiens* glucose transporter GLUT-1, -3, or -7 (P11166, P11169, Q6PXP3), *S. cerevisiae* hexose transporter HXT-1, -4, or -6 (P32465, P32467, P39003), *Z. mobilis* glucose uniporter Glf (P21906), *Synechocystis* sp. 1148 glucose/fructose:$H^+$ symporter GlcP (T.C. 2.A.1.1.32; P15729) [Zhang, 1989], *Streptomyces lividans* major glucose (or 2-deoxyglucose) uptake transporter GlcP (T.C. 2.A.1.1.35; Q7BEC4) [van Wezel, 2005], *Plasmodium falciparum*: hexose (glucose and fructose) transporter PfHT1 (T.C. 2.A. 1.1.24; O97467), or homologs thereof. Alternatively, to enable active efflux of sugars from the engineered and/or evolved methylotroph, one or more active transporters may be introduced to the cell. Exemplary transporters include mouse glucose transporter GLUT 1 (AAB20846) or homologs thereof.

In some embodiments, to prevent buildup of other storage polymers from sugars or sugar phosphates, the engineered and/or evolved methylotrophs of the present invention are attenuated in their ability to build other storage polymers such as glycogen, starch, sucrose, and cellulose using one or more of the following enzymes: cellulose synthase (UDP forming) (E.C. 2.4.1.12), glycogen synthase e.g. glgA1, glgA2 (E.C. 2.4.1.21), sucrose phosphate synthase (E.C. 2.4.1.14), sucrose phosphorylase (E.C. 3.1.3.24), alpha-1,4-glucan lyase (E.C. 4.2.2.13), glycogen synthase (E.C. 2.4.1.11), 1,4-alpha-glucan branching enzyme (E.C. 2.4.1.18).

Figure 9:
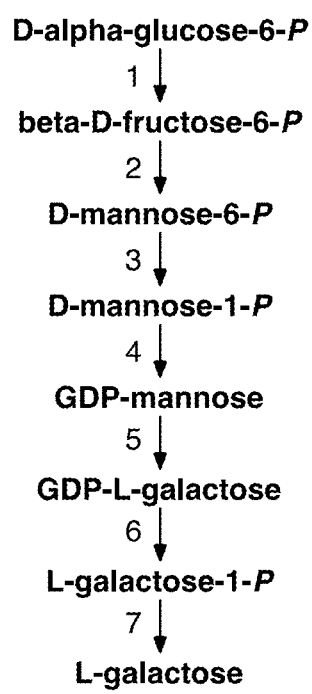
FIG. 9 depicts the metabolic reactions of a galactose biosynthetic pathway. In metabolite names, —P denotes phosphate. Each reaction is numbered. Enzymes catalyzing each reaction are as follows: 1, alpha-D-glucose-6-phosphate ketol-isomerase (E.C. 5.3.1.9); 2, D-mannose-6-phosphate ketol-isomerase (E.C. 5.3.1.8); 3, D-mannose 6-phosphate 1,6-phosphomutase (E.C. 5.4.2.8); 4, mannose-1-phosphate guanylyltransferase (E.C. 2.7.7.22); 5, GDP-mannose 3,5-epimerase (E.C. 5.1.3.18); 6, galactose-1-phosphate guanylyltransferase (E.C. 2.7.n.n); 7, L-galactose 1-phosphate phosphatase (E.C. 3.1.3.n).

The invention also provides engineered and/or evolved methylotrophs that produce other sugars such as sucrose, xylose, lactose, maltose, pentose, rhamnose, galactose and arabinose according to the same principles. A pathway for galactose biosynthesis is shown (FIG. 9). The metabolic reactions in the galactose biosynthetic pathway are catalyzed by the following enzymes: alpha-D-glucose-6-phosphate ketol-isomerase (E.C. 5.3.1.9; e.g., *Arabidopsis thaliana* PGI1), D-mannose-6-phosphate ketol-isomerase (E.C. 5.3.1.8; e.g., *Arabidopsis thaliana* DIN9), D-mannose 6-phosphate 1,6-phosphomutase (E.C. 5.4.2.8; e.g., *Arabidopsis thaliana* ATPMM), mannose-1-phosphate guanylyltransferase (E.C. 2.7.7.22; e.g., *Arabidopsis thaliana* CYT), GDP-mannose 3,5-epimerase (E.C. 5.1.3.18; e.g., *Arabidopsis thaliana* GME), galactose-1-phosphate guanylyltransferase (E.C. 2.7.n.n; e.g., *Arabidopsis thaliana* VTC2), L-galactose 1-phosphate phosphatase (E.C. 3.1.3.n; e.g., *Arabidopsis thaliana* VTC4). In one embodiment, the invention provides an engineered and/or evolved methylotroph comprising one or more exogenous proteins from the galactose biosynthetic pathway.

The invention also provides engineered and/or evolved methylotrophs that produce sugar alcohols, such as sorbitol, as the carbon-based product of interest. In certain embodiments, the engineered and/or evolved methylotroph produces D-sorbitol from D-α-glucose and NADPH via the enzyme polyol dehydrogenase (E.C. 1.1.1.21; e.g., *Saccharomyces cerevisiae* GRE3).

The invention also provides engineered and/or evolved methylotrophs that produce sugar derivatives, such as ascorbate, as the carbon-based product of interest. In certain embodiments, the engineered and/or evolved methylotroph produces ascorbate from galactose via the enzymes L-galactose dehydrogenase (E.C. 1.1.1.122; e.g., *Arabidopsis thaliana* At4G33670) and L-galactonolactone oxidase (E.C. 1.3.3.12; e.g., *Saccharomyces cerevisiae* ATGLDH). Optionally, a catalase (E.C. 1.11.1.6; e.g., *E. coli* KatE) may be included to convert the waste produce hydrogen peroxide to molecular oxygen.

The fermentation products according to the above aspect of the invention are sugars, which are exported into the media as a result of C1 metabolism during methylotrophy. The sugars can also be reabsorbed later and fermented, directly separated, or utilized by a co-cultured organism. This approach has several advantages. First, the total amount of sugars the cell can handle is not limited by maximum intracellular concentrations because the end-product is exported to the media. Second, by removing the sugars from the cell, the equilibria of methylotrophic reactions are pushed towards creating more sugar. Third, during methylotrophy, there is no need to push carbon flow towards glycolysis. Fourth, the sugars are potentially less toxic than the fermentation products that would be directly produced.

Methylotrophy may be followed by flux of carbon compounds to the creation and maintenance of biomass and to the storage of retrievable carbon in the form of glycogen, cellulose and/or sucrose. Glycogen is a polymer of glucose composed of linear alpha 1,4-linkages and branched alpha 1,6-linkages. The polymer is insoluble at degree of polymerization (DP) greater than about 60,000 and forms intracellular granules. Glycogen in synthesized in vivo via a pathway originating from glucose 1-phosphate. Its hydrolysis can proceed through phosphorylation to glucose phosphates; via the internal cleavage of polymer to maltodextrins; via the successive exo-cleavage to maltose; or via the concerted hydrolysis of polymer and maltodextrins to maltose and glucose. Hence, an alternative biosynthetic route to glucose and/or maltose is via the hydrolysis of glycogen which can optionally be exported from the cell as described above. There are a number of potential enzyme candidates for glycogen hydrolysis (Table 1).

In addition to the above, another mechanism is described to produce glucose biosynthetically. In certain embodiments, the present invention provides for cloned genes for glycogen hydrolyzing enzymes to hydrolyze glycogen to glucose and/or maltose and transport maltose and glucose from the cell. Exemplary enzymes are set forth below in Table 1. Glucose is transported from the engineered and/or evolved methylotroph by a glucose/hexose transporter. This alternative allows the cell to accumulate glycogen naturally but adds enzyme activities to continuously return it to maltose or glucose units that can be collected as a carbon-based product.

TABLE 1

Enzymes for hydrolysis of glycogen

| Enzyme | EC. number | Function |
|---|---|---|
| α-amylase | 3.2.1.1 | endohydrolysis of 1,4-α-D-glucosidic linkages in polysaccharides |
| β-amylase | 3.2.1.2 | hydrolysis of 1,4-α-D-glucosidic linkages in polysaccharides so as to remove successive maltose units from the non-reducing ends of the chains |
| γ-amylase | 3.2.1.3 | hydrolysis of terminal 1,4-linked α-D-glucose residues successively from non-reducing ends of the chains with release of β-D-glucose |
| glucoamylase | 3.2.1.3 | hydrolysis of terminal 1,4-linked α-D-glucose residues successively from non-reducing ends of the chains with release of β-D-glucose |
| isoamylase | 3.2.1.68 | hydrolysis of (1->6)-α-D-glucosidic branch linkages in glycogen, amylopectin and their beta-limit dextrins |
| pullulanase | 3.2.1.41 | hydrolysis of (1->6)-α-D-glucosidic linkages in pullulan [a linear polymer of α-(1->6)-linked maltotriose units] and in amylopectin and glycogen, and the α- and β-limit dextrins of amylopectin and glycogen |

TABLE 1-continued

Enzymes for hydrolysis of glycogen

| Enzyme | EC. number | Function |
|---|---|---|
| amylomaltase | 2.4.1.25 | transfers a segment of a 1,4-α-D-glucan to a new position in an acceptor, which may be glucose or a 1,4-α-D-glucan (part of yeast debranching system) |
| amylo-α-1,6-glucosidase | 3.2.1.33 | debranching enzyme; hydrolysis of (1–>6)-α-D-glucosidic branch linkages in glycogen phosphorylase limit dextrin |
| phosphorylase kinase | 2.7.11.19 | 2 ATP + phosphorylase b = 2 ADP + phosphorylase a |
| phosphorylase | 2.4.1.1 | $(1,4\text{-}\alpha\text{-D-glucosyl})_n$ + phosphate = $(1,4\text{-}\alpha\text{-D-glucosyl})_{n-1}$ + α-D-glucose-1-phosphate |

Production of Fermentative Products as the Carbon-Based Products of Interest

In certain embodiments, the engineered and/or evolved methylotroph of the present invention produces alcohols such as ethanol, propanol, isopropanol, butanol and fatty alcohols as the carbon-based products of interest.

Figure 10:
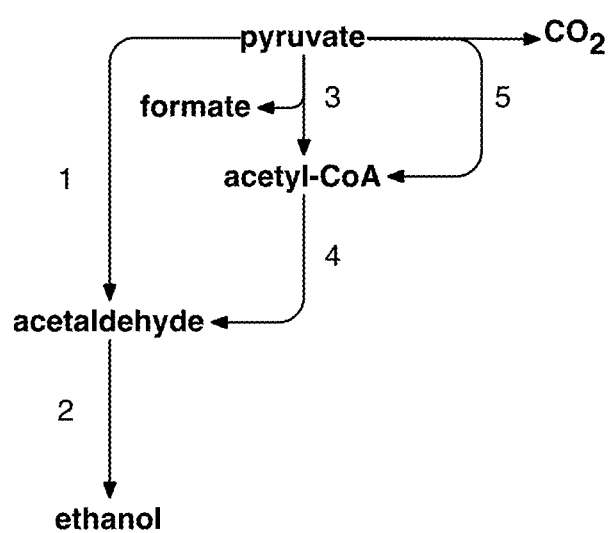
FIG. 10 depicts different fermentation pathways from pyruvate to ethanol. Each reaction is numbered. Enzymes catalyzing each reaction are as follows: 1, pyruvate decarboxylase (E.C. 4.1.1.1); 2, alcohol dehydrogenase (E.C. 1.1.1.1); 3, pyruvate-formate lyase (E.C. 2.3.1.54); 4, acetaldehyde dehydrogenase (E.C. 1.2.1.10); 5, pyruvate synthase (E.C. 1.2.7.1).

In some embodiments, the engineered and/or evolved methylotroph of the present invention is engineered to produce ethanol via pyruvate fermentation. Pyruvate fermentation to ethanol is well know to those in the art and there are several pathways including the pyruvate decarboxylase pathway, the pyruvate synthase pathway and the pyruvate formate-lyase pathway (FIG. 10). The reactions in the pyruvate decarboxylase pathway are catalyzed by the following enzymes: pyruvate decarboxylase (E.C. 4.1.1.1) and alcohol dehydrogenase (E.C. 1.1.1.1 or E.C. 1.1.1.2). The reactions in the pyruvate synthase pathway are catalyzed by the following enzymes: pyruvate synthase (E.C. 1.2.7.1), acetaldehyde dehydrogenase (E.C. 1.2.1.10 or E.C. 1.2.1.5), and alcohol dehydrogenase (E.C. 1.1.1.1 or E.C. 1.1.1.2). The reactions in the pyruvate formate-lyase pathway are catalyzed by the following enzymes: pyruvate formate-lyase (E.C. 2.3.1.54), acetaldehyde dehydrogenase (E.C. 1.2.1.10 or E.C. 1.2.1.5), and alcohol dehydrogenase (E.C. 1.1.1.1 or E.C. 1.1.1.2).

In some embodiments, the engineered and/or evolved methylotroph of the present invention is engineered to produce lactate via pyruvate fermentation. Lactate dehydrogenase (E.C. 1.1.1.28) converts NADH and pyruvate to D-lactate. Exemplary enzymes include E. coli ldhA.

Currently, fermentative products such as ethanol, butanol, lactic acid, formate, acetate produced in biological organisms employ a NADH-dependent processes. However, depending on the metabolism of the engineered and/or evolved methylotroph, the cell may produce NADPH or reduced ferredoxin as the reducing cofactor. NADPH is used mostly for biosynthetic operations in biological organisms, e.g., cell for growth, division, and for building up chemical stores, such as glycogen, sucrose, and other macromolecules. Using natural or engineered enzymes that utilize NADPH or reduced ferredoxin as a source of reducing power instead of NADH would allow direct use of methylotrophic reducing power towards formation of normally fermentative byproducts. Accordingly, the present invention provides methods for producing fermentative products such as ethanol by expressing NADP+-dependent or ferredoxin-dependent enzymes. NADP+-dependent enzymes include alcohol dehydrogenase [NADP+] (E.C. 1.1.1.2) and acetaldehyde dehydrogenase [NAD(P)+] (E.C. 1.2.1.5). Exemplary NADP+-dependent alcohol dehydrogenases include Moorella sp. HUC22-1 AdhA (YP_430754) [Inokuma, 2007], and homologs thereof.

In addition to providing exogenous genes or endogenous genes with novel regulation, the optimization of ethanol production in engineered and/or evolved methylotrophs sometimes requires the elimination or attenuation of certain host enzyme activities. These include, but are not limited to, pyruvate oxidase (E.C. 1.2.2.2), D-lactate dehydrogenase (E.C. 1.1.1.28), acetate kinase (E.C. 2.7.2.1), phosphate acetyltransferase (E.C. 2.3.1.8), citrate synthase (E.C. 2.3.3.1), phosphoenolpyruvate carboxylase (E.C. 4.1.1.31). The extent to which these manipulations are necessary is determined by the observed byproducts found in the bioreactor or shake-flask. For instance, observation of acetate would suggest deletion of pyruvate oxidase, acetate kinase, and/or phosphotransacetylase enzyme activities. In another example, observation of D-lactate would suggest deletion of D-lactate dehydrogenase enzyme activities, whereas observation of succinate, malate, fumarate, oxaloacetate, or citrate would suggest deletion of citrate synthase and/or PEP carboxylase enzyme activities.

Production of Ethylene, Propylene, 1-Butene, 1,3-Butadiene, Acrylic Acid, Etc. as the Carbon-Based Products of Interest In certain embodiments, the engineered and/or evolved methylotroph of the present invention produces ethylene, propylene, 1-butene, 1,3-butadiene and acrylic acid as the carbon-based products of interest. Ethylene and/or propylene may be produced by either (1) the dehydration of ethanol or propanol (E.C. 4.2.1.-), respectively or (2) the decarboxylation of acrylate or crotonate (E.C. 4.1.1.-), respectively. While many dehydratases exist in nature, none has been shown to convert ethanol to ethylene (or propanol to propylene, propionic acid to acrylic acid, etc.) by dehydration. Genes encoding enzymes in the 4.2.1.x or 4.1.1.x group can be identified by searching databases such as GenBank using the methods described above, expressed in any desired host (such as Escherichia coli, for simplicity), and that host can be assayed for the appropriate enzymatic activity. A high-throughput screen is especially useful for screening many genes and variants of genes generated by mutagenesis (i.e., error-prone PCR, synthetic libraries, chemical mutagenesis, etc.).

The ethanol dehydratase gene, after development to a suitable level of activity, can then be expressed in an ethanologenic organism to enable that organism to produce ethylene. For instance, coexpress native or evolved ethanol dehydratase gene into an organism that already produces ethanol, then test a culture by GC analysis of offgas for ethylene production that is significantly higher than without the added gene or via a high-throughput assay adapted from a colorimetric test [Larue, 1973]. It may be desirable to eliminate ethanol-export proteins from the production organism to prevent ethanol from being secreted into the medium and preventing its conversion to ethylene.

Alternatively, acryloyl-CoA can be produced as described above, and acryloyl-CoA hydrolases (E.C. 3.1.2.-), such as the acuNgene from *Halomonas* sp. HTNK1, can convert acryloyl-CoA into acrylate, which can be thermally decarboxylated to yield ethylene.

Alternatively, genes encoding ethylene-forming enzyme activities (EfE, E.C. 1.14.17.4) from various sources are expressed. Exemplary enzymes include *Pseudomonas syringae* pv. *Phaseolicola* (BAA02477), *P. syringae* pv. *Pisi* (AAD16443), *Ralstonia solanacearum* (CAD18680). Optimizing production may require further metabolic engineering (improving production of alpha-ketogluterate, recycling succinate as two examples).

In some embodiments, the engineered and/or evolved methylotroph of the present invention is engineered to produce ethylene from methionine. The reactions in the ethylene biosynthesis pathway are catalyzed by the following enzymes: methionine adenosyltransferase (E.C. 2.5.1.6), 1-aminocyclopropane-1-carboxylate synthase (E.C. 4.4.1.14) and 1-aminocyclopropane-1-carboxylate oxidase (E.C. 1.14.17.4).

In some embodiments, the engineered and/or evolved methylotroph of the present invention is engineered to produce propylene as the carbon-based product of interest. In one embodiment, the engineered and/or evolved methylotroph is engineered to express one or more of the following enzymes: propionyl-CoA synthase (E.C. 6.2.1.-, E.C. 4.2.1.- and E.C. 1.3.1.-), propionyl-CoA transferase (E.C. 2.8.3.1), aldehyde dehydrogenase (E.C. 1.2.1.3 or E.C. 1.2.1.4), alcohol dehydrogenase (E.C. 1.1.1.1 or E.C. 1.1.1.2), and alcohol dehydratase (E.C. 4.2.1.-). Propionyl-CoA synthase is a multi-functional enzyme that converts 3-hydroxypropionate, ATP and NADPH to propionyl-CoA. Exemplary propionyl-CoA synthases include AAL47820, and homologs thereof. The present invention provides nucleic acids each comprising or consisting of a sequence which is a codon optimized version of the wild-type propionyl-CoA synthase gene. In another embodiment, the invention provides a nucleic acid encoding a polypeptide having the amino acid sequence of SEQ ID NO:5, or a sequence having 70%, 71%, 72%, 73%, 74%, 75%, 76%, 77%, 78%, 79%, 80%, 81-85%, 90-95%, 96-98%, 99%, 99.9% or even higher identity thereto. Propionyl-CoA transferase converts propionyl-CoA and acetate to acetyl-CoA and propionate. Exemplary enzymes include *Ralstonia eutropha* pct and homologs thereof. Aldehyde dehydrogenase converts propionate and NADPH to propanal. Alcohol dehydrogenase converts propanal and NADPH to 1-propanol. Alcohol dehydratase converts 1-propanol to propylene.

In another embodiment, *E. coli* thiolase atoB (E.C. 2.3.1.9) converts 2 acetyl-CoA into acetoacetyl-CoA, and *C. acetobutylicum* hbd (E.C. 1.1.1.157) converts acetoacetyl-CoA and NADH into 3-hydroxybutyryl-CoA. *E. coli* tesB (EC 3.1.2.20) or *C. acetobutylicum* ptb and buk (E.C. 2.3.1.19 and 2.7.2.7 respectively) convert 3-hydroxybutyryl-CoA into 3-hydroxybutyrate, which can be simultaneously decarboxylated and dehydrated to yield propylene. Optionally, the 3-hydroxybutyryl-CoA is polymerized to form poly(3-hydroxybutyrate), a solid compound which can be extracted from the fermentation medium and simultaneously depolymerizied, hydrolyzed, dehydrated, and decarboxyated to yield propylene (U.S. patent application Ser. No. 12/527,714, 2008).

Production of Fatty Acids, their Intermediates and Derivatives as the Carbon-Based Products of Interest In certain embodiments, the engineered and/or evolved methylotroph of the present invention produces fatty acids, their intermediates and their derivatives as the carbon-based products of interest. The engineered and/or evolved methylotrophs of the present invention can be modified to increase the production of acyl-ACP or acyl-CoA, to reduce the catabolism of fatty acid derivatives and intermediates, or to reduce feedback inhibition at specific points in the biosynthetic pathway used for fatty acid products. In addition to modifying the genes described herein, additional cellular resources can be diverted to over-produce fatty acids. For example the lactate, succinate and/or acetate pathways can be attenuated and the fatty acid biosynthetic pathway precursors acetyl-CoA and/or malonyl-CoA can be overproduced.

In one embodiment, the engineered and/or evolved methylotrophs of the present invention can be engineered to express certain fatty acid synthase activities (FAS), which is a group of peptides that catalyze the initiation and elongation of acyl chains [Marrakchi, 2002a]. The acyl carrier protein (ACP) and the enzymes in the FAS pathway control the length, degree of saturation and branching of the fatty acids produced, which can be attenuated or over-expressed. Such enzymes include accABCD, FabD, FabH, FabG, FabA, FabZ, FabI, FabK, FabL, FabM, FabB, FabF, and homologs thereof.

In another embodiment, the engineered and/or evolved methylotrophs of the present invention form fatty acid byproducts through ACP-independent pathways, for example, the pathway described recently by [Dellomonaco, 2011] involving reversal of beta oxidation. Enzymes involved in these pathways include such genes as atoB, fadA, fadB, fadD, fadE, fadI, fadK, fadJ, paaZ, ydiO, yfcY, yfcZ, ydiD, and homologs thereof.

In one aspect, the fatty acid biosynthetic pathway precursors acetyl-CoA and malonyl-CoA can be overproduced in the engineered and/or evolved methylotroph of the present invention. Several different modifications can be made, either in combination or individually, to the host cell to obtain increased acetyl CoA/malonyl CoA/fatty acid and fatty acid derivative production. To modify acetyl-CoA and/or malonyl-CoA production, the expression of acetyl-CoA carboxylase (E.C. 6.4.1.2) can be modulated. Exemplary genes include accABCD (AAC73296) or homologs thereof. To increase acetyl CoA production, the expression of several genes may be altered including pdh, panK, aceEF, (encoding the Elp dehydrogenase component and the E2p dihydrolipoamide acyltransferase component of the pyruvate and 2-oxoglutarate dehydrogenase complexes), fabH/fabD/fabG/acpP/fabF, and in some examples additional nucleic acid encoding fatty-acyl-CoA reductases and aldehyde decarbonylases. Exemplary enzymes include pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), fabF (AAC74179).

Genes to be knocked-out or attenuated include fadE, gpsA, ldhA, pflb, adhE, pta, poxB, ackA, and/or ackB. Exemplary enzymes include fadE (AAC73325), gspA (AAC76632), ldhA (AAC74462), pflb (AAC73989), adhE (AAC74323), pta (AAC75357), poxB (AAC73958), ackA (AAC75356), ackB (BAB81430), and homologs thereof.

Additional potential modifications include the following. To achieve fatty acid overproduction, lipase (E.C. 3.1.1.3) which produce triacylglyerides from fatty acids and glycerol and in some cases serves as a suppressor of fabA can be included in the engineered and/or evolved methylotroph of the present invention. Exemplary enzymes include *Saccharomyces cerevisiae* LipA (CAA89087), *Saccharomyces cerevisiae* TGL2 CAA98876, and homologs thereof. To remove limitations on the pool of acyl-CoA, the D311E mutation in plsB (AAC77011) can be introduced.

To engineer an engineered and/or evolved methylotroph for the production of a population of fatty acid derivatives with homogeneous chain length, one or more endogenous genes can be attenuated or functionally deleted and one or more thioesterases can be expressed. Thioesterases (E.C. 3.1.2.14) generate acyl-ACP from fatty acid and ACP. For example, C10 fatty acids can be produced by attenuating endogenous C18 thioesterases (for example, *E. coli* tesA AAC73596 and P0ADA1, and homologs thereof), which uses C18:1-ACP, and expressing a C10 thioesterase, which uses C10-ACP, thus, resulting in a relatively homogeneous population of fatty acids that have a carbon chain length of 10. In another example, C14 fatty acid derivatives can be produced by attenuating endogenous thioesterases that produce non-C14 fatty acids and expressing the C14 thioesterase, which uses C14-ACP. In yet another example, C12 fatty acid derivatives can be produced by expressing thioesterases that use C12-ACP and attenuating thioesterases that produce non-C12 fatty acids. Exemplary C8:0 to C10:0 thioesterases include *Cuphea hookeriana* fatB2 (AAC49269) and homologs thereof. Exemplary C12:0 thioesterases include *Umbellularia california* fatB (Q41635) and homologs thereof. Exemplary C14:0 thioesterases include *Cinnamonum camphorum* fatB (Q39473). Exemplary C14:0 to C16:0 thioesterases include *Cuphea hookeriana* fatB3 (AAC49269). Exemplary C16:0 thioesterases includeArabidopsis *thaliana* fatB (CAA85388), *Cuphea hookeriana* fatB1 (Q39513) and homologs thereof. Exemplary C18:1 thioesterases include *Arabidopsis thaliana* fatA (NP_189147, NP_193041), *Arabidopsis thaliana* fatB (CAA85388), *Bradyrhizobium japonicum* fatA (CAC39106), *Cuphea hookeriana* fatA (AAC72883), *Escherichia coli* tesA (NP_415027) and homologs thereof. Acetyl CoA, malonyl CoA, and fatty acid overproduction can be verified using methods known in the art, for example by using radioactive precursors, HPLC, and GC-MS subsequent to cell lysis.

In yet another aspect, fatty acids of various lengths can be produced in the engineered and/or evolved methylotroph by expressing or overexpressing acyl-CoA synthase peptides (E.C. 2.3.1.86), which catalyzes the conversion of fatty acids to acyl-CoA. Some acyl-CoA synthase peptides, which are non-specific, accept other substrates in addition to fatty acids.

In yet another aspect, branched chain fatty acids, their intermediates and their derivatives can be produced in the engineered and/or evolved methylotroph as the carbon-based products of interest. By controlling the expression of endogenous and heterologous enzymes associated with branched chain fatty acid biosynthesis, the production of branched chain fatty acid intermediates including branched chain fatty acids can be enhanced. Branched chain fatty acid production can be achieved through the expression of one or more of the following enzymes [Kaneda, 1991]: branched chain amino acid aminotransferase to produce α-ketoacids from branched chain amino acids such as isoleucine, leucine and valine (E.C. 2.6.1.42), branched chain α-ketoacid dehydrogenase complexes which catalyzes the oxidative decarboxylation of α-ketoacids to branched chain acyl-CoA (bkd, E.C. 1.2.4.4) [Denoya, 1995], dihydrolipoyl dehydrogenase (E.C. 1.8.1.4), beta-ketoacyl-ACP synthase with branched chain acyl CoA specificity (E.C. 2.3.1.41) [Li, 2005], crotonyl-CoA reductase (E.C. 1.3.1.8, 1.3.1.85 or 1.3.1.86) [Han, 1997], and isobutyryl-CoA mutase (large subunit E.C. 5.4.99.2 and small subunit E.C. 5.4.99.13). Exemplary branched chain amino acid aminotransferases include *E. coli* ilvE (YP_026247), *Lactococcus lactis* ilvE (AAF34406), *Pseudomonas putida* ilvE (NP_745648), *Streptomyces coelicolor* ilvE (NP_629657), and homologs thereof. Branched chain α-ketoacid dehydrogenase complexes consist of E1α/β (decarboxylase), E2 (dihydrolipoyl transacylase) and E3 (dihydrolipoyl dehydrogenase) subunits. The industrial host *E. coli* has only the E3 component as a part of its pyruvate dehydrogenase complex (lpd, E.C. 1.8.1.4, NP_414658) and so it requires the E1α/β and E2 bkd proteins. Exemplary α-ketoacid dehydrogenase complexes include *Streptomyces coelicolor* bkdA1 (NP_628006) E1α (decarboxylase component), *S. coelicolor* bkdB2 (NP_628005) E1β (decarboxylase component), *S. coelicolor* bkdA3 (NP_638004) E2 (dihydrolipoyl transacylase); or *S. coelicolor* bkdA2 (NP_733618) E1α (decarboxylase component), *S. coelicolor* bkdB2 (NP_628019) E1β (decarboxylase component), *S. coelicolor* bkdC2 (NP_628018) E2 (dihydrolipoyl transacylase); or *S. avermitilis* bkdA (BAC72074) E1α (decarboxylase component), *S. avermitilis* bkdB (BAC72075) E1β (decarboxylase component), *S. avermitilis* bkdC (BAC72076) E2 (dihydrolipoyl transacylase); *S. avermitilis* bkdF (E.C. 1.2.4.4, BAC72088) E1α (decarboxylase component), *S. avermitilis* bkdG (BAC72089) E1β (decarboxylase component), *S. avermitilis* bkdH (BAC72090) E2 (dihydrolipoyl transacylase); *B. subtilis* bkdAA (NP_390288) E1α (decarboxylase component), *B. subtilis* bkdAB (NP_390288) E1β (decarboxylase component), *B. subtilis* bkdB (NP_390288) E2 (dihydrolipoyl transacylase); or *P. putida* bkdA1 (AAA65614) E1α (decarboxylase component), *P. putida* bkdA2 (AAA65615) E1β (decarboxylase component), *P. putida* bkdC (AAA65617) E2 (dihydrolipoyl transacylase); and homologs thereof. An exemplary dihydrolipoyl dehydrogenase is *E. coli* lpd (NP_414658) E3 and homologs thereof. Exemplary beta-ketoacyl-ACP synthases with branched chain acyl CoA specificity include *Streptomyces coelicolor* fabH1 (NP_626634), ACP (NP_626635) and fabF (NP_626636); *Streptomyces avermitilis* fabH3 (NP_823466), fabC3 (NP_823467), fabF (NP_823468); *Bacillus subtilis* fabH_A (NP_389015), fabH_B (NP_388898), ACP (NP_389474), fabF (NP_389016); *Stenotrophomonas maltophilia* SmalDRAFT 0818 (ZP_01643059), SmalDRAFT_0821 (ZP_01643063), SmalDRAFT 0822 (ZP_01643064); *Legionella pneumophila* fabH (YP_123672), ACP (YP_123675), fabF (YP_123676); and homologs thereof. Exemplary crotonyl-CoA reductases include *Streptomyces coelicolor* ccr (NP_630556), *Streptomyces cinnamonensis* ccr (AAD53915), and homologs thereof. Exemplary isobutyryl-CoA mutases include *Streptomyces coelicolor* icmA & icmB (NP_629554 and NP_630904), *Streptomyces cinnamonensis* icmA and icmB (AAC08713 and AJ246005), and homologs thereof. Additionally or alternatively, endogenous genes that normally lead to straight chain fatty acids, their intermediates, and derivatives may be attenuated or deleted to eliminate competing pathways. Enzymes that interfere with production of branched chain fatty acids include β-ketoacyl-ACP synthase II (E.C. 2.3.1.41) and β-ketoacyl-ACP synthase III (E.C. 2.3.1.41) with straight chain acyl CoA specificity. Exemplary enzymes for deletion include *E. coli* fabF (NP_415613) and fabH (NP_415609).

In yet another aspect, fatty acids, their intermediates and their derivatives with varying degrees of saturation can be produced in the engineered and/or evolved methylotroph as the carbon-based products of interest. In one aspect, hosts are engineered to produce unsaturated fatty acids by over-expressing β-ketoacyl-ACP synthase I (E.C. 2.3.1.41), or by growing the host at low temperatures (for example less than 37° C.). FabB has preference to cis-δ$^3$decenoyl-ACP and results in unsaturated fatty acid production in *E. coli*. Over-expression of FabB results in the production of a significant percentage of unsaturated fatty acids [de Mendoza, 1983]. These unsaturated fatty acids can then be used as intermediates in hosts that are engineered to produce fatty acids derivatives, such as fatty alcohols, esters, waxes, olefins, alkanes, and the like. Alternatively, the repressor of fatty acid biosynthesis, *E. coli* FabR (NP_418398), can be deleted, which can also result in increased unsaturated fatty acid production in *E. coli* [Zhang, 2002]. Further increase in unsaturated fatty acids is achieved by over-expression of heterologous trans-2, cis-3-decenoyl-ACP isomerase and controlled expression of trans-2-enoyl-ACP reductase II [Marrakchi, 2002b], while deleting *E. coli* FabI (trans-2-enoyl-ACP reductase, E.C. 1.3.1.9, NP_415804) or homologs thereof in the host organism. Exemplary β-ketoacyl-ACP synthase I include *Escherichia coli* fabB (BAA16180) and homologs thereof. Exemplary trans-2, cis-3-decenoyl-ACP isomerase include *Streptococcus mutans* UA159 FabM (DAA05501) and homologs thereof. Exemplary trans-2-enoyl-ACP reductase II include *Streptococcus pneumoniae* R6 FabK (NP_357969) and homologs thereof. To increase production of monounsaturated fatty acids, the sfa gene, suppressor of FabA, can be over-expressed [Rock, 1996]. Exemplary proteins include AAN79592 and homologs thereof. One of ordinary skill in the art would appreciate that by attenuating fabA, or over-expressing fabB and expressing specific thioesterases (described above), unsaturated fatty acids, their derivatives, and products having a desired carbon chain length can be produced.

In some examples the fatty acid or intermediate is produced in the cytoplasm of the cell. The cytoplasmic concentration can be increased in a number of ways, including, but not limited to, binding of the fatty acid to coenzyme A to form an acyl-CoA thioester. Additionally, the concentration of acyl-CoAs can be increased by increasing the biosynthesis of CoA in the cell, such as by over-expressing genes associated with pantothenate biosynthesis (panD) or knocking out the genes associated with glutathione biosynthesis (glutathione synthase).

Production of Fatty Alcohols as the Carbon-Based Products of Interest

In yet further aspects, hosts cells are engineered to convert acyl-CoA to fatty alcohols by expressing or overexpressing a fatty alcohol forming acyl-CoA reductase (FAR, E.C. 1.1.1.*), or an acyl-CoA reductases (E.C. 1.2.1.50) and alcohol dehydrogenase (E.C. 1.1.1.1) or a combination of the foregoing to produce fatty alcohols from acyl-CoA. Hereinafter fatty alcohol forming acyl-CoA reductase (FAR, E.C. 1.1.1.*), acyl-CoA reductases (E.C. 1.2.1.50) and alcohol dehydrogenase (E.C. 1.1.1.1) are collectively referred to as fatty alcohol forming peptides. Some fatty alcohol forming peptides are non-specific and catalyze other reactions as well: for example, some acyl-CoA reductase peptides accept other substrates in addition to fatty acids. Exemplary fatty alcohol forming acyl-CoA reductases include *Acinetobacter baylyi* ADP1 acr1 (AAC45217), *Simmondsia chinensis* jjfar (AAD38039), *Mus musculus* mfar1 (AAH07178), *Mus musculus* mfar2 (AAH55759), *Acinetobacter* sp. M1 acrM1, *Homo sapiens* hfar (AAT42129), and homologs thereof. Fatty alcohols can be used as surfactants.

Many fatty alcohols are derived from the products of fatty acid biosynthesis. Hence, the production of fatty alcohols can be controlled by engineering fatty acid biosynthesis in the engineered and/or evolved methylotroph. The chain length, branching and degree of saturation of fatty acids and their intermediates can be altered using the methods described herein, thereby affecting the nature of the resulting fatty alcohols.

As mentioned above, through the combination of expressing genes that support brFA synthesis and alcohol synthesis, branched chain alcohols can be produced. For example, when an alcohol reductase such as Acr1 from *Acinetobacter baylyi* ADP1 is coexpressed with a bkd operon, *E. coli* can synthesize isopentanol, isobutanol or 2-methyl butanol. Similarly, when Acr1 is coexpressed with ccr/icm genes, *E. coli* can synthesize isobutanol.

Production of Fatty Esters as the Carbon-Based Products of Interest

In another aspect, engineered and/or evolved methylotrophs produce various lengths of fatty esters (biodiesel and waxes) as the carbon-based products of interest. Fatty esters can be produced from acyl-CoAs and alcohols. The alcohols can be provided in the fermentation media, produced by the engineered and/or evolved methylotroph itself or produced by a co-cultured organism.

In some embodiments, one or more alcohol O-acetyltransferases is expressed in the engineered and/or evolved methylotroph to produce fatty esters as the carbon-based product of interest. Alcohol O-acetyltransferase (E.C. 2.3.1.84) catalyzes the reaction of acetyl-CoA and an alcohol to produce CoA and an acetic ester. In some embodiments, the alcohol O-acetyltransferase peptides are co-expressed with selected thioesterase peptides, FAS peptides and fatty alcohol forming peptides to allow the carbon chain length, saturation and degree of branching to be controlled. In other embodiments, the bkd operon can be co-expressed to enable branched fatty acid precursors to be produced.

Alcohol O-acetyltransferase peptides catalyze other reactions such that the peptides accept other substrates in addition to fatty alcohols or acetyl-CoA thioester. Other substrates include other alcohols and other acyl-CoA thioesters. Modification of such enzymes and the development of assays for characterizing the activity of a particular alcohol O-acetyltransferase peptides are within the scope of a skilled artisan. Engineered O-acetyltransferases and O-acyltransferases can be created that have new activities and specificities for the donor acyl group or acceptor alcohol moiety.

Alcohol acetyl transferases (AATs, E.C. 2.3.1.84), which are responsible for acyl acetate production in various plants, can be used to produce medium chain length waxes, such as octyl octanoate, decyl octanoate, decyl decanoate, and the like. Fatty esters, synthesized from medium chain alcohol (such as C6, C8) and medium chain acyl-CoA (or fatty acids, such as C6 or C8) have a relative low melting point. For example, hexyl hexanoate has a melting point of −55° C. and octyl octanoate has a melting point of −18 to −17° C. The low melting points of these compounds make them good candidates for use as biofuels. Exemplary alcohol acetyltransferases include *Fragaria x ananassa* SAAT (AAG13130) [Aharoni, 2000], *Saccharomyces cerevisiae* Atfp1 (NP_015022), and homologs thereof.

In some embodiments, one or more wax synthases (E.C. 2.3.1.75) is expressed in the engineered and/or evolved methylotroph to produce fatty esters including waxes from acyl-CoA and alcohols as the carbon-based product of interest. Wax synthase peptides are capable of catalyzing the conversion of an acyl-thioester to fatty esters. Some wax synthase peptides can catalyze other reactions, such as converting short chain acyl-CoAs and short chain alcohols to produce fatty esters. Methods to identify wax synthase activity are provided in U.S. Pat. No. 7,118,896, which is herein incorporated by reference. Medium-chain waxes that have low melting points, such as octyl octanoate and octyl decanoate, are good candidates for biofuel to replace triglyceride-based biodiesel. Exemplary wax synthases include *Acinetobacter* baylyi ADP1 wsadp1, *Acinetobacter* baylyi ADP1 wax-dgaT (AAO17391) [Kalscheuer, 2003], *Saccharomyces cerevisiae* Eeb1 (NP_015230), *Saccharomyces cerevisiae* YMR210w (NP_013937), *Simmondsia chinensis* acyltransferase (AAD38041), *Mus musculus* Dgat214 (Q6E1M8), and homologs thereof.

In other aspects, the engineered and/or evolved methylotrophs are modified to produce a fatty ester-based biofuel by expressing nucleic acids encoding one or more wax ester synthases in order to confer the ability to synthesize a saturated, unsaturated, or branched fatty ester. In some embodiments, the wax ester synthesis proteins include, but are not limited to: fatty acid elongases, acyl-CoA reductases, acyltransferases or wax synthases, fatty acyl transferases, diacylglycerol acyltransferases, acyl-coA wax alcohol acyltransferases, bifunctional wax ester synthase/acyl-CoA: diacylglycerol acyltransferase selected from a multienzyme complex from *Simmondsia chinensis, Acinetobacter* sp. strain ADP1 (formerly *Acinetobacter calcoaceticus* ADP1), *Pseudomonas aeruginosa, Fundibacter jadensis, Arabidopsis thaliana*, or *Alkaligenes eutrophus*. In one embodiment, the fatty acid elongases, acyl-CoA reductases or wax synthases are from a multienzyme complex from *Alkaligenes eutrophus* and other organisms known in the literature to produce wax and fatty acid esters.

Many fatty esters are derived from the intermediates and products of fatty acid biosynthesis. Hence, the production of fatty esters can be controlled by engineering fatty acid biosynthesis in the engineered and/or evolved methylotroph. The chain length, branching and degree of saturation of fatty acids and their intermediates can be altered using the methods described herein, thereby affecting the nature of the resulting fatty esters.

Additionally, to increase the percentage of unsaturated fatty acid esters, the engineered and/or evolved methylotroph can also overexpress Sfa which encodes a suppressor of fabA (AAN79592, AAC44390), β-ketoacyl-ACP synthase I (E.C. 2.3.1.41, BAA16180), and secG null mutant suppressors (cold shock proteins) gnsA and gnsB (ABD18647 and AAC74076). In some examples, the endogenous fabF gene can be attenuated, thus, increasing the percentage of palmitoleate (C 16:1) produced.

Optionally a wax ester exporter such as a member of the FATP family is used to facilitate the release of waxes or esters into the extracellular environment from the engineered and/or evolved methylotroph. An exemplary wax ester exporter that can be used is fatty acid (long chain) transport protein CG7400-PA, isoform A from *D. melanogaster* (NP_524723), or homologs thereof.

The centane number (CN), viscosity, melting point, and heat of combustion for various fatty acid esters have been characterized in for example, [Knothe, 2005]. Using the teachings provided herein the engineered and/or evolved methylotroph can be engineered to produce any one of the fatty acid esters described in [Knothe, 2005].

Production of Alkanes as the Carbon-Based Products of Interest

In another aspect, engineered and/or evolved methylotrophs produce alkanes of various chain lengths (hydrocarbons) as the carbon-based products of interest. Many alkanes are derived from the products of fatty acid biosynthesis. Hence, the production of alkanes can be controlled by engineering fatty acid biosynthesis in the engineered and/or evolved methylotroph. The chain length, branching and degree of saturation of fatty acids and their intermediates can be altered using the methods described herein. The chain length, branching and degree of saturation of alkanes can be controlled through their fatty acid biosynthesis precursors.

In certain aspects, fatty aldehydes can be converted to alkanes and CO in the engineered and/or evolved methylotroph via the expression of decarbonylases [Cheesbrough, 1984; Dennis, 1991]. Exemplary enzymes include *Arabidopsis thaliana* cer1 (NP_171723), *Oryza sativacer*1 CER1 (AAD29719) and homologs thereof.

In another aspect, fatty alcohols can be converted to alkanes in the engineered and/or evolved methylotroph via the expression of terminal alcohol oxidoreductases as in *Vibrio furnissii* M1 [Park, 2005].

Production of Olefins as the Carbon-Based Products of Interest

In another aspect, engineered and/or evolved methylotrophs produce olefins (hydrocarbons) as the carbon-based products of interest. Olefins are derived from the intermediates and products of fatty acid biosynthesis. Hence, the production of olefins can be controlled by engineering fatty acid biosynthesis in the engineered and/or evolved methylotroph. Introduction of genes affecting the production of unsaturated fatty acids, as described above, can result in the production of olefins. Similarly, the chain length of olefins can be controlled by expressing, overexpressing or attenuating the expression of endogenous and heterologous thioesterases which control the chain length of the fatty acids that are precursors to olefin biosynthesis. Also, by controlling the expression of endogenous and heterologous enzymes associated with branched chain fatty acid biosynthesis, the production of branched chain olefins can be enhanced. Methods for controlling the chain length and branching of fatty acid biosynthesis intermediates and products are described above. Olefins can be obtained by downstreaming processing of 3-hydroxy alkanoates as taught by Fischer et al. [Ind Eng Chem Res, 2011, 50(8):4420-4424, DOI: 10.1021/ie1023386]. Accordingly, the fermentation product for methylotrophic production of olefins need not be an olefin itself.

Production of ω-Cyclic Fatty Acids and their Derivatives as the Carbon-Based Products of Interest In another aspect, the engineered and/or evolved methylotroph of the present invention produces ω-cyclic fatty acids (cyFAs) as the carbon-based product of interest. To synthesize ω-cyclic fatty acids (cyFAs), several genes need to be introduced and expressed that provide the cyclic precursor cyclohexylcarbonyl-CoA [Cropp, 2000]. The genes (fabH, ACP and fabF) can then be expressed to allow initiation and elongation of ω-cyclic fatty acids. Alternatively, the homologous genes can be isolated from microorganisms that make cyFAs and expressed in *E. coli*. Relevant genes include bkdC, lpd, fabH, ACP, fabF, fabH1, ACP, fabF, fabH3, fabC3, fabF, fabH_A, fabH_B, ACP.

Expression of the following genes are sufficient to provide cyclohexylcarbonyl-CoA in *E. coli*: ansJ, ansK, ansL, chcA (1-cyclohexenylcarbonyl CoA reductase) and ansM from the ansatrienin gene cluster of *Streptomyces collinus* [Chen, 1999] or plmJK (5-enolpyruvylshikimate-3-phosphate synthase), plmL (acyl-CoA dehydrogenase), chcA (enoyl-(ACP) reductase) and plmM (2,4-dienoyl-CoA reductase) from the phoslactomycin B gene cluster of *Streptomyces* sp. HK803 [Palaniappan, 2003] together with the acyl-CoA isomerase (chcB gene) [Patton, 2000] from *S. collinus, S. avermitilis* or *S. coelicolor*. Exemplary ansatrienin gene cluster enzymes include AAC44655, AAF73478 and homologs thereof. Exemplary phoslactomycin B gene cluster enzymes include AAQ84158, AAQ84159, AAQ84160, AAQ84161 and homologs thereof. Exemplary chcB enzymes include NP_629292, AAF73478 and homologs thereof.

The genes (fabH, ACP and fabF) are sufficient to allow initiation and elongation of ω-cyclic fatty acids, because they can have broad substrate specificity. In the event that coexpression of any of these genes with the ansJKLM/chcAB or pmlJKLM/chcAB genes does not yield cyFAs, fabH, ACP and/or fabF homologs from microorganisms that make cyFAs can be isolated (e.g., by using degenerate PCR primers or heterologous DNA probes) and coexpressed.

Production of Halogenated Derivatives of Fatty Acids

Genes are known that can produce fluoroacetyl-CoA from fluoride ion. In one embodiment, the present invention allows for production of fluorinated fatty acids by combining expression of fluoroacetate-involved genes (e.g., fluorinase, nucleotide phosphorylase, fluorometabolite-specific aldolases, fluoroacetaldehyde dehydrogenase, and fluoroacetyl-CoA synthase).

Transport/Efflux/Release of Fatty Acids and their Derivatives

Also disclosed herein is a system for continuously producing and exporting hydrocarbons out of recombinant host microorganisms via a transport protein. Many transport and efflux proteins serve to excrete a large variety of compounds and can be evolved to be selective for a particular type of fatty acid. Thus, in some embodiments an ABC transporter can be functionally expressed by the engineered and/or evolved methylotroph, so that the organism exports the fatty acid into the culture medium. In one example, the ABC transporter is an ABC transporter from *Caenorhabditis elegans, Arabidopsis thalania, Alkaligenes eutrophus* or *Rhodococcus erythropolis* or homologs thereof. Exemplary transporters include AAU44368, NP_188746, NP_175557, AAN73268 or homologs thereof.

The transport protein, for example, can also be an efflux protein selected from: AcrAB (NP_414996.1, NP_414995.1), ToIC (NP_417507.2) and AcrEF (NP_417731.1, NP_417732.1) from *E. coli*, or t1111618 (NP_682408), t111619 (NP_682409), t110139 (NP_680930), H11619 and U10139 from *Thermosynechococcus elongatus* BP-I or homologs thereof.

In addition, the transport protein can be, for example, a fatty acid transport protein (FATP) selected from *Drosophila melanogaster, Caenorhabditis elegans, Mycobacterium tuberculosis* or *Saccharomyces cerevisiae, Acinetobacter* sp. H01-N, any one of the mammalian FATPs or homologs thereof. The FATPs can additionally be resynthesized with the membranous regions reversed in order to invert the direction of substrate flow. Specifically, the sequences of amino acids composing the hydrophilic domains (or membrane domains) of the protein can be inverted while maintaining the same codons for each particular amino acid. The identification of these regions is well known in the art.

Production of Isoprenoids as the Carbon-Based Products of Interest

Figure 11:
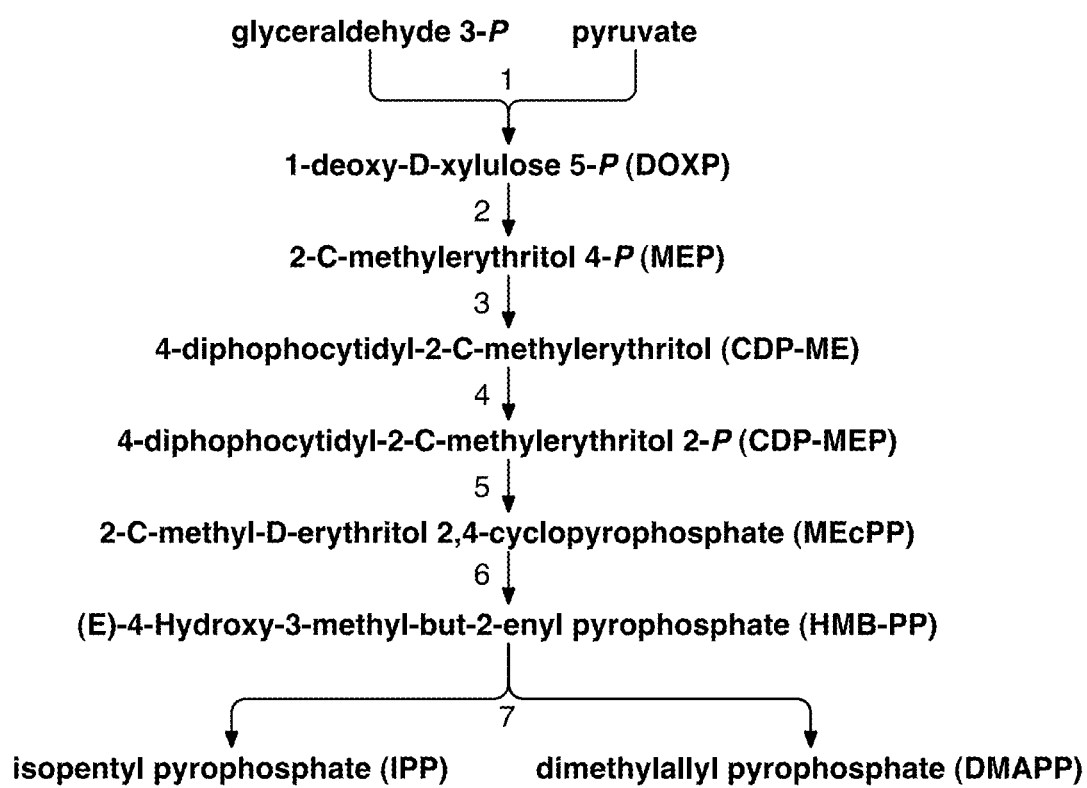
FIG. 11 depicts the metabolic reactions of the mevalonate-independent pathway (also known as the non-mevalonate pathway or deoxyxylulose 5-phosphate (DXP) pathway) for production of isopentenyl pyrophosphate (IPP) and its isomer dimethylallyl pyrophosphate (DMAPP). In metabolite names, —P denotes phosphate. Each reaction is numbered. Enzymes catalyzing each reaction are as follows: 1, 1-deoxy-D-xylulose-5-phosphate synthase (E.C. 2.2.1.7); 2, 1-deoxy-D-xylulose-5-phosphate reductoisomerase (E.C. 1.1.1.267); 3, 4-diphosphocytidyl-2C-methyl-D-erythritol synthase (E.C. 2.7.7.60); 4, 4-diphosphocytidyl-2C-methyl-D-erythritol kinase (E.C. 2.7.1.148); 5, 2C-methyl-D-erythritol 2,4-cyclodiphosphate synthase (E.C. 4.6.1.12); 6, (E)-4-hydroxy-3-methylbut-2-enyl diphosphate synthase (E.C. 1.17.7.1); 7, isopentyl/dimethylallyl diphosphate synthase or 4-hydroxy-3-methylbut-2-enyl diphosphate reductase (E.C. 1.17.1.2).
Figure 12:
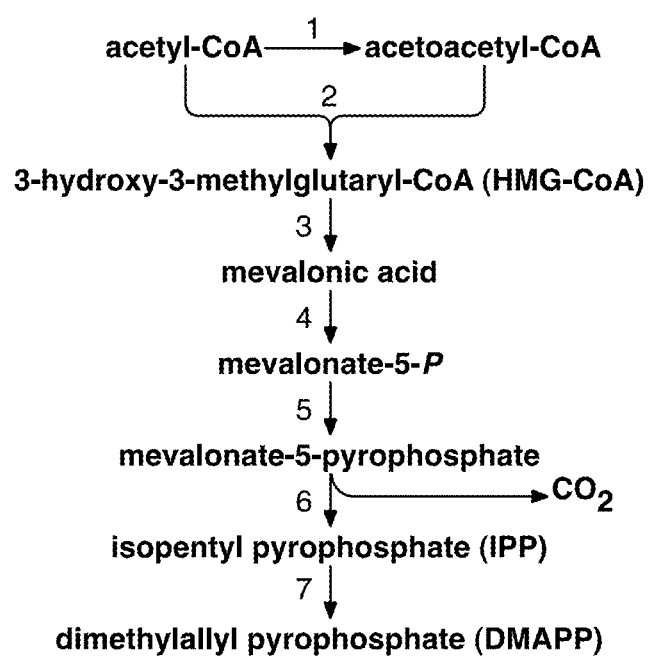
FIG. 12 depicts the metabolic reactions of the mevalonate pathway (also known as the HMG-CoA reductase pathway) for production of isopentenyl pyrophosphate (IPP) and its isomer dimethylallyl pyrophosphate (DMAPP). In metabolite names, —P denotes phosphate. Each reaction is numbered. Enzymes catalyzing each reaction are as follows: 1, acetyl-CoA thiolase; 2, HMG-CoA synthase (E.C. 2.3.3.10); 3, HMG-CoA reductase (E.C. 1.1.1.34); 4, mevalonate kinase (E.C. 2.7.1.36); 5, phosphomevalonate kinase (E.C. 2.7.4.2); 6, mevalonate pyrophosphate decarboxylase (E.C. 4.1.1.33); 7, isopentenyl pyrophosphate isomerase (E.C. 5.3.3.2).

In one aspect, the engineered and/or evolved methylotroph of the present invention produces isoprenoids or their precursors isopentenyl pyrophosphate (IPP) and its isomer, dimethylallyl pyrophosphate (DMAPP) as the carbon-based products of interest. There are two known biosynthetic pathways that synthesize IPP and DMAPP. Prokaryotes, with some exceptions, use the mevalonate-independent or deoxyxylulose 5-phosphate (DXP) pathway to produce IPP and DMAPP separately through a branch point (FIG. 11). Eukaryotes other than plants use the mevalonate-dependent (MEV) isoprenoid pathway exclusively to convert acetyl-coenzyme A (acetyl-CoA) to IPP, which is subsequently isomerized to DMAPP (FIG. 12). In general, plants use both the MEV and DXP pathways for IPP synthesis.

The reactions in the DXP pathway are catalyzed by the following enzymes: 1-deoxy-D-xylulose-5-phosphate synthase (E.C. 2.2.1.7), 1-deoxy-D-xylulose-5-phosphate reductoisomerase (E.C. 1.1.1.267), 4-diphosphocytidyl-2C-methyl-D-erythritol synthase (E.C. 2.7.7.60), 4-diphosphocytidyl-2C-methyl-D-erythritol kinase (E.C. 2.7.1.148), 2C-methyl-D-erythritol 2,4-cyclodiphosphate synthase (E.C. 4.6.1.12), (E)-4-hydroxy-3-methylbut-2-enyl diphosphate synthase (E. C. 1.17.7.1), isopentyl/dimethylallyl diphosphate synthase or 4-hydroxy-3-methylbut-2-enyl diphosphate reductase (E.C. 1.17.1.2). In one embodiment, the engineered and/or evolved methylotroph of the present invention expresses one or more enzymes from the DXP pathway. For example, one or more exogenous proteins can be selected from 1-deoxy-D-xylulose-5-phosphate reductoisomerase, 4-diphosphocytidyl-2C-methyl-D-erythritol synthase, 4-diphosphocytidyl-2C-methyl-D-erythritol kinase, 2C-methyl-D-erythritol 2,4-cyclodiphosphate synthase, (E)-4-hydroxy-3-methylbut-2-enyl diphosphate synthase, and 4-hydroxy-3-methylbut-2-enyl diphosphate reductase. The host organism can also express two or more, three or more, four or more, and the like, including up to all the protein and enzymes that confer the DXP pathway. Exemplary 1-deoxy-D-xylulose-5-phosphate synthases include *E. coli* Dxs (AAC46162); *P. putida* KT2440 Dxs (AAN66154); *Salmonella enterica* Paratyphi, see ATCC 9150 Dxs (AAV78186); *Rhodobacter sphaeroides* 2.4.1 Dxs (YP_353327); *Rhodopseudomonas palustris* CGA009 Dxs (NP_946305); *Xylella fastidiosa Temeculal* Dxs (NP_779493); *Arabidopsis thaliana* Dxs (NP_001078570 and/or NP_196699); and homologs thereof. SEQ ID NO: 1 represents the *Paracoccus* codon optimized coding sequence for the *E. coli* dxs gene of the present invention. In one aspect, the invention provides nucleic acid molecules and homologs, variants and derivatives of SEQ ID NO: 1. The nucleic acid sequences can have 70%, 71%, 72%, 73%, 74%, 75%, 76%, 77%, 78%, 79%, 80%, 81-85%, 90-95%, 96-98%, 99%, 99.9% or even higher identity to SEQ ID NO: 1. The present invention provides nucleic acids each comprising or consisting of a sequence which is a codon optimized version of one of the wild-type dxs gene. In another embodiment, the invention provides nucleic acids each encoding a polypeptide having the amino acid sequence of one of AAC46162, YP_353327, AAV78186, YP_353327, NP_946305, NP_779493, NP_001078570, NP_196699, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary 1-deoxy-D-xylulose-5-phosphate reductoisomerases include *E. coli* Dxr (BAA32426); *Arabidopsis thaliana* DXR (AAF73140); *Pseudomonas putida* KT2440 Dxr (NP_743754 and/or Q88MH4); *Streptomyces coelicolor* A3(2) Dxr (NP_629822); *Rhodobacter sphaeroides* 2.4.1 Dxr (YP_352764); *Pseudomonas fluore-* scens PfO-1 Dxr (YP_346389); and homologs thereof. Exemplary 4-diphosphocytidyl-2C-methyl-D-erythritol synthases include *E. coli* IspD (AAF43207); *Rhodobacter sphaeroides* 2.4.1 IspD (YP_352876); *Arabidopsis thaliana* ISPD (NP_565286); *P. putida* KT2440 IspD (NP_743771); and homologs thereof. Exemplary 4-diphosphocytidyl-2C-methyl-D-erythritol kinases include *E. coli* IspE (AAF29530); *Rhodobacter sphaeroides* 2.4.1 IspE (YP_351828); and homologs thereof. Exemplary 2C-methyl-D-erythritol 2,4-cyclodiphosphate synthases include *E. coli* IspF (AAF44656); *Rhodobacter sphaeroides* 2.4.1 IspF (YP_352877); *P. putida* KT2440 IspF (NP_743775); and homologs thereof. Exemplary (E)-4-hydroxy-3-methylbut-2-enyl diphosphate synthase include *E. coli* IspG (AAK53460); *P. putida* KT2440 IspG (NP_743014); *Rhodobacter sphaeroides* 2.4.1 IspG (YP_353044); and homologs thereof. Exemplary 4-hydroxy-3-methylbut-2-enyl diphosphate reductases include *E. coli* IspH (AAL38655); *P. putida* KT2440 IspH (NP_742768); and homologs thereof.

The reactions in the MEV pathway are catalyzed by the following enzymes: acetyl-CoA thiolase, HMG-CoA synthase (E.C. 2.3.3.10), HMG-CoA reductase (E.C. 1.1.1.34), mevalonate kinase (E.C. 2.7.1.36), phosphomevalonate kinase (E.C. 2.7.4.2), mevalonate pyrophosphate decarboxylase (E.C. 4.1.1.33), isopentenyl pyrophosphate isomerase (E.C. 5.3.3.2). In one embodiment, the engineered and/or evolved methylotroph of the present invention expresses one or more enzymes from the MEV pathway. For example, one or more exogenous proteins can be selected from acetyl-CoA thiolase, HMG-CoA synthase, HMG-CoA reductase, mevalonate kinase, phosphomevalonate kinase, mevalonate pyrophosphate decarboxylase and isopentenyl pyrophosphate isomerase. The host organism can also express two or more, three or more, four or more, and the like, including up to all the protein and enzymes that confer the MEV pathway. Exemplary acetyl-CoA thiolases include NC_000913 REGION: 232413 L.2325315, *E. coli*; D49362, *Paracoccus denitrificans*; L20428, *S. cerevisiae*; and homologs thereof. Exemplary HMG-CoA synthases include NC_001145 complement 19061 . . . 20536, *S. cerevisiae*; X96617, *S. cerevisiae*; X83882, *A. thaliana*; AB037907, *Kitasatospora griseola*; BT007302, *H. sapiens*; NC_002758, Locus tag SAV2546, GeneID 1 122571, *S. aureus*; and homologs thereof. Exemplary HMG-CoA reductases include NM_206548, *D. melanogaster*; NC_002758, Locus tag SAV2545, GeneID 1122570, *S. aureus*; NM 204485, *Gallus gallus*; AB015627, *Streptomyces* sp. KO 3988; AF542543, *Nicotiana attenuata*; AB037907, *Kitasatospora griseola*; AX128213, providing the sequence encoding a truncated HMGR, *S. cerevisiae*; NC_001145: complement 115734 . . . 1 18898, *S. cerevisiae*; and homologs thereof. Exemplary mevalonate kinases include L77688, *A. thaliana*; X55875, *S. cerevisiae*; and homologs thereof. Exemplary phosphomevalonate kinases include AF429385, *Hevea brasiliensis*; NM_006556, *H. sapiens*; NC_001145 complement 712315 . . . 713670, *S. cerevisiae*; and homologs thereof. Exemplary mevalonate pyrophosphate decarboxylase include X97557, *S. cerevisiae*; AF290095, *E. faecium*; U49260, *H. sapiens*; and homologs thereof. Exemplary isopentenyl pyrophosphate isomerases include NP_417365, *E. coli* Idi; AAC32209, *Haematococcus pluvialis* Idi; and homologs thereof. SEQ ID NO:2 represents the *Paracoccus* codon optimized coding sequence for the *E. coli* idi gene of the present invention. In one aspect, the invention provides nucleic acid molecules and homologs, variants and derivatives of SEQ ID NO:2. The nucleic acid sequences can have 70%, 71%, 72%, 73%, 74%, 75%, 76%, 77%, 78%, 79%, 80%, 81-85%, 90-95%, 96-98%, 99%, 99.9% or even higher identity to SEQ ID NO:2. The present invention provides nucleic acids each comprising or consisting of a sequence which is a codon optimized version of one of the wild-type idi gene. In another embodiment, the invention provides nucleic acids each encoding a polypeptide having the amino acid sequence of one of NP_417365, AAC32209, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

In some embodiments, the host cell produces IPP via the MEV pathway, either exclusively or in combination with the DXP pathway. In other embodiments, a host cell's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

In some embodiments, the host cell produces IPP via the DXP pathway, either exclusively or in combination with the MEV pathway. In other embodiments, a host cell's MEV pathway is functionally disabled so that the host cell produces IPP exclusively through a heterologously introduced DXP pathway. The MEV pathway can be functionally disabled by disabling gene expression or inactivating the function of one or more of the MEV pathway enzymes.

Provided herein is a method to produce isoprenoids in engineered and/or evolved methylotrophs engineered with the isopentenyl pyrophosphate pathway enzymes. Some examples of isoprenoids include: hemiterpenes (derived from 1 isoprene unit) such as isoprene; monoterpenes (derived from 2 isoprene units) such as myrcene or limonene; sesquiterpenes (derived from 3 isoprene units) such as amorpha-4,11-diene, bisabolene or farnesene; diterpenes (derived from four isoprene units) such as taxadiene; sesterterpenes (derived from 5 isoprene units); triterpenes (derived from 6 isoprene units) such as squalene; sesquarterpenes (derived from 7 isoprene units); tetraterpenes (derived from 8 isoprene units) such as β-carotene or lycopene; and polyterpenes (derived from more than 8 isoprene units) such as polyisoprene. The production of isoprenoids is also described in some detail in the published PCT applications WO2007/139925 and WO/2007/140339.

In another embodiment, the engineered and/or evolved methylotroph of the present invention produces isoprene as the carbon-based product of interest via the isopentenyl pyrophosphate pathway enzymes and isoprene synthase (E.C. 4.2.3.27) which converts to dimethylallyl diphosphate to isoprene. Exemplary enzymes include *Populus nigra* IspS (CAL69918) and homologs thereof. SEQ ID NO:3 represents the *Paracoccus* codon optimized coding sequence for the *P. nigra* ispS gene of the present invention. In one aspect, the invention provides nucleic acid molecules and homologs, variants and derivatives of SEQ ID NO:3. The nucleic acid sequences can have 70%, 71%, 72%, 73%, 74%, 75%, 76%, 77%, 78%, 79%, 80%, 81-85%, 90-95%, 96-98%, 99%, 99.9% or even higher identity to SEQ ID NO:3. The present invention provides nucleic acids each comprising or consisting of a sequence which is a codon optimized version of one of the wild-type ispS gene. In another embodiment, the invention provides nucleic acids each encoding a polypeptide having the amino acid sequence of CAL69918, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

In another embodiment, the engineered and/or evolved methylotroph of the present invention produces bisabolene as the carbon-based product of interest via the isopentenyl pyrophosphate pathway enzymes and E-alpha-bisabolene synthase (E.C. 4.2.3.38) which converts to farnesyl diphosphate to bisabolene. Exemplary enzymes include *Picea abies* TPS-bis (AAS47689) and homologs thereof. SEQ ID NO:4 represents the *Paracoccus* codon optimized coding sequence for the *P. abies* tps-bis gene of the present invention. In one aspect, the invention provides nucleic acid molecules and homologs, variants and derivatives of SEQ ID NO:4. The nucleic acid sequences can have 70%, 71%, 72%, 73%, 74%, 75%, 76%, 77%, 78%, 79%, 80%, 81-85%, 90-95%, 96-98%, 99%, 99.9% or even higher identity to SEQ ID NO:4. The present invention provides nucleic acids each comprising or consisting of a sequence which is a codon optimized version of one of the wild-type tps-bis gene. In another embodiment, the invention provides nucleic acids each encoding a polypeptide having the amino acid sequence of AAS47689, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

In another embodiment, the engineered and/or evolved methylotroph of the present invention produces rubber as the carbon-based product of interest via the isopentenyl pyrophosphate pathway enzymes and cis-polyprenylcistransferase (E.C. 2.5.1.20) which converts isopentenyl pyrophosphate to rubber. The enzyme cis-polyprenylcistransferase may come from, for example, *Hevea Brasiliensis*.

In another embodiment, the engineered and/or evolved methylotroph of the present invention produce isopentanol as the carbon-based product of interest via the isopentenyl pyrophosphate pathway enzymes and isopentanol dikinase.

In another embodiment, the engineered and/or evolved methylotroph produces squalene as the carbon-based product of interest via the isopentenyl pyrophosphate pathway enzymes, geranyl diphosphate synthase (E.C. 2.5.1.1), farnesyl diphosphate synthase (E.C. 2.5.1.10) and squalene synthase (E.C. 2.5.1.21). Geranyl diphosphate synthase converts dimethylallyl pyrophosphate and isopentenyl pyrophosphate to geranyl diphosphate. Farnesyl diphosphate synthase converts geranyl diphosphate and isopentenyl diphosphate to farnesyl diphosphate. A bifunctional enzyme carries out the conversion of dimethylallyl pyrophosphate and two isopentenyl pyrophosphate to farnesyl pyrophosphate. Exemplary enzymes include *Escherichia coli* IspA (NP_414955) and homologs thereof. Squalene synthase converts two farnesyl pyrophosphate and NADPH to squalene. In another embodiment, the engineered and/or evolved methylotroph produces lanosterol as the carbon-based product of interest via the above enzymes, squalene monooxygenase (E.C. 1.14.99.7) and lanosterol synthase (E.C. 5.4.99.7). Squalene monooxygenase converts squalene, NADPH and $O_2$ to (S)-squalene-2,3-epoxide. Exemplary enzymes include *Saccharomyces cerevisiae* Erg1 (NP_011691) and homologs thereof. Lanosterol synthase converts (S)-squalene-2,3-epoxide to lanosterol. Exemplary enzymes include *Saccharomyces cerevisiae* Erg7 (NP_011939) and homologs thereof.

In another embodiment, the engineered and/or evolved methylotroph of the present invention produces lycopene as the carbon-based product of interest via the isopentenyl pyrophosphate pathway enzymes, geranyl diphosphate synthase (E.C. 2.5.1.21, described above), farnesyl diphosphate synthase (E.C. 2.5.1.10, described above), geranylgeranyl pyrophosphate synthase (E.C. 2.5.1.29), phytoene synthase (E.C. 2.5.1.32), phytoene oxidoreductase (E.C. 1.14.99.n) and ζ-carotene oxidoreductase (E.C. 1.14.99.30). Geranylgeranyl pyrophosphate synthase converts isopentenyl pyrophosphate and farnesyl pyrophosphate to (all trans)-geranylgeranyl pyrophosphate. Exemplary geranylgeranyl pyrophosphate synthases include *Synechocystis* sp. PCC6803 crtE (NP_440010) and homologs thereof. Phytoene synthase converts 2 geranylgeranyl-PP to phytoene. Exemplary enzymes include *Synechocystis* sp. PCC6803 crtB (P37294). Phytoene oxidoreductase converts phytoene, 2 NADPH and 2 $O_2$ to ζ-carotene. Exemplary enzymes include *Synechocystis* sp. PCC6803 crtI and *Synechocystis* sp. PCC6714 crtI (P21134). ζ-carotene oxidoreductase converts ζ-carotene, 2 NADPH and 2 $O_2$ to lycopene. Exemplary enzymes include *Synechocystis* sp. PCC6803 crtQ-2 (NP_441720).

In another embodiment, the engineered and/or evolved methylotroph of the present invention produces limonene as the carbon-based product of interest via the isopentenyl pyrophosphate pathway enzymes, geranyl diphosphate synthase (E.C. 2.5.1.21, described above) and one of (R)-limonene synthase (E.C. 4.2.3.20) and (4S)-limonene synthase (E.C. 4.2.3.16) which convert geranyl diphosphate to a limonene enantiomer. Exemplary (R)-limonene synthases include that from *Citrus limon* (AAM53946) and homologs thereof. Exemplary (4S)-limonene synthases include that from *Mentha spicata* (AAC37366) and homologs thereof.

Figure 13:
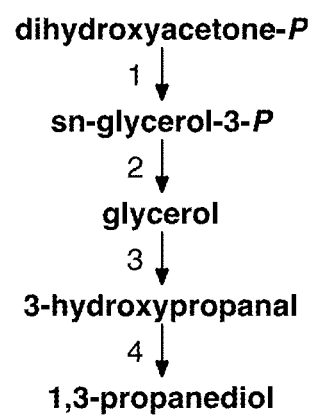
FIG. 13 depicts the metabolic reactions of the glycerol/1,3-propanediol biosynthetic pathway for production of glycerol or 1,3-propanediol. In metabolite names, —P denotes phosphate. Each reaction is numbered. Enzymes catalyzing each reaction are as follows: 1, sn-glycerol-3-P dehydrogenase (E.C. 1.1.1.8 or 1.1.1.94); 2, sn-glycerol-3-phosphatase (E.C. 3.1.3.21); 3, sn-glycerol-3-P glycerol dehydratase (E.C. 4.2.1.30); 4, 1,3-propanediol oxidoreductase (E.C. 1.1.1.202).

Production of Glycerol or 1,3-Propanediol as the Carbon-Based Products of Interest In one aspect, the engineered and/or evolved methylotroph of the present invention produces glycerol or 1,3-propanediol as the carbon-based products of interest (FIG. 13). The reactions in the glycerol pathway are catalyzed by the following enzymes: sn-glycerol-3-P dehydrogenase (E.C. 1.1.1.8 or E.C. 1.1.1.94) and sn-glycerol-3-phosphatase (E.C. 3.1.3.21). To produce 1,3,-propanediol, the following enzymes are also included: sn-glycerol-3-P. glycerol dehydratase (E.C. 4.2.1.30) and 1,3-propanediol oxidoreductase (E.C. 1.1.1.202). Exemplary sn-glycerol-3-P dehydrogenases include *Saccharomyces cerevisiae* dar1 and homologs thereof. Exemplary sn-glycerol-3-phosphatases include *Saccharomyces cerevisiae* gpp2 and homologs thereof. Exemplary sn-glycerol-3-P. glycerol dehydratases include *K. pneumoniae* dhaB1-3. Exemplary 1,3-propanediol oxidoreductase include *K. pneumoniae* dhaT.

Production of 1,4-Butanediol or 1,3-Butadiene as the Carbon-Based Products of Interest In one aspect, the engineered and/or evolved methylotroph of the present invention produces 1,4-butanediol or 1,3-butanediene as the carbon-based products of interest. The metabolic reactions in the 1,4-butanediol or 1,3-butadiene pathway are catalyzed by the following enzymes: succinyl-CoA dehydrogenase (E.C. 1.2.1.n; e.g., *C. kluyveri* SucD), 4-hydroxybutyrate dehydrogenase (E.C. 1.1.1.2; e.g., *Arabidopsis thaliana* GHBDH), aldehyde dehydrogenase (E.C. 1.1.1.n; e.g., *E. coli* AldH), 1,3-propanediol oxidoreductase (E.C. 1.1.1.202; e.g., *K. pneumoniae* DhaT), and optionally alcohol dehydratase (E.C. 4.2.1.-). Succinyl-CoA dehydrogenase converts succinyl-CoA and NADPH to succinic semialdehyde and CoA. 4-hydroxybutyrate dehydrogenase converts succinic semialdehyde and NADPH to 4-hydroxybutyrate. Aldehyde dehydrogenase converts 4-hydroxybutyrate and NADH to 4-hydroxybutanal. 1,3-propanediol oxidoreductase converts 4-hydroxybutanal and NADH to 1,4-butanediol. Alcohol dehydratase converts 1,4-butanediol to 1,3-butadiene.

Production of Polyhydroxybutyrate as the Carbon-Based Products of Interest

Figure 14:
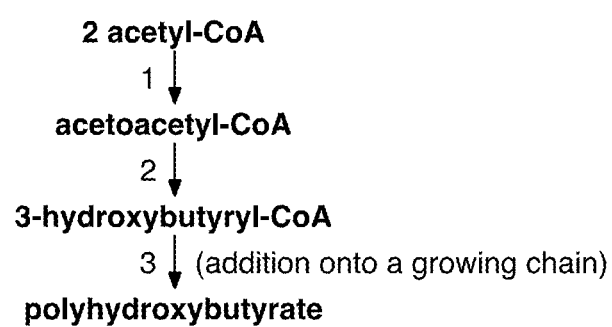
FIG. 14 depicts the metabolic reactions of the polyhydroxybutyrate biosynthetic pathway. Each reaction is numbered. Enzymes catalyzing each reaction are as follows: 1, acetyl-CoA:acetyl-CoA C-acetyltransferase (E.C. 2.3.1.9); 2, (R)-3-hydroxyacyl-CoA:NADP+ oxidoreductase (E.C. 1.1.1.36); 3, polyhydroxyalkanoate synthase (E.C. 2.3.1.-).

In one aspect, the engineered and/or evolved methylotroph of the present invention produces polyhydroxybutyrate as the carbon-based products of interest (FIG. 14). The reactions in the polyhydroxybutyrate pathway are catalyzed by the following enzymes: acetyl-CoA:acetyl-CoA C-acetyltransferase (E.C. 2.3.1.9), (R)-3-hydroxyacyl-CoA:NADP+ oxidoreductase (E.C. 1.1.1.36) and polyhydroxyalkanoate synthase (E.C. 2.3.1.-). Exemplary acetyl-CoA:acetyl-CoA C-acetyltransferases include *Ralstonia eutropha* phaA. Exemplary (R)-3-hydroxyacyl-CoA:NADP+ oxidoreductases include *Ralstonia eutropha* phaB. Exemplary polyhydroxyalkanoate synthase include *Ralstonia eutropha* phaC. In the event that the host organism also has the capacity to degrade polyhydroxybutyrate, the corresponding degradation enzymes, such as poly[(R)-3-hydroxybutanoate]hydrolase (E.C. 3.1.1.75), may be inactivated. Hosts that lack the ability to naturally synthesize polyhydroxybutyrate generally also lack the capacity to degrade it, thus leading to irreversible accumuation of polyhydroxybutyrate if the biosynthetic pathway is introduced. Some methylotrophic bacteria can naturally make poly(3-hydroxybutyrate) or poly(3-hydroxybutyrate-co-3-hydroxyvalerate), such as *Paracoccus denitrificans* [Appl Environ Microbiol, 1996, 62(2):380-384].

Intracellular polyhydroxybutyrate can be measured by solvent extraction and esterification of the polymer from whole cells. Typically, lyophilized biomass is extracted with methanol-chloroform with 10% HCl as a catalyst. The chloroform dissolves the polymer, and the methanol esterifies it in the presence of HCl. The resulting mixture is extracted with water to remove hydrophilic substances and the organic phase is analyzed by GC.

Production of Lysine as the Carbon-Based Products of Interest

Figure 15:
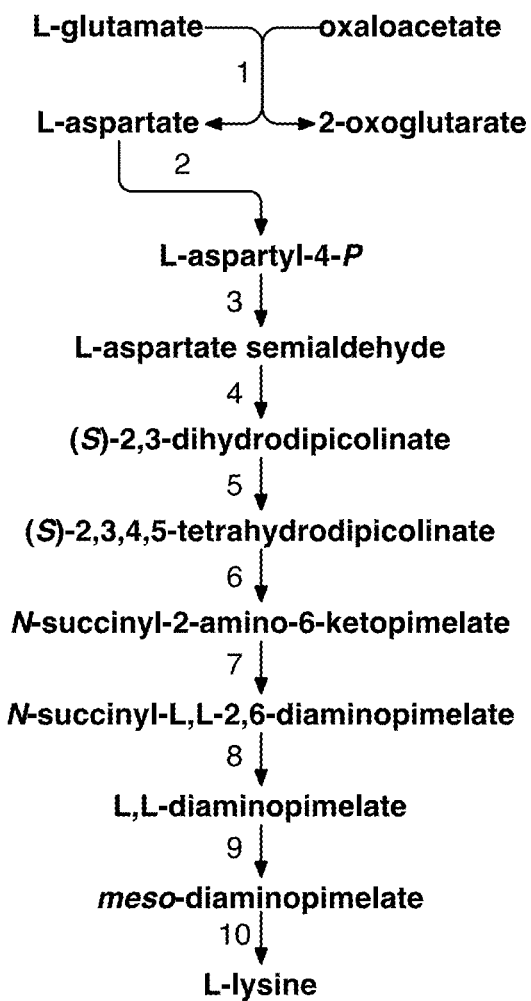
FIG. 15 depicts the metabolic reactions of one lysine biosynthesis pathway. In metabolite names, —P denotes phosphate. Each reaction is numbered. Enzymes catalyzing each reaction are as follows: 1, aspartate aminotransferase (E.C. 2.6.1.1); 2, aspartate kinase (E.C. 2.7.2.4); 3, aspartate semialdehyde dehydrogenase (E.C. 1.2.1.11); 4, dihydrodipicolinate synthase (E.C. 4.2.1.52); 5, dihydrodipicolinate reductase (E.C. 1.3.1.26); 6, tetrahydrodipicolinate succinylase (E.C. 2.3.1.117); 7, N-succinyldiaminopimelate-aminotransferase (E.C. 2.6.1.17); 8, N-succinyl-L-diaminopimelate desuccinylase (E.C. 3.5.1.18); 9, diaminopimelate epimerase (E.C. 5.1.1.7); 10, diaminopimelate decarboxylase (E.C. 4.1.1.20).

In one aspect, the engineered and/or evolved methylotroph of the present invention produces lysine as the carbon-based product of interest. There are several known lysine biosynthetic pathways. One lysine biosynthesis pathway is depicted in FIG. 15. The reactions in one lysine biosynthetic pathway are catalyzed by the following enzymes: aspartate aminotransferase (E.C. 2.6.1.1; e.g. *E. coli* AspC), aspartate kinase (E.C. 2.7.2.4; e.g., *E. coli* LysC), aspartate semialdehyde dehydrogenase (E.C. 1.2.1.11; e.g., *E. coli* Asd), dihydrodipicolinate synthase (E.C. 4.2.1.52; e.g., *E. coli* DapA), dihydrodipicolinate reductase (E.C. 1.3.1.26; e.g., *E. coli* DapB), tetrahydrodipicolinate succinylase (E.C. 2.3.1.117; e.g., *E. coli* DapD), N-succinyldiaminopimelate-aminotransferase (E.C. 2.6.1.17; e.g., *E. coli* ArgD), N-succinyl-L-diaminopimelate desuccinylase (E.C. 3.5.1.18; e.g., *E. coli* DapE), diaminopimelate epimerase (E.C. 5.1.1.7; *E. coli* DapF), diaminopimelate decarboxylase (E.C. 4.1.1.20; e.g., *E. coli* LysA). In one embodiment, the engineered and/or evolved methylotroph of the present invention expresses one or more enzymes from a lysine biosynthetic pathway. For example, one or more exogenous proteins can be selected from aspartate aminotransferase, aspartate kinase, aspartate semialdehyde dehydrogenase, dihydrodipicolinate synthase, dihydrodipicolinate reductase, tetrahydrodipicolinate succinylase, N-succinyldiaminopimelate-aminotransferase, N-succinyl-L-diaminopimelate desuccinylase, diaminopimelate epimerase, diaminopimelate decarboxylase, L,L-diaminopimelate aminotransferase (E.C. 2.6.1.83; e.g., *Arabidopsis thaliana* At4g33680), homocitrate synthase (E.C. 2.3.3.14; e.g., *Saccharomyces cerevisiae* LYS21), homoaconitase (E.C. 4.2.1.36; e.g., *Saccharomyces cerevisiae* LYS4, LYS3), homoisocitrate dehydrogenase (E.C. 1.1.1.87; e.g., *Saccharomyces cerevisiae* LYS12, LYS11, LYS10), 2-aminoadipate transaminase (E.C. 2.6.1.39; e.g., *Saccharomyces cerevisiae* ARO8), 2-aminoadipate reductase (E.C. 1.2.1.31; e.g., *Saccharomyces cerevisiae* LYS2, LYS5), aminoadipate semialdehyde-glutamate reductase (E.C. 1.5.1.10; e.g., *Saccharomyces cerevisiae* LYS9, LYS13), lysine-2-oxoglutarate reductase (E.C. 1.5.1.7; e.g., *Saccharomyces cerevisiae* LYS1). The host organism can also express two or more, three or more, four or more, and the like, including up to all the protein and enzymes that confer lysine biosynthesis.

Production of Aromatic Compounds as the Carbon-Based Products of Interest

In certain embodiments, the engineered and/or evolved methylotroph of the present invention produces aromatic amino acids, their intermediates or their derivatives, including but not limited to shikimate, chorismate, prephenate, phenylalanine, tyrosine, tryptophan, or phenylpropranoids, as the carbon-based products of interest. The engineered and/or evolved methylotroph produces aromatic compounds as an intermediate or product of the methylotrophic or carbon fixation pathway or as a intermediate or product of host metabolism. In such cases, one or more transporters may be expressed in the engineered and/or evolved methylotroph to export the aromatic compound from the cell. These aromatic metabolites can be converted to other products.

In certain embodiments, the engineered and/or evolved methylotroph of the present invention produces chorismate as the carbon-based product of interested or as a central metabolite precursor to an aromatic carbon-based product of interest. There are multiple pathways for chorismate biosynthesis. The reactions in one chorismate biosynthesis pathway are catalyzed by the following enzymes: 2-dehydro-3-deoxyphosphoheptonate aldolase (E.C. 2.5.1.54, e.g., *E. coli* AroG, AroH, AroF), 3-dehydroquinate synthase (E.C. 4.2.3.4, e.g., *E. coli* AroB), 3-dehydroquinate dehydratase (E.C. 4.2.1.10, e.g., *E. coli* AroD), NADPH-dependent shikimate dehydrogenase (E.C. 1.1.1.25, e.g., *E. coli* AroE), NAD(P)H-dependent shikimate dehydrogenase (E.C. 1.1.1.282, e.g., *E. coli* YdiB), shikimate kinase (E.C. 2.7.1.71, e.g., *E. coli* AroL or AroK), 3-phosphoshikimate-1-carboxyvinyltransferase (E.C. 2.5.1.19, e.g., *E. coli* AroA) and chorismate synthase (E.C. 4.2.3.5, e.g., *E. coli* AroC). In one embodiment, the engineered and/or evolved methylotroph of the present invention expresses one or more enzymes from a chorismate biosynthetic pathway. For example, one or more exogenous proteins can be selected from 2-dehydro-3-deoxyphosphoheptonate aldolase, 3-dehydroquinate synthase, 3-dehydroquinate dehydratase, NADPH-dependent shikimate dehydrogenase, NAD(P)H-dependent shikimate dehydrogenase, shikimate kinase, 3-phosphoshikimate-1-carboxyvinyltransferase and chorismate synthase. The host organism can also express two or more, three or more, four or more, and the like, including up to all the protein and enzymes that confer chorismate biosynthesis. Chorismate serves as an intermediate to several aromatic compounds including phenylalanine, tyrosine, tryptophan and the phenylpropranoids.

In certain embodiments, the engineered and/or evolved methylotroph of the present invention produces phenylalanine as the carbon-based product of interested or as a precursor to an aromatic carbon-based product of interest. There are multiple pathways for phenylalanine biosynthesis. The reactions in one phenylalanine biosynthesis pathway are catalyzed by the following enzymes: chorismate mutase (E.C. 5.4.99.5, e.g., *E. coli* PheA or TyrA), prephenate dehydratase (E.C. 4.2.1.51, e.g., *E. coli* PheA), phenylalanine transaminase (E.C. 2.6.1.57, e.g., *E. coli* IlvE). In one embodiment, the engineered and/or evolved methylotroph of the present invention expresses one or more enzymes from a phenylalanine biosynthetic pathway. For example, one or more exogenous proteins can be selected from chorismate mutase, prephenate dehydratase and phenylalanine transaminase. The host organism can also express two or more, three or more, and the like, including up to all the protein and enzymes that confer phenylalanine biosynthesis. Mutants of the methylotrophic *Paracoccus denitrificans* have been isolated with high aminotransferase (transaminase) activity [Appl Microbiol Biotechnol, 1989, 30(3):243-246, DOI: 10.1007/BF00256212].

In certain embodiments, the engineered and/or evolved methylotroph of the present invention produces tyrosine as the carbon-based product of interested or as a precursor to an aromatic carbon-based product of interest. There are multiple pathways for tyrosine biosynthesis. The reactions in one tyrosine biosynthesis pathway are catalyzed by the following enzymes: chorismate mutase (E.C. 5.4.99.5, e.g., *E. coli* PheA or TyrA), prephenate dehydrogenase (E.C. 1.3.1.12, e.g., *E. coli* TyrA), tyrosine aminotransferase (E.C. 2.6.1.57, e.g., *E. coli* AspC or TyrB). In one embodiment, the engineered and/or evolved methylotroph of the present invention expresses one or more enzymes from a tyrosine biosynthetic pathway. For example, one or more exogenous proteins can be selected from chorismate mutase, prephenate dehydrogeanse and tyrosine aminotransferase. The host organism can also express two or more, three or more, and the like, including up to all the protein and enzymes that confer tyrosine biosynthesis.

Production of γ-Valerolactone as the Carbon-Based Product of Interest

Figure 16:
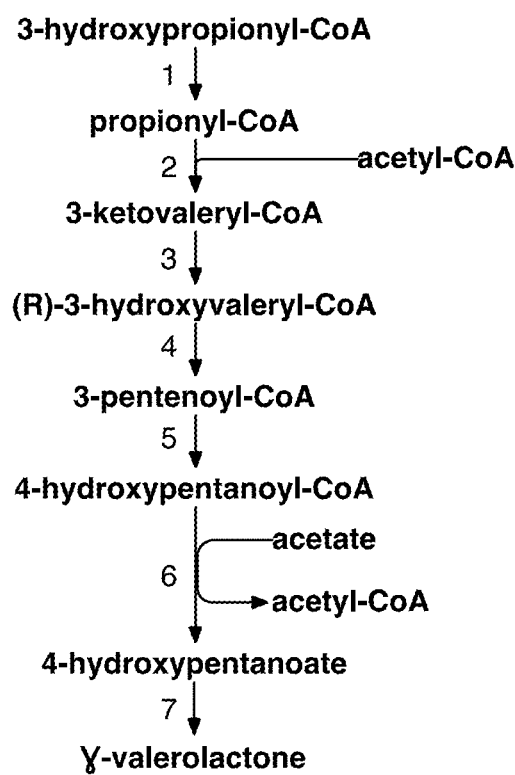
FIG. 16 depicts the metabolic reactions of the γ-valerolactone biosynthetic pathway. Each reaction is numbered. Enzymes catalyzing each reaction are as follows: 1, propionyl-CoA synthase (E.C. 6.2.1.-, E.C. 4.2.1.- and E.C. 1.3.1.-); 2, beta-ketothiolase (E.C. 2.3.1.16); 3, acetoacetyl-CoA reductase (E.C. 1.1.1.36); 4, 3-hydroxybutyryl-CoA dehydratase (E.C. 4.2.1.55); 5, vinylacetyl-CoA Δ-isomerase (E.C. 5.3.3.3); 6, 4-hydroxybutyryl-CoA transferase (E.C. 2.8.3.-); 7, 1,4-lactonase (E.C. 3.1.1.25).

In some embodiments, the engineered and/or evolved methylotroph of the present invention is engineered to produce γ-valerolactone as the carbon-based product of interest. One example γ-valerolactone biosynthetic pathway is shown in FIG. 16. In one embodiment, the engineered and/or evolved methylotroph is engineered to express one or more of the following enzymes: propionyl-CoA synthase (E.C. 6.2.1.-, E.C. 4.2.1.- and E.C. 1.3.1.-), beta-ketothiolase (E.C. 2.3.1.16; e.g., *Ralstonia eutropha* BktB), acetoacetyl-CoA reductase (E.C. 1.1.1.36; e.g., *Ralstonia eutropha* PhaB), 3-hydroxybutyryl-CoA dehydratase (E.C. 4.2.1.55; e.g., *X. axonopodis* Crt), vinylacetyl-CoA Δ-isomerase (E.C. 5.3.3.3; e.g., *C. difficile* AbfD), 4-hydroxybutyryl-CoA transferase (E.C. 2.8.3.-; e.g., *C. kluyveri* OrfZ), 1,4-lactonase (E.C. 3.1.1.25; e.g., that from *R. norvegicus*). Propionyl-CoA synthase is a multi-functional enzyme that converts 3-hydroxypropionate, ATP and NADPH to propionyl-CoA. Exemplary propionyl-CoA synthases include AAL47820, and homologs thereof. In another embodiment, the invention provides a nucleic acid encoding a polypeptide having the amino acid sequence of SEQ ID NO:5, or a sequence having 70%, 71%, 72%, 73%, 74%, 75%, 76%, 77%, 78%, 79%, 80%, 81-85%, 90-95%, 96-98%, 99%, 99.9% or even higher identity thereto.

Integration of Metabolic Pathways into Host Metabolism

The engineered and/or evolved methylotrophs of the invention can be produced by introducing expressible nucleic acids encoding one or more of the enzymes or proteins participating in one or more carbon product biosynthetic pathways. Depending on the host methylotroph chosen, nucleic acids for some or all of particular metabolic pathways can be expressed. For example, if a chosen host methylotroph is deficient in one or more enzymes or proteins for desired metabolic pathways, then expressible nucleic acids for the deficient enzyme(s) or protein(s) are introduced into the host for subsequent exogenous expression. Alternatively, if the chosen host methylotroph exhibits endogenous expression of some pathway genes, but is deficient in others, then an encoding nucleic acid is needed for the deficient enzyme(s) or protein(s) to achieve production of desired carbon products from C1 compounds. Thus, an engineered and/or evolved methylotroph of the invention can be produced by introducing exogenous enzyme or protein activities to obtain desired metabolic pathways or desired metabolic pathways can be obtained by introducing one or more exogenous enzyme or protein activities that, together with one or more endogenous enzymes or proteins, produces a desired product such as reduced cofactors, central metabolites and/or carbon-based products of interest.

Depending on the metabolic pathway constituents of a selected host methylotroph, the engineered and/or evolved methylotrophs of the invention can include at least one exogenously expressed metabolic pathway-encoding nucleic acid and up to all encoding nucleic acids for one or more energy conversion, carbon fixation, methylotrophic and/or carbon-based product pathways. For example, a RuMP-derived carbon fixation pathway can be established in a host deficient in a pathway enzyme or protein through exogenous expression of the corresponding encoding nucleic acid. In a host deficient in all enzymes or proteins of a metabolic pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a carbon fixation pathway derived from the 3-HPA bicycle can be included, such as the acetyl-CoA carboxylase, malonyl-CoA reductase, propionyl-CoA synthase, propionyl-CoA carboxylase, methylmalonyl-CoA epimerase, methylmalonyl-CoA mutase, succinyl-CoA:(S)-malate CoA transferase, succinate dehydrogenase, fumarate hydratase, (S)-malyl-CoA/β-methylmalyl-CoA/(S)-citramalyl-CoA lyase, mesaconyl-C1-CoA hydratase, mesaconyl-CoA C1-C4 CoA transferase, and mesaconyl-C4-CoA hydratase. Given the teachings and guidance provided herein, those skilled in the art would understand that the number of encoding nucleic acids to introduce in an expressible form can, at least, parallel the metabolic pathway deficiencies of the selected methylotroph.

Genetic Engineering Methods for Optimization of Metabolic Pathways

In some embodiments, the engineered and/or evolved methylotrophs of the invention also can include other genetic modifications that facilitate or optimize production of a carbon-based product from C1 compounds or that confer other useful functions onto the host organism.

In one aspect, the expression levels of the proteins of interest of the energy conversion pathways, carbon fixation pathways, methylotrophic pathways and/or carbon product biosynthetic pathways can be either increased or decreased by, for example, replacing or altering the expression control sequences with alternate expression control sequences encoded by standardized genetic parts. The exogenous standardized genetic parts can regulate the expression of either heterologous or endogenous genes of the metabolic pathway. Altered expression of the enzyme or enzymes and/or protein or proteins of a metabolic pathway can occur, for example, through changing gene position or gene order

[Smolke, 2002b], altered gene copy number [Smolke, 2002a], replacement of a endogenous, naturally occurring regulated promoters with constitutive or inducible synthetic promoters, mutation of the ribosome binding sites [Wang, 2009], or introduction of RNA secondary structural elements and/or cleavage sites [Smolke, 2000; Smolke, 2001].

In another aspect, some engineered and/or evolved methylotrophs of the present invention may require specific transporters to facilitate uptake of C1 compounds. In some embodiments, the engineered and/or evolved methylotrophs use formate as a C1 compound. If formate uptake is limiting for either growth or production of carbon-based products of interest, then expression of one or more formate transporters in the engineered and/or evolved methylotroph of the present invention can alleviate this bottleneck. The formate transporters may be heterologous or endogenous to the host organism. Exemplary formate transporters include NP_415424 and NP_416987, and homologs thereof. The present invention provides nucleic acids each comprising or consisting of a sequence which is a codon optimized version of one of the wild-type formate transporter genes. In another embodiment, the invention provides nucleic acids each encoding a polypeptide having the amino acid sequence of one of NP_415424 and NP_416987.

In addition, the invention provides an engineered and/or evolved methylotroph comprising a genetic modification conferring to the engineered and/or evolved methylotrophic microorganism an increased efficiency of using C1 compounds to produce carbon-based products of interest relative to the microorganism in the absence of the genetic modification. The genetic modification comprises one or more gene disruptions, whereby the one or more gene disruptions increase the efficiency of producing carbon-based products of interest from C1 compounds. In one aspect, the one or more gene disruptions target genes encoding competing reactions for C1 compounds, reduced cofactors, and/or central metabolites. In another aspect, the one or more gene disruptions target genes encoding competing reactions for intermediates or products of the energy conversion, methylotrophic, carbon fixation, and/or carbon product biosynthetic pathways of interest. The competing reactions usually, but not exclusively, arise from metabolism endogenous to the host cell or organism. Methods for introducing unmarked mutations into the genome of methylotrophic bacteria such as *Paracoccus denitrificans* have been shown previously [J Bacteriol, 1991, 173(21):6962-6970].

A combination of different approaches may be used to identify candidate genetic modifications. Such approaches include, for example, metabolomics (which may be used to identify undesirable products and metabolic intermediates that accumulate inside the cell), metabolic modeling and isotopic labeling (for determining the flux through metabolic reactions contributing to hydrocarbon production), and conventional genetic techniques (for eliminating or substantially disabling unwanted metabolic reactions). For example, metabolic modeling provides a means to quantify fluxes through the cell's metabolic pathways and determine the effect of elimination of key metabolic steps. In addition, metabolomics and metabolic modeling enable better understanding of the effect of eliminating key metabolic steps on production of desired products.

To predict how a particular manipulation of metabolism affects cellular metabolism and synthesis of the desired product, a theoretical framework was developed to describe the molar fluxes through all of the known metabolic pathways of the cell. Several important aspects of this theoretical framework include: (i) a relatively complete database of known pathways, (ii) incorporation of the growth-rate dependence of cell composition and energy requirements, (iii) experimental measurements of the amino acid composition of proteins and the fatty acid composition of membranes at different growth rates and dilution rates and (iv) experimental measurements of side reactions which are known to occur as a result of metabolism manipulation. These new developments allow significantly more accurate prediction of fluxes in key metabolic pathways and regulation of enzyme activity [Keasling, 1999a; Keasling, 1999b; Martin, 2002; Henry, 2006].

Such types of models have been applied, for example, to analyze metabolic fluxes in organisms responsible for enhanced biological phosphorus removal in wastewater treatment reactors and in filamentous fungi producing polyketides [Pramanik, 1997; Pramanik, 1998a; Pramanik, 1998b; Pramanik, 1998c].

In another aspect, some engineered and/or evolved methylotrophs of the present invention may require alterations to the pool of intracellular reducing cofactors for efficient growth and/or production of the carbon-based product of interest from C1 compounds. In some embodiments, the total pool of $NAD^+/NADH$ in the engineered and/or evolved methylotroph is increased or decreased by adjusting the expression level of nicotinic acid phosphoribosyltransferase (E.C. 2.4.2.11). Over-expression of either the *E. coli* or *Salmonella* gene pncB which encodes nicotinic acid phosphoribosyltransferase has been shown to increase total $NAD^+/NADH$ levels in *E. coli* [Wubbolts, 1990; Berrios-River, 2002; San, 2002]. In another embodiment, the availability of intracellular NADPH can be also altered by modifying the engineered and/or evolved methylotroph to express an NADH:NADPH transhydrogenase [Sauer, 2004; Chin, 2011]. In another embodiment, the total pool of ubiquinone in the engineered and/or evolved methylotroph is increased or decreased by adjusting the expression level of ubiquinone biosynthetic enzymes, such as p-hydroxybenzoate-polyprenyl pyrophosphate transferase and polyprenyl pyrophosphate synthetase. Overexpression of the corresponding *E. coli* genes ubiA and ispB increased the ubiquinone pool in *E. coli* [Zhu, 1995]. In the methylotroph *Paracoccus denitrificans*, p-hydroxybenzoate and mevalonate have been shown to be limiting in production of ubiquinone-10 under anaerobic conditions [Appl Microbiol Biotechnol, 1983, 17(2):85-89, DOI: 10.1007/BF00499856]. In another embodiment, the level of the redox cofactor ferredoxin in the engineered and/or evolved methylotroph can be increased or decreased by changing the expression control sequences that regulate its expression.

In another aspect, in addition to a C1 compound, some engineered and/or evolved methylotrophs may require a specific nutrients or vitamin(s) for growth and/or production of carbon-based products of interest. For example, hydroxocobalamin, a vitamer of vitamin B12, is a cofactor for particular enzymes of the present invention, such as methylmalonyl-CoA mutase (E.C. 5.4.99.2). Required nutrients are generally supplemented to the growth media during bench scale propagation of such organisms. However, such nutrients can be prohibitively expensive in the context of industrial scale bio-processing. In one embodiment of the present invention, the host cell is selected from a methylotroph that naturally produces the required nutrient(s), such as *Protaminobacter ruber* or *Methylobacterium extorquens*, which naturally produces hydroxocobalamin. In an alternate embodiment, the need for a vitamin is obviated by modifying the engineered and/or evolved methylotroph to express a vitamin biosynthesis pathway [Roessner, 1995]. An exemplary biosynthesis pathway for hydroxocobalamin comprises the following enzymes: uroporphyrin-III C-methyltransferase (E.C. 2.1.1.107), precorrin-2 cobaltochelatase (E.C. 4.99.1.3), cobalt-precorrin-2 ($C^{20}$)-methyltransferase (E.C. 2.1.1.151), cobalt-precorrin-3 ($C^{17}$)-methyltransferase (E.C. 2.1.1.131), cobalt precorrin-4 ($C^{11}$)-methyltransferase (E.C. 2.1.1.133), cobalt-precorrin 5A hydrolase (E.C. 3.7.1.12), cobalt-precorrin-5B ($C^1$)-methyltransferase (E.C. 2.1.1.195), cobalt-precorrin-6A reductase, cobalt-precorrin-6V ($C^5$)-methyltransferase (E.C. 2.1.1.-), cobalt-precorrin-7 ($C^{15}$)-methyltransferase (decarboxylating) (E.C. 2.1.1.196), cobalt-precorrin-8X methylmutase, cobyrinate A,C-diamide synthase (E.C. 6.3.5.11), cob(II)yrinate a,c-diamide reductase (E.C. 1.16.8.1), cob(I)yrinic acid a,c-diamide adenosyltransferase (E.C. 2.5.1.17), adenosyl-cobyrate synthase (E.C. 6.3.5.10), adenosylcobinamide phosphate synthase (E.C. 6.3.1.10), GTP:adenosylcobinamide-phosphate guanylyltransferase (E.C. 2.7.7.62), nicotinate-nucleotide dimethylbenzimidazole phosphoribosyltransferase (E.C. 2.4.2.21), adenosylcobinamide-GDP:α-ribazole-5-phosphate ribazoletransferase (E.C. 2.7.8.26) and adenosylcobalamine-5'-phosphate phosphatase (E.C. 3.1.3.73). In addition, to allow for cobalt uptake and incorporation into vitamin B12, the genes encoding the cobalt transporter are overexpressed. The exemplary cobalt transporter protein found in Salmonella enterica is overexpressed and is encoded by proteins ABC-type $Co^{2+}$ transport system, permease component (CbiM, NP_460968), ABC-type cobalt transport system, periplasmic component (CbiN, NP_460967), and ABC-type cobalt transport system, permease component (CbiQ, NP_461989).

In some embodiments, the intracellular concentration (e.g., the concentration of the intermediate in the engineered and/or evolved methylotroph) of the metabolic pathway intermediate can be increased to further boost the yield of the final product. For example, by increasing the intracellular amount of a substrate (e.g., a primary substrate) for an enzyme that is active in the metabolic pathway, and the like.

In another aspect, the carbon-based products of interest are or are derived from the intermediates or products of fatty acid biosynthesis. To increase the production of waxes/fatty acid esters, and fatty alcohols, one or more of the enzymes of fatty acid biosynthesis can be over expressed or mutated to reduce feedback inhibition. Additionally, enzymes that metabolize the intermediates to make nonfatty-acid based products (side reactions) can be functionally deleted or attenuated to increase the flux of carbon through the fatty acid biosynthetic pathway thereby enhancing the production of carbon-based products of interest.

Growth-Based Selection Methods for Optimization of Engineered Carbon-Fixing Strains Selective pressure provides a valuable means for testing and optimizing the engineered methylotrophs of the present invention. Alternatively, an evolved methylotroph having selected functionality after such selection can be further engineered to include additional or altered functionality. In some embodiments, the engineered methylotrophs of the invention can be evolved under selective pressure to optimize production of a carbon-based product from a C1 compound or that confer other useful functions onto the host organism. The ability of an optimized engineered methylotroph to replicate more rapidly than unmodified counterparts confirms the utility of the optimization. Similarly, the ability to survive and replicate in media lacking a required nutrient, such as vitamin B12, confirms the successful implementation of a nutrient biosynthetic module. In some embodiments, the engineered methylotrophs can be cultured in the presence of a limiting amount of C1 compound in order to select for evolved strains that more efficiently utilize the C1 compound. In some embodiments, the engineered methylotrophs of the invention can be evolved to grow despite the presence of inhibitory compounds in the C1 feedstock (see, e.g., Example 5).

Evolution can occur as a result of either spontaneous, natural mutation or by addition of mutagenic agents or conditions to live cells. If desired, additional genetic variation can be introduced prior to or during selective pressure by treatment with mutagens, such as ultra-violet light, alkylators [e.g., ethyl methanesulfonate (EMS), methyl methane sulfonate (MMS), diethylsulfate (DES), and nitrosoguanidine (NTG, NG, MMG)], DNA intercalcators (e.g., ethidium bromide), nitrous acid, base analogs, bromouracil, transposonsm and the like. Alternatively, genetic variation may be introduced via untargeted genetic mutagenesis techniques such as transposon insertion. Transposable elements have been used previously to generate phenotypic diversity in methylotrophic Paracoccus strains [PLoS ONE, 2012, 7(2):e32277, DOI: 10.1371/journal.pone.0032277]. The engineered methylotrophs can be propagated either in serial batch culture or in a turbidostat as a controlled growth rate.

Alternately or in addition to selective pressure, pathway activity can be monitored following growth under permissive (i.e., non-selective) conditions by measuring specific product output via various metabolic labeling studies (including radioactivity), biochemical analyses (Michaelis-Menten), gas chromatography-mass spectrometry (GC/MS), mass spectrometry, matrix assisted laser desorption ionization time-of-flight mass spectrometry (MALDI-TOF), capillary electrophoresis (CE), and high pressure liquid chromatography (HPLC).

To generate engineered methylotrophs with improved yield of central metabolites and/or carbon-based products of interest, metabolic modeling can be utilized to guide strain optimization. Modeling analysis allows reliable predictions of the effects on cell growth of shifting the metabolism towards more efficient production of central metabolites or products derived from central metabolites. Modeling can also be used to design gene knockouts that additionally optimize utilization of the energy conversion, methylotrophic, carbon fixation and carbon product biosynthetic pathways. In some embodiments, modeling is used to select growth conditions that create selective pressure towards uptake and utilization of C1 compound(s). An in silico stoichiometric model of host organism metabolism and the metabolic pathway(s) of interest can be constructed (see, for example, a model of the E. coli metabolic network [Edwards, 2002]). The resulting model can be used to compute phenotypic phase planes for the engineered methylotrophs of the present invention. A phenotypic phase plane is a portrait of the accessible growth states of an engineered methylotroph as a function of imposed substrate uptake rates. A particular engineered methylotroph, at particular uptake rates for limiting nutrients, may not grow as well as the phenotypic phase plane predicts, but no strain should be able to grow better than indicated by the phenotypic phase plane. Under a variety of circumstances, it has been shown the modified E. coli strains evolve towards, and then along, the phenotypic phase plane, always in the direction of increasing growth rates [Fong, 2004]. Thus, a phenotypic phase plane can be viewed as a landscape of selective pressure. Strains in an environment where a given nutrient uptake is positively correlated with growth rate are predicted to evolve towards increased nutrient uptake. Conversely, strains in an environment where nutrient uptake are inversely correlated with growth rate are predicted to evolve away from nutrient uptake.

Fermentation Conditions

The engineered and/or evolved methylotrophs of the present invention are cultured in a medium comprising C1 compound(s) and any required nutrients. The culture conditions can include, for example, liquid culture procedures as well as fermentation and other large scale culture procedures. In one embodiment, the engineered and/or evolved methylotroph is grown in a minimal salts medium containing a C1 feedstock, such as formate, formic acid, formaldehyde, or methanol. The medium composition can be optimized for enhanced growth and production of carbon-based products of interest (see, e.g., Example 1). In one embodiment, the medium composition is 100 mM sodium bicarbonate, 6 mM sodium chloride, 6 mM sodium nitrate, 11 mM sodium thiosulfate, and 26 mM sodium formate in addition to standard MOPS minimal medium components.

The production and isolation of carbon-based products of interest can be enhanced by employing specific fermentation techniques. One method for maximizing production while reducing costs is increasing the percentage of the carbon that is converted to carbon-based products of interest. During normal cellular lifecycles carbon is used in cellular functions including producing lipids, saccharides, proteins, organic acids, and nucleic acids. Reducing the amount of carbon necessary for growth-related activities can increase the efficiency of carbon source conversion to output. This can be achieved by first growing engineered and/or evolved methylotrophs to a desired density, such as a density achieved at the peak of the log phase of growth. At such a point, replication checkpoint genes can be harnessed to stop the growth of cells. Specifically, quorum sensing mechanisms [Camilli, 2006; Venturi, 2006; Reading, 2006] can be used to activate genes such as p53, p21, or other checkpoint genes. Genes that can be activated to stop cell replication and growth in *E. coli* include umuDC genes, the overexpression of which stops the progression from stationary phase to exponential growth [Murli, 2000]. UmuC is a DNA polymerase that can carry out translesion synthesis over non-coding lesions—the mechanistic basis of most UV and chemical mutagenesis. The umuDC gene products are used for the process of translesion synthesis and also serve as a DNA damage checkpoint. UmuDC gene products include UmuC, UmuD, umuD', UmuD'$_2$C, UmuD'$_2$ and UmUD$_2$. Simultaneously, the carbon product biosynthetic pathway genes are activated, thus minimizing the need for replication and maintenance pathways to be used while the carbon-based product of interest is being made.

Alternatively, cell growth and product production can be achieved simultaneously. In this method, cells are grown in bioreactors with a continuous supply of inputs and continuous removal of product. Batch, fed-batch, and continuous fermentations are common and well known in the art and examples can be found in [Brock, 1989; Deshpande, 1992].

In one embodiment, the engineered and/or evolved methylotroph is engineered such that the final product is released from the cell. In embodiments where the final product is released from the cell, a continuous process can be employed. In this approach, a reactor with organisms producing desirable products can be assembled in multiple ways. In one embodiment, the reactor is operated in bulk continuously, with a portion of media removed and held in a less agitated environment such that an aqueous product can self-separate out with the product removed and the remainder returned to the fermentation chamber. In embodiments where the product does not separate into an aqueous phase, media is removed and appropriate separation techniques (e.g., chromatography, distillation, etc.) are employed.

In an alternate embodiment, the product is not secreted by the engineered and/or evolved methylotrophs. In this embodiment, a batch-fed fermentation approach is employed. In such cases, cells are grown under continued exposure to inputs (C1 compounds) as specified above until the reaction chamber is saturated with cells and product. A significant portion to the entirety of the culture is removed, the cells are lysed, and the products are isolated by appropriate separation techniques (e.g., chromatography, distillation, filtration, centrifugation, etc.).

In certain embodiments, the engineered and/or evolved methylotrophs of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. It is highly desirable to maintain anaerobic conditions in the fermenter to reduce the cost of the overall process.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the C1 feedstock uptake rate by monitoring carbon source depletion over time.

In another embodiment, the engineered and/or evolved methylotrophs can be cultured in the presence of an electron acceptor, for example, nitrate, in particular under substantially anaerobic conditions. It is understood that an appropriate amount of nitrate can be added to a culture to achieve a desired increase in biomass, for example, 1 mM to 100 mM nitrate, or lower or higher concentrations, as desired, so long as the amount added provides a sufficient amount of electron acceptor for the desired increase in biomass. Such amounts include, but are not limited to, 5 mM, 10 mM, 15 mM, 20 mM, 25 mM, 30 mM, 40 mM, 50 mM, as appropriate to achieve a desired increase in biomass. In one embodiment, the engineered and/or evolved methylotroph is a denitrifier that can use nitrate as a terminal electron acceptor and reduce nitrate to nitrogen gas. In some embodiments, the engineered and/or evolved methylotroph is derived from methylotrophic denitrifers, such as *Paracoccus denitrificans*. Other electron acceptors include fumarate, trimethylammonium oxide, ferricyanide, or dimethyl sulfoxide.

In some embodiments, the engineered and/or evolved methylotrophs of the present invention are initially grown in culture conditions with a limiting amount of multi-carbon compounds to facilitate growth. Then, once the supply of organic carbon is exhausted, the engineered and/or evolved methylotrophs transition from heterotrophic to methylotrophic growth relying on energy from a C1 compounds in order to produce carbon-based products of interest. The organic carbon can be, for example, a carbohydrate source. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art would understand that renewable feedstocks and biomass other than those exemplified above also can be used for culturing the engineered and/or evolved methylotrophs of the invention. In some embodiments, the engineered and/or evolved methylotrophs are optimized for a two stage fermentation by regulating the expression of the carbon product biosynthetic pathway.

In one aspect, the percentage of input carbon atoms converted to hydrocarbon products is an efficient and inexpensive process. Typical efficiencies in the literature are ~<5%. Engineered and/or evolved methylotrophs which produce hydrocarbon products can have greater than 1, 3, 5, 10, 15, 20, 25, and 30% efficiency. In one example engineered and/or evolved methylotrophs can exhibit an efficiency of about 10% to about 25%. In other examples, such microorganisms can exhibit an efficiency of about 25% to about 30%, and in other examples such engineered and/or evolved methylotrophs can exhibit >30% efficiency.

In some examples where the final product is released from the cell, a continuous process can be employed. In this approach, a reactor with engineered and/or evolved methylotrophs producing for example, fatty acid derivatives, can be assembled in multiple ways. In one example, a portion of the media is removed and allowed to separate. Fatty acid derivatives are separated from the aqueous layer, which can in turn, be returned to the fermentation chamber.

In another example, the fermentation chamber can enclose a fermentation that is undergoing a continuous reduction. In this instance, a stable reductive environment can be created. The electron balance would be maintained by the release of oxygen. Efforts to augment the NAD/H and NADP/H balance can also facilitate in stabilizing the electron balance.

Consolidated Methylotrophic Fermentation

The above aspect of the invention is an alternative to directly producing final carbon-based product of interest as a result of methylotrophic metabolism. In this approach, carbon-based products of interest would be produced by leveraging other organisms that are more amenable to making any one particular product while culturing the engineered and/or evolved methylotroph for its carbon source. Consequently, fermentation and production of carbon-based products of interest can occur separately from carbon source production in a bioreactor.

In one aspect, the methods of producing such carbon-based products of interest include two steps. The first-step includes using engineered and/or evolved methylotrophs to convert C1 compound(s) to central metabolites or sugars such as glucose. The second-step is to use the central metabolites or sugars as a carbon source for cells that produce carbon-based products of interest. In one embodiment, the two-stage approach comprises a bioreactor comprising engineered and/or evolved methylotrophs; a second reactor comprising cells capable of fermentation; wherein the engineered and/or evolved methylotrophs provides a carbon source such as glucose for cells capable of fermentation to produce a carbon-based product of interest. The second reactor may comprise more than one type of microorganism. The resulting carbon-based products of interest are subsequently separated and/or collected.

In some embodiments, the two steps are combined into a single-step process whereby the engineered and/or evolved methylotrophs convert C1 compound(s) and directly into central metabolites or sugars such as glucose and such organisms are capable of producing a variety of carbon-based products of interest.

The present invention also provides methods and compositions for sustained glucose production in engineered and/or evolved methylotrophs wherein these or other organisms that use the sugars are cultured using C1 compound(s) for use as a carbon source to produce carbon-based products of interest. In such embodiments, the host cells are capable of secreting the sugars, such as glucose from within the cell to the culture media in continuous or fed-batch in a bioreactor.

Certain changes in culture conditions of engineered and/or evolved methylotrophs for the production of sugars can be optimized for growth. For example, conditions are optimized for C1 compound(s) and their concentration(s), electron acceptor(s) and their concentrations, addition of supplements and nutrients. As would be apparent to those skilled in the art, the conditions sufficient to achieve optimum growth can vary depending upon location, climate, and other environmental factors, such as the temperature, oxygen concentration and humidity. Other adjustments may be required, for example, an organism's ability for carbon uptake.

Advantages of consolidated methylotrophic fermentation include a process where there is separation of chemical end products, e.g., glucose, spatial separation between end products (membranes) and time. Additionally, unlike traditional or cellulosic biomass to biofuels production, pretreatment, saccharification and crop plowing are obviated.

The consolidated methylotrophic fermentation process produces continuous products. In some embodiments, the process involves direct conversion of C1 compound(s) to product from engineered front-end organisms to produce various products without the need to lyse the organisms. For instance, the organisms can utilize 3PGAL to make a desired fermentation product, e.g., ethanol. Such end products can be readily secreted as opposed to intracellular products such as oil and cellulose. In yet other embodiments, organisms produce sugars, which are secreted into the media and such sugars are used during fermentation with the same or different organisms or a combination of both.

Processing and Separation of Carbon-Based Products of Interest

The carbon-based products produced by the engineered and/or evolved methylotrophs during fermentation can be separated from the fermentation media. Known techniques for separating fatty acid derivatives from aqueous media can be employed. One exemplary separation process provided herein is a two-phase (bi-phasic) separation process. This process involves fermenting the genetically-engineered production hosts under conditions sufficient to produce for example, a fatty acid, allowing the fatty acid to collect in an organic phase and separating the organic phase from the aqueous fermentation media. This method can be practiced in both a batch and continuous fermentation setting.

Bi-phasic separation uses the relative immisciblity of fatty acid to facilitate separation. A skilled artisan would appreciate that by choosing a fermentation media and the organic phase such that the fatty acid derivative being produced has a high log P value, even at very low concentrations the fatty acid can separate into the organic phase in the fermentation vessel.

When producing fatty acids by the methods described herein, such products can be relatively immiscible in the fermentation media, as well as in the cytoplasm. Therefore, the fatty acid can collect in an organic phase either intracellularly or extracellularly. The collection of the products in an organic phase can lessen the impact of the fatty acid derivative on cellular function and allows the production host to produce more product.

The fatty alcohols, fatty acid esters, waxes, and hydrocarbons produced as described herein allow for the production of homogeneous compounds with respect to other compounds wherein at least 50%, 60%, 70%, 80%, 90%, or 95% of the fatty alcohols, fatty acid esters, waxes and hydrocarbons produced have carbon chain lengths that vary by less than 4 carbons, or less than 2 carbons. These compounds can also be produced so that they have a relatively uniform degree of saturation with respect to other compounds, for example at least 50%, 60%, 70%, 80%, 90%, or 95% of the fatty alcohols, fatty acid esters, hydrocarbons and waxes are mono-, di-, or tri-unsaturated.

Detection and Analysis

Generally, the carbon-based products of interest produced using the engineered and/or evolved methylotrophs described herein can be analyzed by any of the standard analytical methods, e.g., gas chromatography (GC), mass spectrometry (MS) gas chromatography-mass spectrometry (GCMS), and liquid chromatography-mass spectrometry (LCMS), high performance liquid chromatography (HPLC), capillary electrophoresis, Matrix-Assisted Laser Desorption Ionization time-of-flight mass spectrometry (MALDI-TOF MS), nuclear magnetic resonance (NMR), near-infrared (NIR) spectroscopy, viscometry [Knothe, 1997; Knothe, 1999], titration for determining free fatty acids [Komers, 1997], enzymatic methods [Bailer, 1991], physical property-based methods, wet chemical methods, etc.

Sequences Provided by the Invention

Table 4 provides a summary of SEQ ID NOs: 1-5 disclosed herein.

TABLE 4

Sequences

| SEQ ID NO | Sequence |
| --- | --- |
| 1 | Codon optimized *Escherichia coli* DXS gene |
| 2 | Codon optimized *Escherichia coli* IDI gene |
| 3 | Codon optimized *Populus nigra* IspS gene |
| 4 | Codon optimized *Picea abies* TPS-bis gene |
| 5 | *Chloroflexus aurantiacus* PCS amino acid sequence |

EXAMPLES

The examples below are provided herein for illustrative purposes and are not intended to be restrictive.

Example 1: Optimization of Growth Medium for *Paracoccus* sp. when Using Formate as the C1 Compound

*Paracoccus zeaxanthinifaciens* ATCC 21588, *Paracoccus versutus* ATCC 25364, and *Paracoccus denitrificans* ATCC 13534 were obtained from the American Type Culture Collection (ATCC).

Strains were tested for the ability to grow aerobically on sodium formate as a sole source of carbon and/or energy using MOPS minimal medium (Teknova, Inc.) with sodium formate as a sole carbon source at 37 C. Unlike previous media used to evaluate the formate-dependent growth of *Paracoccus*, this medium contains defined levels of trace elements molybdenum, boron, copper, zinc, manganese, and other trace metals.

Growth was conducted in various high-throughput machinery capable of monitoring growth by light scattering at 600 nm, including a Gemini SpectraNax plate reader (Molecular Devices, Inc.), a Tecan M3000 plate reader (Tecan, Inc.), and a BioLector device (m2p-labs, Inc.). For the BioLector, the $CO_2$ gas content in the culture headspace was controllable, as was the humidity.

*Paracoccus zeaxanthinifaciens* ATCC 21588 was incapable of growth on formate as a sole carbon or energy source. The other two *Paracoccus* strains were capable of growth on formate as a sole carbon source, as has been previously reported [Microbiology, 1979, 114(1):1-13, DOI: 10.1099/00221287-114-1-1; Arch Microbiol, 1978, 118(1): 21-26, DOI: 10.1007/BF00406069].

The effect on growth rate of changes in temperature (T, in degrees Celsius), the partial pressure of $CO_2$ in the culture headspace gas ($pCO_2$, in percent by volume), shaking speed (in rpm), and/or the concentrations (in mM) of sodium formate (HCOONa), sodium nitrate ($NaNO_3$), sodium thiosulfate ($Na_2S_2O_3$), sodium chloride (NaCl), and sodium bicarbonate ($NAHCO_3$) added to the Basal MOPS minimal medium were systematically evaluated. Combinations examined are shown in Table 2. *Paracoccus* strains are labelled according to their ATCC number. For each measurement, the instrument used (BioLector; SpectraMax; Tecan), plate type (Flower, Flower Plate; 96 transp, 96-well transparent microtiter plate; 96 opaque, 96-well opaque microtiter plate), use of plate lid, use of humidity control and total culture volume in uL is indicated. N/A indicates that a particular experimental condition is not applicable for the instrument used.

TABLE 2

Tested growth conditions for each Paracoccus strain

| ATCC | NaHCO3 | NaCl | NaNO3 | Na2S2O3 | HCOONa | T | Shaking speed | Instrument | Plate | Lid | Humidity Control | pCO2 | Vol |
| --- | --- | --- | --- | --- | --- | --- | --- | --- | --- | --- | --- | --- | --- |
| 25364 | 0.0 | 0.0 | 0.0 | 0.0 | 50.0 | 37.0 | 1200 | BioLector | Flower | N/A | TRUE | 5% | 1300 |
| 25364 | 150.0 | 0.0 | 0.0 | 0.0 | 50.0 | 37.0 | 1200 | BioLector | Flower | N/A | TRUE | 5% | 1300 |
| 25364 | 0.0 | 60.0 | 0.0 | 0.0 | 50.0 | 37.0 | 1200 | BioLector | Flower | N/A | TRUE | 5% | 1300 |
| 25364 | 0.0 | 0.0 | 60.0 | 0.0 | 50.0 | 37.0 | 1200 | BioLector | Flower | N/A | TRUE | 5% | 1300 |
| 25364 | 0.0 | 0.0 | 0.0 | 80.0 | 50.0 | 37.0 | 1200 | BioLector | Flower | N/A | TRUE | 5% | 1300 |
| 25364 | 0.0 | 0.0 | 0.0 | 0.0 | 20.0 | 37.0 | 1200 | BioLector | Flower | N/A | TRUE | 5% | 1300 |
| 13534 | 0.0 | 0.0 | 0.0 | 0.0 | 50.0 | 37.0 | 1200 | BioLector | Flower | N/A | TRUE | 5% | 1300 |
| 13534 | 150.0 | 0.0 | 0.0 | 0.0 | 50.0 | 37.0 | 1200 | BioLector | Flower | N/A | TRUE | 5% | 1300 |

TABLE 2-continued

Tested growth conditions for each Paracoccus strain

| ATCC | NaHCO$_3$ | NaCl | NaNO$_3$ | Na$_2$S$_2$O$_3$ | HCOONa | T | Shaking speed | Instrument | Plate | Lid | Humidity Control | pCO$_2$ | Vol |
|---|---|---|---|---|---|---|---|---|---|---|---|---|---|
| 13534 | 0.0 | 60.0 | 0.0 | 0.0 | 50.0 | 37.0 | 1200 | BioLector | Flower | N/A | TRUE | 5% | 1300 |
| 13534 | 0.0 | 0.0 | 60.0 | 0.0 | 50.0 | 37.0 | 1200 | BioLector | Flower | N/A | TRUE | 5% | 1300 |
| 13534 | 0.0 | 0.0 | 0.0 | 80.0 | 50.0 | 37.0 | 1200 | BioLector | Flower | N/A | TRUE | 5% | 1300 |
| 13534 | 0.0 | 0.0 | 0.0 | 0.0 | 20.0 | 37.0 | 1200 | BioLector | Flower | N/A | TRUE | 5% | 1300 |
| 25364 | 0.0 | 0.0 | 0.0 | 0.0 | 50.0 | 34.0 | 900 | BioLector | Flower | N/A | TRUE | 5% | 1300 |
| 25364 | 150.0 | 0.0 | 0.0 | 0.0 | 50.0 | 34.0 | 900 | BioLector | Flower | N/A | TRUE | 5% | 1300 |
| 25364 | 0.0 | 60.0 | 0.0 | 0.0 | 50.0 | 34.0 | 900 | BioLector | Flower | N/A | TRUE | 5% | 1300 |
| 25364 | 0.0 | 0.0 | 60.0 | 0.0 | 50.0 | 34.0 | 900 | BioLector | Flower | N/A | TRUE | 5% | 1300 |
| 25364 | 0.0 | 0.0 | 0.0 | 80.0 | 50.0 | 34.0 | 900 | BioLector | Flower | N/A | TRUE | 5% | 1300 |
| 25364 | 0.0 | 0.0 | 0.0 | 0.0 | 20.0 | 34.0 | 900 | BioLector | Flower | N/A | TRUE | 5% | 1300 |
| 13534 | 0.0 | 0.0 | 0.0 | 0.0 | 50.0 | 34.0 | 900 | BioLector | Flower | N/A | TRUE | 5% | 1300 |
| 13534 | 150.0 | 0.0 | 0.0 | 0.0 | 50.0 | 34.0 | 900 | BioLector | Flower | N/A | TRUE | 5% | 1300 |
| 13534 | 0.0 | 60.0 | 0.0 | 0.0 | 50.0 | 34.0 | 900 | BioLector | Flower | N/A | TRUE | 5% | 1300 |
| 13534 | 0.0 | 0.0 | 60.0 | 0.0 | 50.0 | 34.0 | 900 | BioLector | Flower | N/A | TRUE | 5% | 1300 |
| 13534 | 0.0 | 0.0 | 0.0 | 80.0 | 50.0 | 34.0 | 900 | BioLector | Flower | N/A | TRUE | 5% | 1300 |
| 13534 | 0.0 | 0.0 | 0.0 | 0.0 | 20.0 | 34.0 | 900 | BioLector | Flower | N/A | TRUE | 5% | 1300 |
| 25364 | 10.7 | 4.3 | 4.3 | 40.0 | 45.7 | 36.6 | 1157 | BioLector | Flower | N/A | TRUE | 5% | 1300 |
| 13534 | 75.0 | 4.3 | 4.3 | 5.7 | 45.7 | 36.6 | 1157 | BioLector | Flower | N/A | TRUE | 5% | 1300 |
| 13534 | 10.7 | 4.3 | 30.0 | 5.7 | 45.7 | 36.6 | 1157 | BioLector | Flower | N/A | TRUE | 5% | 1300 |
| 25364 | 42.9 | 17.1 | 17.1 | 0.0 | 32.9 | 35.3 | 1029 | BioLector | Flower | N/A | TRUE | 5% | 1300 |
| 13534 | 0.0 | 17.1 | 17.1 | 22.9 | 32.9 | 35.3 | 1029 | BioLector | Flower | N/A | TRUE | 5% | 1300 |
| 13534 | 42.9 | 17.1 | 0.0 | 22.9 | 32.9 | 35.3 | 1029 | BioLector | Flower | N/A | TRUE | 5% | 1300 |
| 25364 | 101.0 | 6.1 | 6.1 | 11.4 | 26.7 | 34.4 | 937 | BioLector | Flower | N/A | TRUE | 5% | 1300 |
| 25364 | 101.0 | 6.1 | 6.1 | 0.0 | 26.7 | 34.4 | 937 | BioLector | Flower | N/A | TRUE | 5% | 1300 |
| 13534 | 122.4 | 29.4 | 14.7 | 16.3 | 67.8 | 34.4 | 937 | BioLector | Flower | N/A | TRUE | 5% | 1300 |
| 13534 | 122.4 | 29.4 | 14.7 | 0.0 | 67.8 | 34.4 | 937 | BioLector | Flower | N/A | TRUE | 5% | 1300 |
| 21588 | 0.0 | 0.0 | 0.0 | 0.0 | 50.0 | 31.0 | unknown | Tecan | 96 transp | TRUE | N/A | N/A | 150 |
| 25364 | 0.0 | 0.0 | 0.0 | 0.0 | 50.0 | 31.0 | unknown | Tecan | 96 transp | TRUE | N/A | N/A | 150 |
| 13534 | 0.0 | 0.0 | 0.0 | 0.0 | 50.0 | 31.0 | unknown | Tecan | 96 transp | TRUE | N/A | N/A | 150 |
| 21588 | 0.0 | 0.0 | 0.0 | 0.0 | 50.0 | 31.0 | unknown | Tecan | 96 transp | TRUE | N/A | N/A | 150 |
| 25364 | 0.0 | 0.0 | 0.0 | 0.0 | 50.0 | 31.0 | unknown | Tecan | 96 transp | TRUE | N/A | N/A | 150 |
| 13534 | 0.0 | 0.0 | 0.0 | 0.0 | 50.0 | 31.0 | unknown | Tecan | 96 transp | TRUE | N/A | N/A | 150 |
| 21588 | 0.0 | 0.0 | 0.0 | 0.0 | 50.0 | 31.0 | N/A | SpectraMax | 96 transp | TRUE | N/A | N/A | 150 |
| 25364 | 0.0 | 0.0 | 0.0 | 0.0 | 50.0 | 31.0 | N/A | SpectraMax | 96 transp | TRUE | N/A | N/A | 150 |
| 13534 | 0.0 | 0.0 | 0.0 | 0.0 | 50.0 | 31.0 | N/A | SpectraMax | 96 transp | TRUE | N/A | N/A | 150 |
| 21588 | 0.0 | 0.0 | 0.0 | 0.0 | 50.0 | 31.0 | Linear (8.5) | Tecan | 96 transp | TRUE | N/A | N/A | 150 |
| 25364 | 0.0 | 0.0 | 0.0 | 0.0 | 50.0 | 31.0 | Linear (8.5) | Tecan | 96 transp | TRUE | N/A | N/A | 150 |
| 13534 | 0.0 | 0.0 | 0.0 | 0.0 | 50.0 | 31.0 | Linear (8.5) | Tecan | 96 transp | TRUE | N/A | N/A | 150 |
| 25364 | 0.0 | 0.0 | 0.0 | 0.0 | 50.0 | 37.0 | Linear (8.5) | Tecan | 96 opaque | TRUE | N/A | N/A | 150 |
| 25364 | 0.0 | 0.0 | 0.0 | 0.0 | 50.0 | 37.0 | Linear (8.5) | Tecan | 96 opaque | TRUE | N/A | N/A | 100 |
| 13534 | 0.0 | 0.0 | 0.0 | 0.0 | 50.0 | 37.0 | Linear (8.5) | Tecan | 96 opaque | TRUE | N/A | N/A | 150 |
| 13534 | 0.0 | 0.0 | 0.0 | 0.0 | 50.0 | 37.0 | Linear (8.5) | Tecan | 96 opaque | TRUE | N/A | N/A | 100 |
| 25364 | 0.0 | 0.0 | 0.0 | 0.0 | 50.0 | 37.0 | 1200 | BioLector | 96 opaque | TRUE | FALSE | FALSE | 150 |
| 25364 | 0.0 | 0.0 | 0.0 | 0.0 | 50.0 | 37.0 | 1200 | BioLector | 96 opaque | TRUE | FALSE | FALSE | 100 |
| 13534 | 0.0 | 0.0 | 0.0 | 0.0 | 50.0 | 37.0 | 1200 | BioLector | 96 opaque | TRUE | FALSE | FALSE | 150 |
| 13534 | 0.0 | 0.0 | 0.0 | 0.0 | 50.0 | 37.0 | 1200 | BioLector | 96 opaque | TRUE | FALSE | FALSE | 100 |
| 25364 | 0.0 | 0.0 | 0.0 | 0.0 | 50.0 | 37.0 | Linear (8.5) | Tecan | 96 opaque | TRUE | N/A | N/A | 150 |
| 25364 | 0.0 | 0.0 | 0.0 | 0.0 | 50.0 | 37.0 | Linear (8.5) | Tecan | 96 opaque | TRUE | N/A | N/A | 100 |
| 13534 | 0.0 | 0.0 | 0.0 | 0.0 | 50.0 | 37.0 | Linear (8.5) | Tecan | 96 opaque | TRUE | N/A | N/A | 150 |
| 13534 | 0.0 | 0.0 | 0.0 | 0.0 | 50.0 | 37.0 | Linear (8.5) | Tecan | 96 opaque | TRUE | N/A | N/A | 100 |
| 25364 | 0.0 | 0.0 | 0.0 | 0.0 | 50.0 | 37.0 | 800 | BioLector | 96 opaque | TRUE | TRUE | FALSE | 150 |
| 25364 | 0.0 | 0.0 | 0.0 | 0.0 | 50.0 | 37.0 | 800 | BioLector | 96 opaque | TRUE | TRUE | FALSE | 100 |
| 13534 | 0.0 | 0.0 | 0.0 | 0.0 | 50.0 | 37.0 | 800 | BioLector | 96 opaque | TRUE | TRUE | FALSE | 150 |
| 13534 | 0.0 | 0.0 | 0.0 | 0.0 | 50.0 | 37.0 | 800 | BioLector | 96 opaque | TRUE | TRUE | FALSE | 100 |
| 25364 | 0.0 | 0.0 | 0.0 | 0.0 | 50.0 | 37.0 | 1200 | BioLector | 96 opaque | FALSE | TRUE | FALSE | 150 |
| 25364 | 0.0 | 0.0 | 0.0 | 0.0 | 50.0 | 37.0 | 1200 | BioLector | 96 opaque | FALSE | TRUE | FALSE | 100 |
| 13534 | 0.0 | 0.0 | 0.0 | 0.0 | 50.0 | 37.0 | 1200 | BioLector | 96 opaque | FALSE | TRUE | FALSE | 150 |
| 13534 | 0.0 | 0.0 | 0.0 | 0.0 | 50.0 | 37.0 | 1200 | BioLector | 96 opaque | FALSE | TRUE | FALSE | 100 |
| 25364 | 0.0 | 0.0 | 0.0 | 0.0 | 50.0 | 37.0 | 1200 | BioLector | Flower | N/A | TRUE | FALSE | 1300 |
| 13534 | 0.0 | 0.0 | 0.0 | 0.0 | 50.0 | 37.0 | 1200 | BioLector | Flower | N/A | TRUE | FALSE | 1300 |

The particular values for salt, bicarbonate, formate, thiosulfate, or nitrate concentration, as well as temperature, were chosen by implementing a Nelder-Mead simplex optimization algorithm (as described in Chapter 18 of Chemometrics: a textbook ISBN: 0444426604) using the starting simplices with points chosen from the following possibilities: temperature, 34° C. or 37° C.; sodium bicarbonate, 150 mM or 0 mM; sodium chloride, 60 mM or 0 mM; sodium formate, 20 mM or 50 mM; sodium nitrate, 60 mM or 0 mM; sodium thiosulfate, 0 mM or 80 mM; shaking speed, 1200 rpm or 900 rpm. Growth was evaluated for both 25364 and 13534 at each chosen medium condition. For each strain and medium condition, a score indicative of the growth was calculated as the time (in hours) to 50% of the maximum growth attained in the entire experiment minus the time to 5% of the maximum growth. This metric is easy to compute and avoids penalizing conditions with longer lag phases.

From the scores, new medium conditions were calculated according to the Nelder-Mead simplex algorithm. These medium conditions were tested as well. The growth under the new condition as well as the old ones was used to define the points of a new simplex, and the process repeated.

After several rounds of the medium optimization process, a satisfactory medium condition, allowing for faster growth than the initially chosen medium conditions, was obtained. In total, 68 different unique medium/strain/temperature/shaking conditions were examined. The fastest growth on formate as a sole carbon source was obtained for ATCC strain 25364. Under the optimal conditions, the medium consisted of 100 mM sodium bicarbonate, 6 mM sodium chloride, 6 mM sodium nitrate, 11 mM sodium thiosulfate, and 26 mM sodium formate in addition to standard MOPS minimal medium components. The optimal growth temperature was 34° C. Under these conditions, ATCC strain 25364 had a growth rate of >0.7 hr$^{-1}$, corresponding to a doubling time of 0.95 hr.

ATCC strain 25364 was found capable of growth at rates in excess of 0.4 hr$^{-1}$ using a simpler medium composition of MOPS minimal medium plus 50 mM sodium formate.

Large concentrations of thiosulfate were found to give slowed, biphasic growth curves for both strains of *Paracoccus* tested. In general, moderate concentrations of sodium nitrate showed improved growth. Growth at 34° C. was slightly better than growth at 37° C., and both of these temperatures were significantly better than growth at 30° C.

Example 2: Automatable Protocol for Conjugative Transfer of Plasmids from *E. coli* Donors to *Paracoccus* sp.

*E. coli* strain S17-1 was obtained from the Yale *E. coli* Genetic Stock Center. *Paracoccus denitrificans* PD1222 was obtained from Stephen Spiro (University of Texas at Dallas). *E. coli* S17-1 strain is tra+, meaning it is able to mobilize for conjugative transfer those plasmids harboring a mob+ genotype. Plasmid pDIY313K, obtained from Dariusz Bartosik (University of Warsaw, Poland) and described by his laboratory [J Microbiol Methods, 2011, 86(2):166-74, DOI: 10.1016/j.mimet.2011.04.016], and introduced into *E. coli* S17-1 by standard methods.

*E. coli* S17-1 was grown on Luria broth with carbenicillin overnight. *Paracoccus versutus* ATCC 25364 was grown overnight on MOPS minimal medium (Teknova, Inc.) with 50 mM sucrose and 40 mM sodium nitrate.

The next day, *E. coli* S17-1 was subcultured in antibiotic-free Luria broth for >4 hr. *Paracoccus* strains were subcultured in identical MOPS/sucrose/nitrate medium. After cultures of both *E. coli* and *Paracoccus* had reach log phase, with optimal density greater than 1.0 cm$^{-1}$, cultures were mixed in equal volumes in wells of a standard, SBS-format 96-well plate. No effort was made to pellet the cells, to immobilize cells on porous filters, to culture the cells on solid media, or to otherwise manipulate the mixtures. Cultures were simply mixed in equal volumes and incubated overnight at 37° C. without agitation.

After overnight incubation, the mixed cultures were diluted in PBS and dilutions were plated on MOPS/sucrose/kanamycin agar. *E. coli* cannot use sucrose as a carbon source, and only strains carrying pDIY313K can grow in the presence of kanamycin. Thus on these plates only transconjugants—strains of *Paracoccus* containing plasmid DNA and expressing plasmid-derived kanamycin resistance genes—can grow. In parallel we plated the same dilutions on MOPS/sucrose agar without kanamycin, in order to calculate the cell concentration of total *Paracoccus* cells used in the experiment and to calculate the transconjugation frequency (colonies of plasmid-bearing *Paracoccus* isolated per colony of recipient *Paracoccus* cell).

Using this simple technique we were able to demonstrate conjugation frequencies of 10$^{-5}$ using *Paracoccus denitrificans* PD1222 and 2×10$^{-7}$ using *Paracoccus versutus*. It should be emphasized that this frequency was determined via a protocol which did not require non-selective growth on soft medium, the use of filters, or any centrifugation steps. These steps are required in protocols for conjugation frequently taught in the literature. For example, Bartosik [J Microbiol Methods, 2011, 86(2): 166-74, DOI: 10.1016/j.mimet.2011.04.016] teaches that cells must be grown, pelleted by centrifugation, washed, resuspendend, mixed, immobilized on a porous filter, grown under non-selective agar overnight, removed from the filter by washing, pelleted, and finally plated on selective medium. The lack of any such laborious cell manipulation procedures in our protocol is essential for conduction of the protocol on a robotics-based liquid-handling platform, where centrifugation and resuspension operations are much more error-prone, hard to implement, and/or unreliable in comparison with simple liquid handling steps.

Example 3: Genome Sequencing of *Paracoccus* Strains

Genomic DNA was isolated from *Paracoccus zeaxanthinifaciens* ATCC 21588, *Paracoccus versutus* ATCC 25364, and *Paracoccus denitrificans* ATCC 13534 using a Wizard Genomic DNA Isolation Kit (Promega, Inc.). The resulting DNA samples were fragmented and converted to paired-end libraries for whole-genome shotgun sequencing on a 454 pyrosequencing platform (Roche, Inc.).

For *Paracoccus denitrificans*, 37,585,886 paired reads, each 100 nt in length, were obtained. This represents approximately 3.7 gigabases of sequence data, or approximately 730-fold coverage of the 5.2 megabase genome of *Paracoccus denitrificans* PD1222 (Genbank accession numbers CP000489, CP000490, and CP000491 for chromosome 1, chromosome 2, and a 653,815 bp megaplasmid, respectively). Reads were assembled first by de-novo assembly and second by mapping the de-novo contigs to the published PD1222 genome.

The resulting reads could be assembled into a crude whole-genome assembly of 351 scaffolds comprising 21,972,742 total reads. The maximum scaffold was 7974 nt and minimum-length scaffold 2004 nt.

Example 4: Analysis of Methylerythritol Pathway in *Paracoccus*

The *Paracoccus denitrificans* PD1222 genome has been published. Through manual inspection and BLAST searching we found homologs to all but one member of the methylerythritol pathway for isoprenoid biosynthesis. The *Paraoccus* gene homologs are shown in Table 3. Gene names refer to standard names given to *E. coli* genes (see accession Genbank accession U000096 for more information). Names for *Paracoccus* genes correspond to the nomenclature annotated as part of the *Paracoccus* PD1222 genome sequence, available at Genbank accession numbers CP000489 for chromosome 1 and CP000490 for chromosome 2.

TABLE 3

Methylerythritol pathway gene homologs in *Paracoccus denitrificans* PD122

| E. coli gene | P. denitrificans PD1222 gene | PD1222 chromosome # |
|---|---|---|
| dxs | Pden_0400 | 1 |
| dxr | Pden_3997 | 2 |
| ispD | Pden_3667 (KEGG); none (Metacyc) | 2 |
| ispE | Pden_0423 | 1 |
| ispF | Pden_3667 | 2 |
| ispG | Pden_1820 | 1 |
| ispH | Pden_3619 | 2 |
| idi | no type I or type II homologues | ? |
| ispA | Pden_0399 | 1 |

The sole member of the methylerythritol pathway missing a homolog from the *P. denitrificans* PD1222 genome is the gene idi, encoding isopentenyl-diphosphate Δ-isomerase (E.C. 5.3.3.2). It is responsible for interconverting isopentenyl diphosphate (IPPP) and dimethylallyl diphosphate (DMAP). However, several studies have shown that this gene is not required for pathway activity, since the preceding pathway step, coded for in *E. coli* by the ispH gene that shares homology with predicted *Paracoccus* gene Pden_3619, generates both IPPP and DMAP to some degree [Lipids, 2008, 43(12):1095-1107, DOI: 10.1007/s11745-008-3261-7].

*P. denitrificans* is known to contain prenylated quinones as constituents of its cell membrane [Biochem Eng J, 2003, 16(2):183-190, DOI: 10.1016/S1369-703X(03)00035-4]. These compounds are indicative of terpene production. The presence of gene homologs for the methylerythritol pathway indicate that this pathway is responsible for formation of terpenoids in this organism.

Example 5: Selection for Populations of *Paracoccus* Versutus with Improved Doubling Times on Electrolytically Generated Formate A computer-controlled continuous culture device that can be operated as a chemostat or a turbidostat was constructed. The device has a working volume between 20 and 50 mL (not yet tested above 50 mL). The device uses air pressure to move liquids throughout the fluidics system, and an array of solenoid valves to direct fluid flow. The culture is mixed and aerated by the turbulence created by sparging with air at a flow rate of >10 vvm. The valves are controlled by an Arduino Mega 2560 microprocessor. The Arduino also interfaces with the sensors and control mechanisms of the device. The optical density (OD) of the culture is determined by an infrared LED-photodiode pair which measures the transmittance of light across the culture vessel.

From Edward Rode at DNV, Inc. (formerly Det Norske Veritas), we obtained two samples of formate generated by DNV from electricity and carbon dioxide by electrolysis. The first solution received from DNV contained 0.5 M potassium chloride (electrolyte), 0.5 M potassium formate, and 2.5 M sodium bicarbonate. The second solution as received from DNV contained approximately 0.5 M potassium chloride (electrolyte), and 0.56 M potassium formate. This solution was directly obtained from the cathodic chamber of DNV's electrolysis reactor without any upgrading or purifying, and thus it may contain other uncharacterized contaminants or other agents which inhibit the growth of bacteria. These may arise from metals or plastics leaching into solution, from uncharacterized electrochemical reactions going on in parallel with the cathodic reduction of bicarbonate (i.e. dissolved $CO_2$) to formate salts, or from other processes. The ability for engineered cells to operate directly on such solutions would be of interest for the development of low-cost electricity-to-chemicals bioconversion processes.

We verified that electrolytically generated formate reduces the growth rate of *Paracoccus* versutus. Overnight cultures of MOPS minimal formate medium were inoculated into MOPS minimal medium containing either various dilutions of sodium formate (Sigma-Aldrich) or various dilutions of formate sourced from DNV's first sample. Growth was uninhibited by pure sodium formate at the highest concentration tested, 50 mM. In contrast growth was strongly inhibited by electrolytically generated formate, with no growth observed above 20 mM formate concentration, and only weak growth at concentrations above 10 mM. However at lower concentrations, electrolytic formate supported *Paracoccus* growth at rates similar to pure sodium formate.

In an effort to select for strains with an increased ability to thrive on electrolytically generated formate, *Paracoccus* versutus was inoculated into the culture device. MOPS minimal medium with commercial (Sigma-Aldrich) sodium formate at 50 mM flowed through the device at flow rates controlled by the Arduino in order to maintain with a target OD setpoint between 0.2 and 0.3 $cm^{-1}$. In practice this flow rate was between 6 to 9 mL $hr^{-1}$. The working volume of the device was 24 mL, meaning the dilution rate was between 0.25 $hr^-$ and 0.3 $hr^-$. Periodically throughout the continuous culture, samples of the culture were taken and preserved as a glycerol stock at -80° C.

After 48 generations of growth, the medium feed was changed to be a mixture of 75 volume % MOPS minimal medium with 50 mM sodium formate, and 25 volume % MOPS minimal medium with 50 mM electrolytic formate (from DNV's second sample). The culture was incubated continuously for 32 more generations of growth.

After the conclusion of the experiment, glycerol stocks previously taken from the reactor population and reserved at -80° C. were revived and cultured in MOPS formate minimal medium to determine if any improvements in growth on formate had taken place. We found that the *P. versutus* population sampled from the turbidostat zero generations of growth had much lower growth rates on 50 mM electrolytic formate (MOPS-EF) medium than on 50 mM pure sodium formate (MOPS-PF) medium (0.32 $hr^-$ for MOPS-PF vs. 0.26 $hr^-$ for MOPS-EF). Populations sampled from the reactor at later times had faster growth rates, as shown in Table 4. Clones from this population can be used as hosts for production of fuels or other carbon products of interest because of their ability to better tolerate solutions of electrolytic formate as their sole source of carbon and energy, and their ability to grow more quickly than wild-type *P. versutus* under these conditions.

TABLE 4

Growth rates of evolved *Paraoccus* strains

| Generations of Selection, total | Generations of Selection on MOPS-EF | MOPS-EF Growth Rate, $hr^{-1}$ | MOPS-PF Growth rate, $hr^{-1}$ |
|---|---|---|---|
| 0 | 0 | 0.25 | 0.32 |
| 35 | 0 | 0.32 | 0.43 |
| 80 | 32 | 0.41 | 0.41 |

Example 6: High Intensity Bioreactor Cultivation of Paracoccus on Formate Salts To our knowledge, the high-cell density bioreactor cultivation of industrially relevant, genetically tractable microbes using formate as the sole source of carbon and energy has not been reported. We sought to demonstrate the high-cell density bioreactor cultivation of *Paracoccus versutus* under process-relevant conditions.

In a series of two experiments comprising 12 different fed-batch runs, the reactors were initially charged with 0.5 L of a formate minimal medium based on the recipe of R minimal medium, but with emendations of sodium molybdate, sodium selenite, thiamin, and cobalamin. The reactors were inoculated with overnight flask cultures of *Paracoccus versutus*. After the initial charge of formate in the reactor was consumed, supplemental feeding was begun by flowing 8.0 M ammonium formate to the reactors. Over the course of 12 experiments, we studied the effect of initial inoculum size, feeding rate, and aerobicity on rates of formate consumption and of biomass and $CO_2$ formation. We monitored formate consumption by HPLC, $CO_2$ emission through IR-based off-gas measurement, and biomass formation by total insoluble solids.

Initially, initial biomass concentration corresponding to OD 0.1 was used; however, biomass measurement by weight was unreliable due to mineral precipitation during fermentation. Subsequently, initial biomass concentration was OD1.0 and we used a dilute-acid wash during the processing of biomass samples in order to remove inorganic precipitates. We assumed that biomass contained 0.5 g-C $g^{-1}$. This assumption allowed us to close carbon balances around the aerobic, high-inoculum runs to within 10%, indicating that the assumption was reasonable and constituting a consistency check on our HPLC and off-gas measurements.

Figure 17:
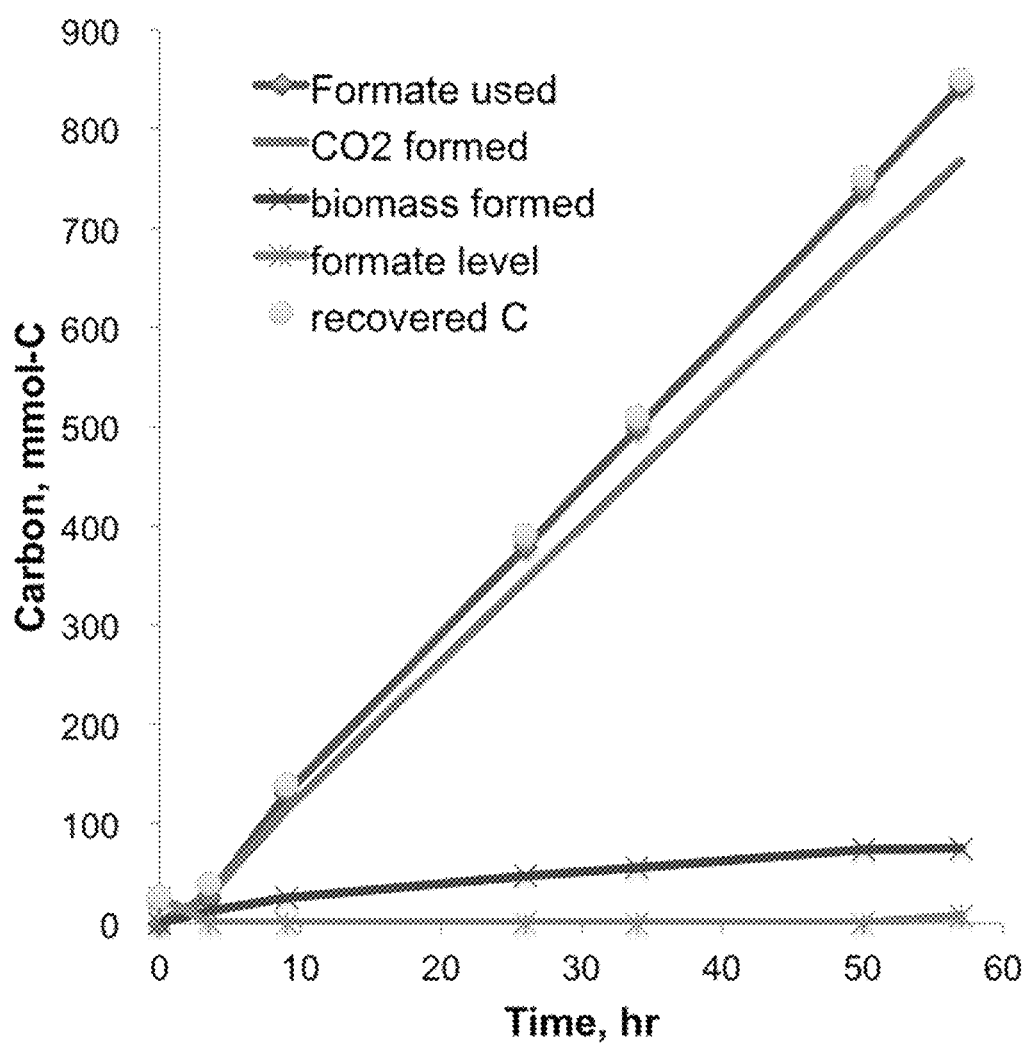
FIG. 17 depicts an example time course of formate usage, formate accumulation, biomass formation and CO2 emission for a 1-L aerobic, CSTR-type bioreactor initially charged with 0.5 L of minimal medium containing *Paracoccus versutus* and fed ammonium formate as a sole source of carbo and energy at a rate of 10 mM hr$^{-1}$. Over the course of the run the working volume changed from 0.5 L to 0.785 L. The data for this run corresponds to formate consumption rates of 1.6 g L$^{-1}$ hr$^{-1}$, maximum biomass concentrations of 2.5 gDCW L$^{-}$, and carbon fixation fluxes of 8 mmol-C gDCW$^{-1}$ L$^{-1}$.

FIG. 17 depicts sample fermentation data for an aerobic fermentation feed of 10 mM $hr^{-1}$. From the beginning of the formate feed at 3.45 hr post-inoculation to near the end of the run at 50 hr, the formate level remained below detection limits. The 75 mmol-C of biomass formed resulted in a final biomass concentration of 2.6 g $L^{-1}$, implying that specific formate consumption rates were at or above 0.51 g formate $gDCW^{-1}$ $hr^{-1}$ throughout the fermentation. In this run, 91% of the formate consumed was converted to $CO_2$ that left the reactor and 8.9% was accounted for by biomass formation. The total of biomass formation and $CO_2$ emisson accounted for 100.0% of the carbon used, a figure which varied between 100 and 103% across other runs. These rates correspond to a specific carbon fixation flux of 8 mmol C $gDCW^{-1}$ $hr^{-1}$ or a volumetric carbon fixation flux of >1.68 mmol $L^{-1}$ $hr^{-1}$.

Nominal feed rates of 10, 30, and 100 mM $hr^{-1}$ were studied for aerobic fermentations. Only the 100 mM $hr^{-1}$ condition showed any evidence of formate accumulation, although this feed was only tried with a low-inoculum size condition (OD0.1). The 10 and 30 mM $hr^{-1}$ feed rates did not show any formate accumulation until the end of the fermentations, indicating that the capacity of the culture for formate utilization was greater than 30 mM hr under the densities used for cultivation.

Respiration of formic acid or formate is a proton-consuming, i.e. pH increasing process. In these experiments, the medium pH was held constant at 7.0 by the addition of concentrated phosphoric acid. Ammonium formate was chosen as a formate source because it provides an additional means of pH control (ammonium formate solutions are neutral in pH) and because it was hoped that as formate was consumed, ammonium would not accumulate due to the potential for offgassing of ammonia. We measured ammonium accumulation in the reactors by ion chromatography. At pH 7.0, ammonium offgassing did not occur to an appreciable extent, because 86-102% of the fed ammonium formate accumulated as ammonium in the medium. Ammonium accumulation likely limited the end-point biomass titer attained in most of the fermentations, as it accumulated to supra-molar concentrations in many of the vessels.

*Paracoccus versutus* can grow anaerobically using nitrate as an electron acceptor. We carried out nitrate-based anaerobic formate bioconversion using feeds that contained 8.0 M ammonium formate and 3.1 M sodium nitrate. When feeding was begun, the reactors were brought under anaerobiosis by sparging with nitrogen. Anaerobic fermentations also consumed formate at high rates, up to 0.67 g $L^{-1}$ $hr^{-1}$ in the experiments described here. Maximal biomass attained under anaerobic conditions was 1.3 gDCW $L^{-1}$. The low nitrogen sparging flow rates were incompatible with $CO_2$ measurement in the off-gas, so carbon balances are not available.

Initial results indicated that nitrate was converted to nitrite and that nitrite accumulated stoichiometrically in the reactor and was not further reduced. We successfully eliminated nitrite accumulation in the reactor by doubling the amount of copper in the medium and reducing the level of nitrate from 3.1 M to 3.0 M. These results demonstrate that *Paracoccus* is capable of anaerobic formate consumption with complete nitrate respiration to dinitrogen gas. Ammonium, formate and nitrate reached levels of 1100, 1500 and 540 mmol $L^{-1}$, respectively.

Example 7: Computing Mass Transfer Limitations of Synthesis Gas Versus Formate as a Feedstock The mass transfer limitations of synthesis gas (composed of molecular hydrogen and carbon monoxide) from the gas to liquid phase is illustrated here. For the purpose of this analysis, an ideal engineered organism that has an unlimited capacity to (i) metabolize dissolved aqueous-phase synthesis gas and (ii) convert it to a desired fuel at 100% of the theoretical yield is assumed. Under these conditions, the rate of fuel production per unit of reactor volume can depend solely on the rate at which synthesis gas can be transferred from the gas phase to the liquid phase.

Fuel productivity P in units of g-$L^{-1}$·$h^{-1}$ can be expressed as the product of fuel molecular weight $m_F$, fuel molar yield on synthesis gas $Y_{F/S}$, the biomass concentration in a bioreactor X, and the specific cellular uptake rate of synthesis gas $q_S$, as shown in the equation below.

$$P = m_F Y_{F/S} X q_S$$

At steady state, the bulk hydrogen uptake rate $Xq_S$ is equal to the rate of synthesis gas transfer from gas to liquid, meaning the productivity can be expressed as in the equation below, where C* is the liquid-phase solubility of synthesis gas, $C_L$ is the liquid-phase concentration of synthesis gas, and $K_L a$ is the mass transfer coefficient for synthesis gas transport from the gas phase (e.g., as bubbles sparged into the reactor) to the liquid. $K_L a$ is a complex function of reactor geometry, bubble size, superficial gas velocity, impeller speed, etc. and is best regarded as an empirical parameter that needs to be determined for a given bioreactor setup.

$$P = m_F Y_{F/S} K_L a (C^* - C_L)$$

Again, as a best-case scenario, an ideal engineered organism capable of maintaining rapid synthesis gas uptake rates even at vanishingly low synthesis gas concentrations (i.e. that $q_S$ is not a function of $C_L$ even as $C_L$ tends to zero) is assumed. This assumption maximizes the fuel productivity at $P=m_F Y_{F/S} K_L a C^*$.

For a fixed production target t, say 0.5 t d$^{-1}$ (equivalent to 20800 g h$^{-1}$), the productivity P determines the required reactor volume V because V=t/P. Thus, both fuel productivity and reactor volumes, even assuming "perfect" organisms, are bounded by achievable $K_L a$ values, as shown in the equations below.

$$P = (m_F Y_{F/S} C^*) K_L a$$

$$V = \frac{t}{(m_F Y_{F/S} C^*) K_L a}$$

Figure 18:
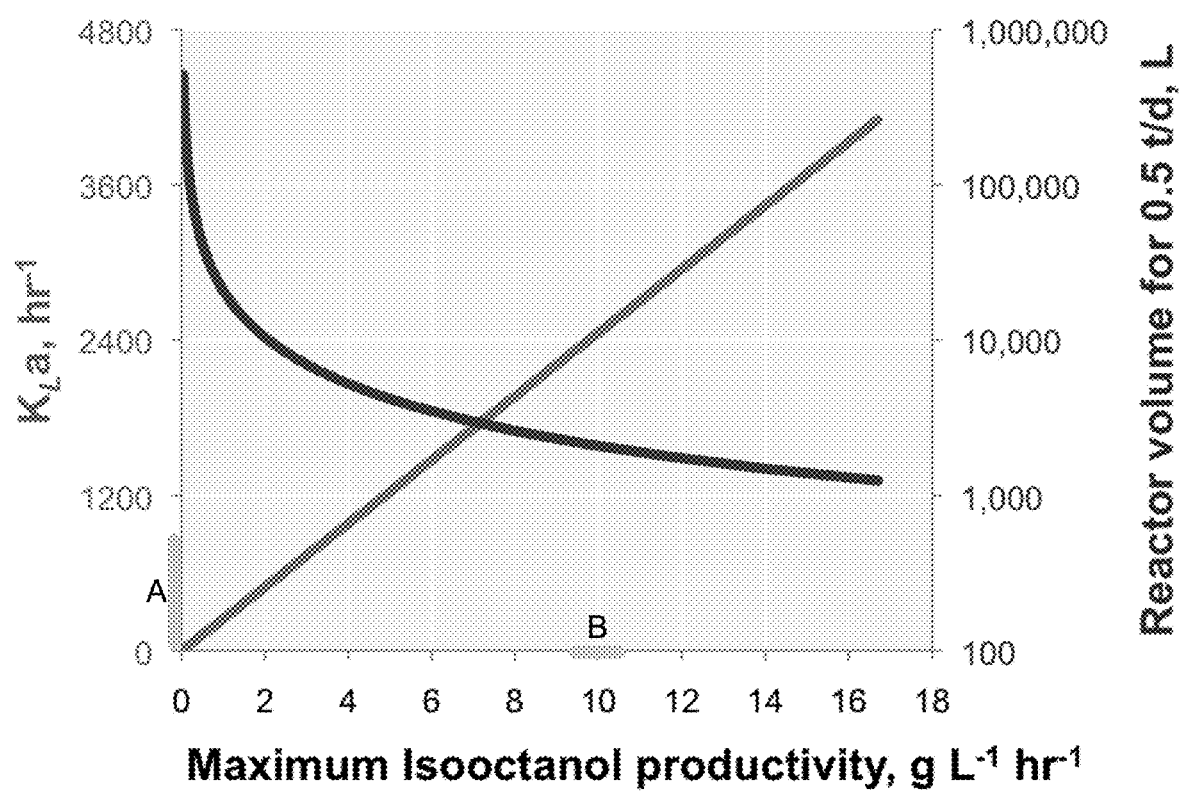
FIG. 18 depicts the required mass transfer coefficient ($K_L a$) and required reactor volume for 0.5 t/d of fuel production, as a function of maximum fuel productivity for isooctanol, assuming fuel production from synthesis gas for an ideal engineered organism. On the y axis, the typical range of $K_La$ in large-scale stirred-tank bioreactors is denoted (A). On the x axis, reported natural formate uptake rates at industrially relevant culture densities are denoted (B).

Maximal productivity corresponds to minimal reaction volumes, and occurs at maximal values of $m_F Y_{F/S} C^* K_L a$. The fuel yield cannot exceed the stoichiometric maximal yield. For the fuel isooctanol, the stoichiometric maximal yield is determined from the balanced chemical equation 8 $CO+16H_2 \rightarrow C_8H_{18}O+7 H_2O$, which shows that 16 moles of $H_2$ and 8 moles of CO are required for each mole of isooctanol produced. At atmospheric pressure, $C^*$ is unlikely to greatly exceed 0.75 mM, the solubility of $H_2$ in pure water (CO has approximately the same solubility as $H_2$). Using these representative values for representative values for $m_F$, $Y_{F/S}$, $C^*$ and t, the relationships between $K_L a$ and P as well as between $K_L a$ and t are shown (FIG. 18).

Alternative electron donors have the potential to solve both the safety problem and the mass transfer problem presented by hydrogen. An ideal non-synthesis gas vector for carrying electrical energy would have (a) a highly negative standard reduction potential and (b) established high-efficiency technology to for converting electricity into the vector. Unlike synthesis gas, however, it would (c) have a low propensity to explode when mixed with air, and (d) have high water solubility under bio-compatible conditions. Formic acid, HCOOH, or its salts, satisfies these conditions. Formic acid is stoichiometrically equivalent to $H_2+CO_2$, and formate has as standard reduction potential nearly identical to that of hydrogen. Since both formic acid and formate salts are highly soluble in water, the mass transfer limitations discussed above for hydrogen do not apply. However, a modified form of the fuel productivity equation, written for formic acid (A) instead of hydrogen (H), still applies, as shown below.

$$P = m_F Y_{F/A} X q_A$$

Unlike hydrogen-powered electrofuels bioproduction, limits on formate-powered fuel productivity P stem only from the attainable yield, the biomass concentration in the reactor, and the specific uptake rate. We assume $Y_{F/A}$, the molar yield of fuel on formic acid, is the stoichiometric maximum, whose value is the same as for hydrogen, 0.0467 mol isooctanol (mol HCOOH)$^{-1}$. For high-cell density cultivations of *E. coli*, biomass concentrations of X=50 gDCW L$^{-1}$ are attainable, although these values have not been observed for growth on formate or in minimal medium. For *Paracoccus versutus*, naturally capable of growing on formate, observed values of were 0.0368 mol formate-gDCW$^{-1}$·h$^{-1}$ [Kelly, 1979]. The representative values for $q_A$ and X imply a maximal isooctanol productivity on formate of about 10 g·L$^{-1}$·h$^{-1}$.

On the y-axis of FIG. 18, the range of reported $K_L a$ attainable in large-scale stirred-tank bioreactors is shown. Although there are many reports of higher $K_L a$ values in laboratory-scale reactors, during scale up the inevitable increase in volume-to-surface area ratios means that maintaining high $K_L a$ values is for practical purposes impossible. The maximum of the indicated range of 10-800 h$^{-1}$ translates to a best-case productivity of 4 g·L$^{-1}$·h$-1$, which implies a best-case reactor volume of 6,400 L. The best-case productivity on formate is 10 g·L$^{-1}$·h$^{-1}$, implying a reactor volume less than half as large would be required to achieve the same production. Most sources that give $K_L a$ values for large scale reactors have values much closer to 100 h$^{-1}$, meaning the best-case productivity using formate as the energy source would be more than 15 times larger than on synthesis gas.

Example 8: Engineered Organisms Producing Butanol

The enzyme beta-ketothiolase (*R. eutropha* PhaA or *E. coli* AtoB) (E.C. 2.3.1.16) converts 2 acetyl-CoA to acetoacetyl-CoA and CoA. Acetoacetyl-CoA reductase (*R. eutropha* PhaB) (E.C. 1.1.1.36) generates R-3-hydroxybutyryl-CoA from acetoacetyl-CoA and NADPH. Alternatively, 3-hydroxybutyryl-CoA dehydrogenase (*C. acetobutylicum* Hbd) (E.C. 1.1.1.30) generates S-3-hydroxybutyryl-CoA from acetoacetyl-CoA and NADH. Enoyl-CoA hydratase (*E. coli* MaoC or *C. acetobutylicum* Crt) (E.C. 4.2.1.17) generates crotonyl-CoA from 3-hydroxybutyryl-CoA. Butyryl-CoA dehydrogenase (*C. acetobutylicum* Bcd) (E.C. 1.3.99.2) generates butyryl-CoA and NAD(P)H from crotonyl-CoA. Alternatively, trans-enoyl-coenzyme A reductase (*Treponema denticola* Ter) (E.C. 1.3.1.86) generates butyryl-CoA from crotonyl-CoA and NADH. Butyrate CoA-transferase (*R. eutropha* Pct) (E.C. 2.8.3.1) generates butyrate and acetyl-CoA from butyryl-CoA and acetate. Aldehyde dehydrogenase (*E. coli* AdhE) (E.C. 1.2.1.{3,4}) generates butanal from butyrate and NADH. Alcohol dehydrogenase (*E. coli* adhE) (E.C. 1.1.1.{1,2}) generates 1-butanol from butanal and NADH, NADPH. Production of 1-butanol is conferred by the engineered host cell by expression of the above enzyme activities.

To create butanol-producing cells, host cells can be further engineered to express acetyl-CoA acetyltransferase (atoB) from *E. coli* K12, β-hydroxybutyryl-CoA dehydrogenase from *Butyrivibrio fibrisolvens*, crotonase from *Clostridium beijerinckii*, butyryl CoA dehydrogenase from *Clostridium beijerinckii*, CoA-acylating aldehyde dehydrogenase (ALDH) from *Cladosporium fulvum*, and adhE encoding an aldehyde-alcohol dehydrogenase of *Clostridium acetobutylicum* (or homologs thereof).

Example 9: Engineered Organisms Producing Acrylate

Enoyl-CoA hydratase (*E. coli* paaF) (E.C. 4.2.1.17) converts 3-hydroxypropionyl-CoA to acryloyl-CoA. Propionyl-CoA synthase (E.C. 6.2.1.-, E.C. 4.2.1.- and E.C. 1.3.1.-) also converts 3-hydroxypropionyl-CoA to acryloyl-CoA (AAL47820, SEQ ID NO:5). Acrylate CoA-transferase (*R. eutropha* pct) (E.C. 2.8.3.n) generates acrylate+acetyl-CoA from acryloyl-CoA and acetate.

Other Embodiments

The examples have focused on *Paracoccus*. Nevertheless, the key concept of using genetically engineering to confer production of carbon-based products of interest to a methylotroph is extensible to other methylotrophs such as other prokaryotes or eukaryotic single cell organisms such as methylotrophic yeast. Alternatively, the energy conversion and/or carbon fixation pathways described in U.S. Pat. No. 8,349,587 may be used to enhance or augment the methylotrophic capability of an organism that is natively methylotrophic; U.S. Pat. No. 8,349,587 is hereby incorporated by reference in its entirety.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EQUIVALENTS

The present invention provides among other things novel methods and systems for synthetic biology. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

The Sequence Listing filed as an ASCII text file via EFS-Web (file name: "010401SequenceListing"; date of creation: Dec. 2, 2013; size: 25,461 bytes) at the U.S. Patent and Trademark Office as the Receiving Office is hereby incorporated by reference in its entirety.

All publications, patents and patent applications referenced in this specification are incorporated herein by reference in their entirety for all purposes to the same extent as if each individual publication, patent or patent application were specifically indicated to be so incorporated by reference.

REFERENCES CITED

Aharoni A, Keizer L C, Bouwmeester H J, Sun Z, Alvarez-Huerta M, Verhoeven H A, Blaas J, van Houwelingen A M, De Vos R C, van der Voet H, Jansen R C, Guis M, Mol J, Davis R W, Schena M, van Tunen A J, O'Connell A P. Identification of the SAAT gene involved in strawberry flavor biogenesis by use of DNA microarrays. Plant Cell. 2000 May; 12(5):647-62.

Andersen J B, Steinberg C, Poulsen L K, Bjorn S P, Givskov M, Molin S. New unstable variants of green fluorescent protein for studies of transient gene expression in bacteria. Appl Environ Microbiol. 1998 June; 64(6):2240-6.

Anderson J C, Voigt C A, Arkin A P. Environmental signal integration by a modular AND gate. Mol Syst Biol. 2007; 3:133.

Bai F W, Anderson W A, Moo-Young M. Ethanol fermentation technologies from sugar and starch feedstocks. Biotechnol Adv. 2008 January-February; 26(1):89-105.

Bailer J, de Hueber K. Determination of saponifiable glycerol in "bio-diesel." Fresenius J Anal Chem. 1991; 340(3):186.

Bassham J A, Benson A A, Kay L D, Harris A Z, Wilson A T, Calvin M. The path of carbon in photosynthesis. XXI. The cyclic regeneration of carbon dioxide acceptor. J Am Chem Soc. 1954; 76:1760-70.

Bayer T S, Widmaier D M, Temme K, Mirsky E A, Santi D V, Voigt C A. Synthesis of methyl halides from biomass using engineered microbes. J Am Chem Soc. 2009 May 13; 131(18):6508-15.

Brock T. Biotechnology: A Textbook of Industrial Microbiology. Second Edition. Sinauer Associates, Inc. Sunderland, Mass. 1989.

Buchanan B B, Amon D I. A reverse KREBS cycle in photosynthesis: consensus at last. Photosynth Res. 1990; 24:47-53.

Camilli A, Bassler B L. Bacterial small-molecule signaling pathways. Science. 2006 Feb. 24; 311(5764):1113-6.

Canton B, Labno A, Endy D. Refinement and standardization of synthetic biological parts and devices. Nat Biotechnol. 2008 July; 26(7):787-93.

Cheesbrough T M, Kolattukudy P E. Alkane biosynthesis by decarbonylation of aldehydes catalyzed by a particulate preparation from *Pisum sativum*. Proc Natl Acad Sci USA. 1984 November; 81(21):6613-7.

Chen S, von Bamberg D, Hale V, Breuer M, Hardt B, Müller R, Floss H G, Reynolds K A, Leistner E. Biosynthesis of ansatrienin (mycotrienin) and naphthomycin. Identification and analysis of two separate biosynthetic gene clusters in *Streptomyces collinus* Tü 1892. Eur J Biochem. 1999 April; 261(1):98-107.

Chin J W, Cirino P C. Improved NADPH supply for xylitol production by engineered *Escherichia coli* with glycolytic mutations. Biotechnol Prog. 2011 March-April; 27(2):333-41.

Cropp T A, Wilson D J, Reynolds K A. Identification of a cyclohexylcarbonyl CoA biosynthetic gene cluster and application in the production of doramectin. Nat Biotechnol. 2000 September; 18(9):980-3.

Davis J H, Rubin A J, Sauer R T. Design, construction and characterization of a set of insulated bacterial promoters. Nucleic Acids Res. 2011 February; 39(3):1131-41. de Mendoza D, Klages Ulrich A, Cronan J E Jr. Thermal regulation of membrane fluidity in *Escherichia coli*. Effects of overproduction of beta-ketoacyl-acyl carrier protein synthase I. J Biol Chem. 1983 Feb. 25; 258(4):2098-101.

Dellomonaco C, Clomburg J M, Miller E N, Gonzalez R. Engineered reversal of the β-oxidation cycle for the synthesis of fuels and chemicals. Nature. 2011 Aug. 10; 476(7360):355-9.

Dennis M W, Kolattukudy P E. Alkane biosynthesis by decarbonylation of aldehyde catalyzed by a microsomal preparation from *Botryococcus braunii*. Arch Biochem Biophys. 1991 June; 287(2):268-75.

Denoya C D, Fedechko R W, Hafner E W, McArthur H A, Morgenstem M R, Skinner D D, Stutzman-Engwall K, Wax R G, Wemau W C. A second branched-chain alpha-keto acid dehydrogenase gene cluster (bkdFGH) from *Streptomyces avermitilis*: its relationship to avermectin biosynthesis and the construction of a bkdF mutant suitable for the production of novel antiparasitic avermectins. J Bacteriol. 1995 June; 177(12):3504-11.

Deshpande M V. Ethanol production from cellulose by coupled saccharification/fermentation using *Saccharomyces cerevisiae* and cellulase complex from *Sclerotium rolfsii* UV-8 mutant. Appl Biochem Biotechnol. 1992 September; 36(3):227-34.

Doolittle, R F (Editor). Computer Methods for Macromolecular Sequence Analysis. Methods in Enzymology. 1996; 266:3-711.

Edgar R C. MUSCLE: multiple sequence alignment with high accuracy and high throughput. Nucleic Acids Res. 2004 Mar. 19; 32(5):1792-7. (a)

Edgar R C. MUSCLE: a multiple sequence alignment method with reduced time and space complexity. BMC Bioinformatics. 2004 Aug. 19; 5:113. (b)

Edwards J S, Ramakrishna R, Palsson B O. Characterizing the metabolic phenotype: a phenotype phase plane analysis. Biotechnol Bioeng. 2002 Jan. 5; 77(1):27-36.

Evans M C, Buchanan B B, Amon D I. A new ferredoxin-dependent carbon reduction cycle in a photosynthetic bacterium. Proc Natl Acad Sci USA. 1966 April; 55(4): 928-34.

Fong S S, Palsson B Ø. Metabolic gene-deletion strains of *Escherichia coli* evolve to computationally predicted growth phenotypes. Nat Genet. 2004 October; 36(10): 1056-8.

Grantham R, Gautier C, Gouy M, Mercier R, Pave A. Codon catalog usage and the genome hypothesis. Nucleic Acids Res. 1980 Jan. 11; 8(1):r49-r62.

Greene D N, Whitney S M, Matsumura I. Artificially evolved *Synechococcus* PCC6301 Rubisco variants exhibit improvements in folding and catalytic efficiency. Biochem J. 2007 Jun. 15; 404(3):517-24.

Han L, Reynolds K A. A novel alternate anaplerotic pathway to the glyoxylate cycle in streptomycetes. J Bacteriol. 1997 August; 179(16): 5157-64.

Hawley D K, McClure W R. Compilation and analysis of *Escherichia coli* promoter DNA sequences. Nucleic Acids Res. 1983 Apr. 25; 11(8):2237-55.

Henry C S, Jankowski M D, Broadbelt L J, Hatzimanikatis V. Genome-scale thermodynamic analysis of *Escherichia coli* metabolism. Biophys J. 2006 Feb. 15; 90(4):1453-61.

Henstra A M, Sipma J, Rinzema A, Stams A J. Microbiology of synthesis gas fermentation for biofuel production. Curr Opin Biotechnol. 2007 June; 18(3):200-6.

Hoffmeister M, Piotrowski M, Nowitzki U, Martin W. Mitochondrial trans-2-enoyl-CoA reductase of wax ester fermentation from *Euglena gracilis* defines a new family of enzymes involved in lipid synthesis. J Biol Chem. 2005 Feb. 11; 280(6):4329-38.

Hügler M, Huber H, Molyneaux S J, Vetriani C, Sievert S M. Autotrophic $CO_2$ fixation via the reductive tricarboxylic acid cycle in different lineages within the phylum Aquificae: evidence for two ways of citrate cleavage. Environ Microbiol. 2007 January; 9(1):81-92.

Inokuma K, Nakashimada Y, Akahoshi T, Nishio N. Characterization of enzymes involved in the ethanol production of *Moorella* sp. HUC22-1. Arch Microbiol. 2007 July; 188(1):37-45.

Ivlev A A. Carbon isotope effects ($^{13}C/^{12}C$) in biological systems. Separation Sci Technol. 2010; 36:1819-1914.

Janausch I G, Zientz E, Tran Q H, Kroger A, Unden G C4-dicarboxylate carriers and sensors in bacteria. Biochim Biophys Acta. 2002 Jan. 17; 1553(1-2):39-56.

Jukes T H, Osawa S. Evolutionary changes in the genetic code. Comp Biochem Physiol B. 1993 November; 106(3):489-94.

Kalscheuer R, Steinbüchel A. A novel bifunctional wax ester synthase/acyl-CoA:diacylglycerol acyltransferase mediates wax ester and triacylglycerol biosynthesis in *Acinetobacter calcoaceticus* ADP1. J Biol Chem. 2003 Mar. 7; 278(10):8075-82.

Kaneda T. Iso- and anteiso-fatty acids in bacteria: biosynthesis, function, and taxonomic significance. Microbiol Rev. 1991 June; 55(2):288-302.

Kapust R B, Waugh D S. *Escherichia coli* maltose-binding protein is uncommonly effective at promoting the solubility of polypeptides to which it is fused. Protein Sci. 1999 August; 8(8): 1668-74.

Keasling J D, Jones K L, Van Dien S J. New Tools for Metabolic Engineering of *Escherichica coli*. Chapter 5 in Metabolic Engineering. Marcel Dekker. New York, N.Y. 1999. (a)

Keasling J D. Gene-expression tools for the metabolic engineering of bacteria. Trends Biotechnol. 1999 November; 17(11):452-60. (b)

Kelly D P, Wood P, Gottschal J C, Kuenen J G Autotrophic metabolism of formate by *Thiobacillus* strain A2. J Gen Microbiol. 1979; 114:1-13.

Kelly J R, Rubin A J, Davis J H, Ajo-Franklin C M, Cumbers J, Czar M J, de Mora K, Glieberman A L, Monie D D, Endy D. Measuring the activity of BioBrick promoters using an in vivo reference standard. J Biol Eng. 2009 Mar. 20; 3:4.

Kim O B, Unden G The L-tartrate/succinate antiporter TtdT (YgjE) of L-tartrate fermentation in *Escherichia coli*. J Bacteriol. 2007 March; 189(5):1597-603.

Klimke W, Agarwala R, Badretdin A, Chetvemin S, Ciufo S, Fedorov B, Kiryutin B, O'Neill K, Resch W, Resenchuk S, Schafer S, Tolstoy I, Tatusova T. The National Center for Biotechnology Information's Protein Clusters Database. Nucleic Acids Res. 2009 January; 37(Database issue):D216-23.

Knight T. Idempotent Vector Design for Standard Assembly of Biobricks. DOI: 1721.1/21168.

Knight T. BBF RFC10: Draft Standard for BioBrick™ biological parts. DOI: 1721.1/45138.

Larkum A W. Limitations and prospects of natural photosynthesis for bioenergy production. Curr Opin Biotechnol. 2010 June; 21(3):271-6.

Knothe G, Dunn R O, Bagby M O. Biodiesel: The use of vegetable oils and their derivatives as alternative diesel fuels. Am Chem Soc Symp Series. 1997; 666:172-208.

Knothe G. Rapid monitoring of transesterification and assessing biodiesel fuel quality by NIR spectroscopy using a fiber-optic probe. J Am Oil Chem Soc. 1999; 76(7):795-800.

Knothe G. Dependence of biodiesel fuel properties on the structure of fatty acid alkyl esters. Fuel Process Technol. 2005; 86:1059-1070.

Komers K, Skopal F, Stloukal R. Determination of the neutralization number for biodiesel fuel production. Fett/Lipid. 1997; 99(2):52-54.

Larue T A, Kurz W G Estimation of nitrogenase using a colorimetric determination for ethylene. Plant Physiol. 1973 June; 51(6):1074-5.

Li Y, Florova G, Reynolds K A. Alteration of the fatty acid profile of Streptomyces coelicolor by replacement of the initiation enzyme 3-ketoacyl acyl carrier protein synthase III (FabH). J Bacteriol. 2005 June; 187(11):3795-9.

Marrakchi H, Zhang Y M, Rock C O. Mechanistic diversity and regulation of Type II fatty acid synthesis. Biochem Soc Trans. 2002 November; 30(Pt 6):1050-5. (a)

Marrakchi H, Choi K H, Rock C O. A new mechanism for anaerobic unsaturated fatty acid formation in Streptococcus pneumoniae. J Biol Chem. 2002 Nov. 22; 277(47): 44809-16. (b)

Martin V J J, Smolke C, Keasling J D. Redesigning cells for production of complex organic molecules. ASM News. 2002; 68:336-343.

Martínez-Alonso M, Toledo-Rubio V, Noad R, Unzueta U, Ferrer-Miralles N, Roy P, Villaverde A. Rehosting of bacterial chaperones for high-quality protein production. Appl Environ Microbiol. 2009 December; 75(24):7850-4.

Martínez-Alonso M, Garcia-Fruitós E, Ferrer-Miralles N, Rinas U, Villaverde A. Side effects of chaperone gene co-expression in recombinant protein production. Microb Cell Fact. 2010 Sep. 2; 9:64.

Minshull J, Stemmer W P. Protein evolution by molecular breeding. Curr Opin Chem Biol. 1999 June; 3(3):284-90.

Morweiser M, Kruse O, Hankamer B, Posten C. Developments and perspectives of photobioreactors for biofuel production. Appl Microbiol Biotechnol. 2010 July; 87(4): 1291-301.

Murli S, Opperman T, Smith B T, Walker G C. A role for the umuDC gene products of Escherichia coli in increasing resistance to DNA damage in stationary phase by inhibiting the transition to exponential growth. J Bacteriol. 2000 February; 182(4):1127-35.

Murtagh, F. Complexities of Hierarchic Clustering Algorithms: the State of the Art. Computational Statistics Quarterly. 1984; 1:101-13.

Nature Genetics. 1999; 21(1):1-60.

Palaniappan N, Kim B S, Sekiyama Y, Osada H, Reynolds K A. Enhancement and selective production of phoslactomycin B, a protein phosphatase IIa inhibitor, through identification and engineering of the corresponding biosynthetic gene cluster. J Biol Chem. 2003 Sep. 12; 278 (37):35552-7.

Park M O. New pathway for long-chain n-alkane synthesis via 1-alcohol in Vibrio fumrnissii M1. J Bacteriol. 2005 February; 187(4):1426-9.

Patton S M, Cropp T A, Reynolds K A. A novel delta(3), delta(2)-enoyl-CoA isomerase involved in the biosynthesis of the cyclohexanecarboxylic acid-derived moiety of the polyketide ansatrienin A. Biochemistry. 2000 Jun. 27; 39(25):7595-604.

Pramanik J, Keasling J D. Stoichiometric model of Escherichia coli metabolism: incorporation of growth-rate dependent biomass composition and mechanistic energy requirements. Biotechnol Bioeng. 1997 Nov. 20; 56(4): 398-421.

Pramanik J, Keasling J D. Effect of Escherichia coli biomass composition on central metabolic fluxes predicted by a stoichiometric model. Biotechnol Bioeng. 1998 Oct. 20; 60(2):230-8. (a)

Pramanik J, Trelstad P L, Keasling J D. A flux-based stoichiometric model of enhanced biological phosphorus removal metabolism. Wat Sci Technol. 1998; 37(4-5): 609-13. (b)

Pramanik J, Trelstad P L, Schuler A J, Jenkins D, Keasling J D. Development and validation of a flux-based stoichiometric model for enhanced biological phosphorus removal metabolism. Water Res. 1998; 33(2):462-76. (c).

Reading N C, Sperandio V. Quorum sensing: the many languages of bacteria. FEMS Microbiol Lett. 2006 January; 254(1):1-11.

Rock C O, Tsay J T, Heath R, Jackowski S. Increased unsaturated fatty acid production associated with a suppressor of the fabA6(Ts) mutation in Escherichia coli. J Bacteriol. 1996 September; 178(18):5382-7.

Roessner C A, Spencer J B, Ozaki S, Min C, Atshaves B P, Nayar P, Anousis N, Stolowich N J, Holderman M T, Scott A I. Overexpression in Escherichia coli of 12 vitamin B12 biosynthetic enzymes. Protein Expr Purif. 1995 April; 6(2):155-63.

Sachdev D, Chirgwin J M. Solubility of proteins isolated from inclusion bodies is enhanced by fusion to maltose-binding protein or thioredoxin. Protein Expr Purif. 1998 February; 12(1):122-32.

Sachdev D, Chirgwin J M. Fusions to maltose-binding protein: control of folding and solubility in protein purification. Methods Enzymol. 2000; 326:312-21.

Saitou N, Nei M. The neighbor-joining method: a new method for reconstructing phylogenetic trees. Mol Biol Evol. 1987 July; 4(4):406-25.

Sambrook, J, Russell, D. Molecular Cloning: A Laboratory Manual, Third Edition. CSHL Press. Cold Spring Harbor, N.Y. 2001.

San K Y, Bennett G N, Berrios-Rivera S J, Vadali R V, Yang Y T, Horton E, Rudolph F B, Sariyar B, Blackwood K. Metabolic engineering through cofactor manipulation and its effects on metabolic flux redistribution in Escherichia coli. Metab Eng. 2002 April; 4(2): 182-92.

Sauer U, Canonaco F, Heri S, Perrenoud A, Fischer E. The soluble and membrane-bound transhydrogenases UdhA and PntAB have divergent functions in NADPH metabolism of Escherichia coli. J Biol Chem. 2004 Feb. 20; 279(8):6613-9.

Shetty R P, Endy D, Knight T F Jr. Engineering BioBrick vectors from BioBrick parts. J Biol Eng. 2008 Apr. 14; 2:5.

Shetty R, Lizarazo M, Rettberg R, Knight T F. Assembly of BioBrick standard biological parts using three antibiotic assembly. Methods Enzymol. 2011; 498:311-26.

Shpaer E G GeneAssist. Smith-Waterman and other database similarity searches and identification of motifs. Methods Mol Biol. 1997; 70:173-87.

Smolke C D, Carrier T A, Keasling J D. Coordinated, differential expression of two genes through directed mRNA cleavage and stabilization by secondary structures. Appl Environ Microbiol. 2000 December; 66(12): 5399-405.

Smolke C D, Martin V J, Keasling J D. Controlling the metabolic flux through the carotenoid pathway using directed mRNA processing and stabilization. Metab Eng. 2001 October; 3(4):313-21.

Smolke C D, Keasling J D. Effect of copy number and mRNA processing and stabilization on transcript and protein levels from an engineered dual-gene operon. Biotechnol Bioeng. 2002 May 20; 78(4):412-24. (a)

Smolke C D, Keasling J D. Effect of gene location, mRNA secondary structures, and RNase sites on expression of two genes in an engineered operon. Biotechnol Bioeng. 2002 Dec. 30; 80(7):762-76. (b)

Sokal R, Michener, C. A Statistical Method for Evaluating Systematic Relationships. University of Kansas Science Bulletin. 1958; 38:1409-38.

Strom T, Ferenci T, and Quayle J R. The carbon assimilation pathways of *Methylococcus capsulatus, Pseudomonas methanica* and *Methylosinus trichosporium* (OB3B) during growth on methane. Biochem J 1974 December; 144(3) 465-76.

Tatusov R L, Koonin E V, Lipman D J. A genomic perspective on protein families. Science. 1997 Oct. 24; 278 (5338):631-7.

Tatusov R L, FedorovaND, Jackson J D, Jacobs A R, Kiryutin B, Koonin E V, Krylov D M, Mazumder R, Mekhedov S L, Nikolskaya A N, Rao B S, Smirnov S, Sverdlov A V, Vasudevan S, Wolf Y I, Yin J J, Natale D A. The COG database: an updated version includes eukaryotes. BMC Bioinformatics. 2003 Sep. 11; 4:41.

van Wezel G P, Mahr K, Konig M, Traag B A, Pimentel-Schmitt E F, Willimek A, Titgemeyer F. GlcP constitutes the major glucose uptake system of *Streptomyces coelicolor* A3(2). Mol Microbiol. 2005 January; 55(2):624-36.

Venturi V. Regulation of quorum sensing in *Pseudomonas*. FEMS Microbiol Rev. 2006 March; 30(2):274-91.

Wubbolts M G S Terpstra P, van Beilen J B, Kingma J, Meesters H A, Witholt B. Variation of cofactor levels in *Escherichia coli*. Sequence analysis and expression of the pncB gene encoding nicotinic acid phosphoribosyltransferase. J Biol Chem. 1990 Oct. 15; 265(29):17665-72.

Yoon Y G; Cho J H, Kim S C. Cre/loxP-mediated excision and amplification of large segments of the *Escherichia coli* genome. Genet Anal. 1998 January; 14(3):89-95.

Zdobnov E M, Apweiler R. InterProScan—an integration platform for the signature-recognition methods in InterPro. Bioinformatics. 2001 September; 17(9):847-8.

Zhang C C, Durand M C, Jeanjean R, Joset F. Molecular and genetical analysis of the fructose-glucose transport system in the cyanobacterium *Synechocystis* PCC6803. Mol Microbiol. 1989 September; 3(9): 1221-9.

Zhang Y M, Marrakchi H, Rock C O. The FabR (YijC) transcription factor regulates unsaturated fatty acid biosynthesis in *Escherichia coli*. J Biol Chem. 2002 May 3; 277(18):15558-65.

Zhu X, Yuasa M, Okada K, Suzuki K, Nakagawa T, Kawamukai M, Matsuda H. Production of ubiquinone in *Escherichia coli* by expression of various genes responsible for ubiquinone biosynthesis. J Ferm Bioeng. 1995; 79(5):493-5.

The invention claimed is:

1. A polynucleotide comprising SEQ ID NO: 2.

2. A methylotrophic host cell from the genus *Paracoccus* for producing a carbon-based product, comprising an engineered carbon product biosynthetic pathway, wherein the methylotrophic host cell is capable of converting formate into a carbon-based product of interest, wherein the carbon-based product of interest is an isoprenoid, wherein the engineered carbon product biosynthetic pathway comprises a heterologous polynucleotide encoding an isopentenyl pyrophosphate isomerase, and wherein the isopentenyl pyrophosphate isomerase comprises a sequence that is at least 90% identical to the *E. coli* isopentenyl pyrophosphate isomerase protein encoded by SEQ ID NO: 2, wherein the protein encoded by SEQ ID NO: 2 corresponds to NCBI Reference Sequence: NP_417365.1, and wherein the methylotrophic host cell is capable of growth on electrolytically generated formate.

3. The methylotrophic host cell of claim 2, wherein the host cell is a *Paracoccus versutus* cell.

4. The methylotrophic host cell of claim 2, wherein the host cell is a *Paracoccus denitrificans* cell.

5. The methylotrophic host cell of claim 2, wherein the host cell is a *Paracoccus zeaxanthinifaciens* cell.

6. The methylotrophic host cell of claim 2, wherein the isoprenoid is a triterpene.

7. The methylotrophic host cell of claim 2, wherein the isoprenoid is isoprene.

8. The methylotrophic host cell of claim 2, wherein the methylotrophic host cell is component of a high-cell density bioreactor.

9. The methylotrophic host cell of claim 2, wherein the methylotrophic host cell further comprises a formate transporter.

10. The methylotrophic host cell of claim 2, wherein the heterologous polynucleotide comprises the sequence of SEQ ID NO: 2.

* * * * *